US010925999B2

(12) United States Patent
Hanna et al.

(10) Patent No.: US 10,925,999 B2
(45) Date of Patent: Feb. 23, 2021

(54) TUNABLE COVALENTLY CROSSLINKED HYDROGELS AND METHODS OF MAKING THE SAME

(71) Applicant: TRUSTEES OF TUFTS COLLEGE, Medford, MA (US)

(72) Inventors: Craig W. Hanna, Jamaica Plain, MA (US); Benjamin P. Partlow, Winchester, MA (US); David L. Kaplan, Concord, MA (US)

(73) Assignee: Trustees of Tufts College, Medford, MA (US)

( * ) Notice: Subject to any disclaimer, the term of this patent is extended or adjusted under 35 U.S.C. 154(b) by 0 days.

(21) Appl. No.: 15/027,468

(22) PCT Filed: Oct. 6, 2014

(86) PCT No.: PCT/US2014/059287
§ 371 (c)(1),
(2) Date: Apr. 6, 2016

(87) PCT Pub. No.: WO2015/054125
PCT Pub. Date: Apr. 16, 2015

(65) Prior Publication Data
US 2016/0256604 A1 Sep. 8, 2016

Related U.S. Application Data

(60) Provisional application No. 61/888,235, filed on Oct. 8, 2013.

(51) Int. Cl.
| | | |
|---|---|---|
| A61L 27/22 | (2006.01) |
| A61L 27/50 | (2006.01) |
| A61L 27/52 | (2006.01) |
| A61K 9/00 | (2006.01) |
| A61K 47/46 | (2006.01) |
| A61L 27/58 | (2006.01) |
| C07K 14/435 | (2006.01) |
| A61K 47/42 | (2017.01) |
| A61K 9/06 | (2006.01) |
| A61L 27/18 | (2006.01) |
| A61K 35/00 | (2006.01) |
| A61L 27/20 | (2006.01) |
| A61L 27/36 | (2006.01) |
| C08J 3/075 | (2006.01) |
| A61L 27/38 | (2006.01) |
| A61L 27/54 | (2006.01) |
| C12P 21/00 | (2006.01) |

(52) U.S. Cl.
CPC .......... *A61L 27/227* (2013.01); *A61K 9/0019* (2013.01); *A61K 9/06* (2013.01); *A61K 35/00* (2013.01); *A61K 47/42* (2013.01); *A61K 47/46* (2013.01); *A61L 27/18* (2013.01); *A61L 27/20* (2013.01); *A61L 27/22* (2013.01); *A61L 27/3604* (2013.01); *A61L 27/3834* (2013.01); *A61L 27/50* (2013.01); *A61L 27/52* (2013.01); *A61L 27/54* (2013.01); *A61L 27/58* (2013.01); *C07K 14/43586* (2013.01); *C08J 3/075* (2013.01); *C12P 21/00* (2013.01); *A61L 2300/64* (2013.01); *A61L 2400/06* (2013.01); *C08J 2389/00* (2013.01)

(58) Field of Classification Search
None
See application file for complete search history.

(56) References Cited

U.S. PATENT DOCUMENTS

| | | | |
|---|---|---|---|
| 5,245,012 A | 9/1993 | Lombari et al. | |
| 2004/0018160 A1 | 1/2004 | Hu et al. | |
| 2004/0067503 A1 | 4/2004 | Tan et al. | |
| 2012/0156176 A1* | 6/2012 | Fujimoto | A61K 9/0024 424/93.7 |
| 2012/0177604 A1* | 7/2012 | Kurisawa | C08J 3/00 424/85.7 |
| 2013/0032963 A1* | 2/2013 | Tokiwa | B29C 49/0005 264/51 |
| 2013/0288366 A1* | 10/2013 | Li | C12N 5/0619 435/368 |
| 2014/0314817 A1* | 10/2014 | Leisk | A61L 27/227 424/400 |
| 2015/0010630 A1* | 1/2015 | Llamas | A61L 27/227 424/484 |

FOREIGN PATENT DOCUMENTS

| | | |
|---|---|---|
| EP | 1169922 A1 | 1/2002 |
| PT | 106041 A * | 6/2013 |
| WO | WO-1997/008315 A1 | 3/1997 |
| WO | WO-2004/080346 A2 | 9/2004 |

(Continued)

OTHER PUBLICATIONS

Gil et al. Macromolec. Biosci. (2005) 5: 702-709.*

(Continued)

*Primary Examiner* — Susan M Hanley
(74) *Attorney, Agent, or Firm* — Quarles & Brady, LLP

(57) ABSTRACT

The present invention provides, among other things, a elastomeric biomaterial having enzymatically cross-linked amino acid phenolic side chains to generate highly elastic hydrogels. Materials are characterized by tunable mechanical properties, gelation kinetics and swelling properties of these new protein polymers. Provided materials are support encapsulation of cells. Methods of making and using of provided particles are also disclosed.

17 Claims, 30 Drawing Sheets

(56) References Cited

FOREIGN PATENT DOCUMENTS

| WO | WO-2005/012606 A2 | 2/2005 |
|---|---|---|
| WO | WO-2005/123114 A2 | 12/2005 |
| WO | WO-2007/016524 A2 | 2/2007 |
| WO | WO-2008/118133 A2 | 10/2008 |
| WO | WO-2008/150861 A1 | 12/2008 |

OTHER PUBLICATIONS

Lehninger "Biochemistry" (1975) Second Edition. Worth Publishers: New York) pp. 133-134.*
Killion et al. J. Mechanical Behavior Biomed. Mat. (2011) 4: 1219-1227 (Year: 2011).*
Machine translation of PT 106041, published Jun. 6, 2013 downloaded from ProQuest (Year: 2013).*
Lougee from the sciencing website: https://sciencing.com/what-is-an-aqueous-solution-13712159.html, updated Apr. 26, 2018, downloaded Jul. 25, 2019. (Year: 2018).*
Partlow et al. Adv. Funct.Mater. (2014) 24: 4615-4624; published Apr. 14, 2014 (Year: 2014).*
Altman, G.H. et al., Silk-based biomaterials, Biomaterials, 24(3):401-416 (2003).
Bini, E. et al., Mapping domain structures in silks from insects and spiders related to protein assembly, Journal of Molecular Biology, 335(1):27-40 (2004).
International Search Report for PCT/US2014/059287 (Tunable and Elastic Enzymatically Crosslinked Silk Fibroin Hydrogels and Methods of Making the Same, filed Oct. 6, 2007), issued by ISA/RU, 2 pages dated (Jan. 29, 2015).
Kikuchi, Y. et al., Structure of the Bombyx mori fibroin light-chain-encoding gene: upstream sequence elements common to the light and heavy chain, Gene, 110(2):151-8 (1992).
Lucas, F. et al., The Silk Fibroins, Silk Department, Shirley Institute, Manchester, England, 13:107-242 (1958).
Omenetto, F.G. and Kaplan, D.L., New Opportunities for an Ancient Material, Science, 329:528-531 (2010).
Rockwood, D.N. et al., Materials Fabrication from *Bombyx mori* Silk Fibroin, Nature Protocols 6(10):1612-1631 2011).
Takai, F. et al., Further Evidence for Importance of the Subunit Combination of Silk Fibroin in its Efficient Secretion from the Posterior Silk Gland Cells, The Journal of Cell Biology, 105:175-180 (1987).
Tanaka, K. et al., Determination of the site of disulfide linkage between heavy and light chains of silk fibroin produced by Bombyx mori, Biochimica et Biophysica Acta, 1432:92-103 (1999).
Tanaka, K. et al., Immunological Identification of the Major Disulfide-Linked Light Component of Silk Fibroin, J. Biochem, 114:1-4 (1993).
Tsubouchi, K. et al., Bombyx mori Fibroin Enhanced the Proliferation of Cultured Human Skin Fibroblasts, Journal of Insect Biotechnology and Sericology, 72:65-69 (2003).
Wray, L. et al., Effect of processing on silk-based biomaterials: reproducibility and biocompatibility, J Biomed Mater Res B Appl Biomater, 99(1):89-101 (2011).
Written Opinion for PCT/US2014/059287, Tunable and Elastic Enzymatically Crosslinked Silk Fibroin Hydrogels and Methods of Making the Same, filed Oct. 6, 2007), issued by ISA/RU, 4 pages dated (Jan. 29, 2015).

* cited by examiner (A)

(B)

(C)

(A)

(B)

TUNABLE COVALENTLY CROSSLINKED HYDROGELS AND METHODS OF MAKING THE SAME

CROSS-REFERENCE TO RELATED APPLICATIONS

This patent application is a National Stage Entry of International Patent Application No. PCT/US2014/059287, filed on Oct. 6, 2014, which claims priority to and the benefit of, U.S. provisional patent application Ser. No. 61/888,235, filed on Oct. 8, 2013, the entire contents of each of which are hereby incorporated by reference herein.

GOVERNMENT SUPPORT

This invention was made with government support under grant EB002520 awarded by the National Institutes of Health. The government has certain rights in the invention.

BACKGROUND

Silk fibroins are produced by numerous species of spiders and by worms from various insects such as bees, butterflies, and moths. Silks produced by silkworms (typically *Bombyx mori*) and orb-weaving spiders have desirable mechanical properties, environmental stability, biocompatibility, and tunable degradation. In addition, these silks can be modified to deliver agents such as antibiotics, drugs, and growth factors to enhance healing in biomedical applications. Silk have been previously discussed to be used in biomedical applications, e.g., silk sutures (Vepari and Kaplan 2007).

SUMMARY

The present invention provides, among other things, covalently crosslinked polymer hydrogels (e.g., silk hydrogels). Provided covalently crosslinked hydrogels are useful, for example, for cell growth applications including cell engineering and/or tissue regeneration. The present invention also provides methods of preparing and using such hydrogels.

In some embodiments, covalently crosslinked hydrogels of the present invention are characterized by highly tunable mechanical properties. That is, the present invention provides technologies that permit production and use of covalently crosslinked hydrogels whose mechanical properties are tuned to a particular desired range and/or set. In some embodiments, covalently crosslinked hydrogels of the present invention are characterized by mechanical properties (e.g., pore size, strength [e.g., as assessed by storage modulus], flexibility, stiffness, etc.) that are particularly suitable for use in supporting cell growth, function, viability, and/or differentiation. To give but one example, in some embodiments, provided covalently crosslinked hydrogels are characterized by mechanical properties that support living cells, including, for example as evidenced by outgrowth of extensions on human mesenchymal stem cells. In some embodiments, covalently crosslinked hydrogels of the present invention are characterized by particular degradation properties. In some embodiments, covalently crosslinked hydrogels of the present invention degrade to release an agent useful for treatment of a disease, disorder, or condition.

In some embodiments, covalently crosslinked hydrogels of the present invention comprise polymers. In some embodiments, hydrogels of the present invention comprise protein polymers. In some embodiments, useful protein polymers are selected from the group consisting of agarose, alginate, cellulose, chitin, chitosan, collagen, elastin, gelatin, hyaluronic acid, polydimethylsiloxane, poly(ethylene glycol), polyhydroxyalkanoates, poly(lactide-co-glycolide), pullan, resilin, silk, starch, and combinations thereof.

In some embodiments, covalently crosslinked hydrogels of the present invention comprise silk polymers (e.g., silk fibroin polymers).

In some embodiments, provided covalently crosslinked hydrogels are comprised of low molecular weight polymers, for example in that the hydrogels are substantially free of, and/or are prepared from solutions that are substantially free of, polymers having a molecular weight above about 400 kDa. In some embodiments, the highest molecular weight polymers in provided hydrogels are less than about 300 kDa-about 400 kDa (e.g., less than about 400 kDa, less than about 375 kDa, less than about 350 kDa, less than about 325 kDa, less than about 300 kDa, etc.). In some embodiments, provided hydrogels are comprised of polymers (e.g., protein polymers) having molecular weights within the range of about 20 kDa-about 400 kDa. In some embodiments, provided hydrogels are comprised of polymers (e.g., protein polymers) having molecular weights within a range between a lower bound (e.g., about 20 kDa, about 30 kDa, about 40 kDa, about 50 kDa, about 60 kDa, or more) and an upper bound (e.g., about 400 kDa, about 375 kDa, about 350 kDa, about 325 kDa, about 300 kDa, or less). In some embodiments, provided hydrogels are comprised of polymers (e.g., protein polymers) having a molecular weight around 60 kDa, or less. Those skilled in the art will appreciate that, typically, when a provided hydrogel is said to include a particular polymer of a specified molecular weight (including within a specified molecular weight range), the hydrogel is substantially free of other molecular weight species of that polymer.

Discussed herein and/or known in the art are various technologies for obtaining or preparing polymers of particular molecular weights. To give but one example, it is known in the art that different molecular weight preparations of silk fibroin may be prepared or obtained by boiling silk solutions (e.g., as is typically done during degumming processes) for different amounts of time. For example, careful studies (see, for example, Wray et al., Effect of Processing on Silk-Based Biomaterials: Reproducibility and Biocompaticility, 99 J. Biomed. Mat. Res. Part B: Applied Biomaterials, 89-101 (epub 21 Jun., 2011), which is incorporated by reference in its entirety herein) of effects of different boiling times on silk fibroin solutions have established, among other things, that boiling for particular specific amounts of time results in silk fibroin compositions characterized by particular ranges of molecular weights. For example, under certain established conditions, boiling for 5 minutes results in preparations ("5 mb" preparations) characterized by relatively high molecular weight silk (e.g., within the range of about 300 kD-about 400 kD), boiling for 30 minutes results in preparations ("30 mb" preparations) characterized by a molecular weight distribution with a peak around 100 kD), and boiling for 60 minutes results in preparations ("60 mb" preparations) characterized by lower molecular weights (e.g., with a distribution that peaks around 60 kD).

Moreover, compositions boiled for these different times are known to have different material properties attributable to their different molecular weights, even when they show comparable β-sheet character. For example, as reported by Wray et al, report that initial degradation of samples boiled for longer times is faster than that of samples boiled for shorter times. Also, scaffold assembly from samples boiled for different periods of time resulted in distinct differences in macroscopic shape, pore size, and porosity. Specifically, both the 5 mb and 60 mb samples displayed a wide range of pore sizes, but the 60 mb sample displayed less pore interconnectivity. The 30 mb sample displayed homogenous pore samples that were highly interconnected. Viability of endothelial cells cultured in direct contact with silk films prepared from the variously-boiled samples also decreased as duration of boiling increased (and molecular weight decreased). Other studies (e.g., Tsubouchi et al *J Insect Biotechnol Sericol* 72:65, 2003 reported that human skin fibroblast cell viability remains strong (and improved relative to a control) for samples boiled for 5, 10, or 30 minutes; samples boiled for 60 min were reported to hinder cell viability.

In some embodiments, provided technologies utilize simple methods and/or do not require or utilize organic solvents (particularly not volatile organic solvents).

Also, in some embodiments, provided technologies prepare hydrogels in water. In some embodiments, provided technologies prepare hydrogels at sub-physiological pH and/or from solutions at sub-physiological pH. In some embodiments, such sub-physiological pH is at or near pH 6; in some embodiments, such sub-physiological pH is below 6. In some embodiments, the present disclosure encompasses the insight that use of buffered and/or salt-containing solutions (e.g., PBS) and/or solutions with higher pH (e.g., substantially physiological, or above, for example at, around, or above pH 7) can negatively impact mechanical properties of resulting hydrogels. Without wishing to be bound by any particular theory, the present disclosure proposes that use of such solutions can impact interactions between polymer chains in the hydrogel. For example, such interactions may be weaker in the presence of salt(s) than in water. According to some embodiments, provided water-prepared hydrogels show greater rigidity than those prepared from salt-containing or buffered solutions. In some embodiments, provided water-prepared hydrogels show improved cell viability and/or behavior as compared with those prepared from salt-containing or buffered solutions.

In certain particular embodiments, cross-linking as described herein is performed on polymer (e.g., silk) solutions that are substantially free of salts and/or other buffering agents. In some cross-linking as described herein is performed on polymer (e.g., silk) solutions in water.

In some embodiments, provided hydrogels are biocompatible. In some embodiments, provided hydrogels are biodegradable. In some embodiments, provided hydrogels are biocompatible and biodegradable.

In some embodiments, a protein polymer for use in the practice of the present invention includes amino acid residues with phenolic side chains. In some embodiments, such amino acid residues include tyrosines.

In some embodiments, provided hydrogels comprise covalently crosslinked protein polymers. In some embodiments, such hydrogels comprise cross-links that utilize amino acid residue side chains (e.g., phenolic side chains). In some embodiments, provided hydrogels comprise enzymatically covalently crosslinked polymers (e.g., protein polymers).

In some embodiments, polymers in such provided hydrogels are cross-linked via tyrosine residues. In some embodiments, crosslinks in provided hydrogels are or include dityrosine covalent bonds.

In some embodiments, provided hydrogels are characterized by crystalline structure, for example, comprising beta sheet structure and/or hydrogen bonding. In some embodiments, provided hydrogels are characterized by a percent beta sheet structure within the range of about 0% to about 45%.

In some embodiments, provided covalently crosslinked hydrogels are characterized by a desired high storage modulus value. In some embodiments, a high storage modulus value corresponds with a strong and/or robust hydrogel. In some embodiments, provided covalently crosslinked hydrogels having a high storage modulus value are characterized in that they are formed from solutions that have a low weight percent polymer concentration. In some particular embodiments exemplified herein, provided covalently crosslinked hydrogels are characterized by a storage modulus value between about 50 Pa and about 100 kPa without showing an indication of a plastic deformation. In some particular embodiments exemplified herein, provided covalently crosslinked hydrogels are characterized by a storage modulus value great than about 1 kPa without showing an indication of a plastic deformation. In some embodiments, covalently crosslinked hydrogels of the present invention are characterized in that they recover from a shear strain of at least 100% while resisting degradation and without showing evidence of a plastic deformation.

In some embodiments, provided covalently crosslinked hydrogels are characterized by high elasticity. Elasticity or elastic deformation generally measures a tendency of a material to return to its original size and/or shape after a force having been applied to the material and having deformed the material is subsequently removed. In contrast, plastic deformation follows application of enough stress on a material to cause a change in the size and/or shape of the material in a way that is not reversible, such that the material does not return to its original size and/or shape. A plastic deformation specifically involves a change to the structure of the material, such as a molecular and/or atomic shift or dislocation from which the material cannot recover. In some embodiments, provided covalently crosslinked hydrogels of the present invention are characterized as having a tangent modulus value between about 200 Pa to about 400 kPa without showing an indication of a plastic deformation. In some embodiments, covalently crosslinked, hydrogels of the present invention are characterized in that they recover from a compressive strain of at least 75% while resisting degradation and without showing evidence of a plastic deformation.

In some embodiments, provided covalently crosslinked hydrogels are characterized by a high resiliency. Resiliency provides an indication of an ability of a material to absorb energy when a force is applied and the material is deformed and subsequently release energy when the force is removed permitting the material to return to its natural state. In some embodiments, provided covalently crosslinked hydrogels of the present invention are characterized as highly resilient to a repetitive force with high cycle. In some embodiments, a high cycle is at least 3,600 cycles at a frequency 0.5 Hz. In some embodiments, covalently crosslinked hydrogels of the present invention are characterized in that they recover from exposure to a compressive strain of at least 10% at a high cycle without showing evidence of a plastic deformation. In some embodiments, covalently crosslinked hydrogels of the present invention are characterized in that they recover from exposure to a shear strain of at least 10% at a high cycle without showing evidence of a plastic deformation.

In some embodiments, covalently crosslinked hydrogels of the present invention are characterized in that they swell up to 400% when exposed to solvents without showing evidence of a plastic deformation.

In some embodiments, provided covalently crosslinked hydrogels are characterized by an ability to recover from strain and/or compression.

In some embodiments, provided covalently crosslinked hydrogels are configured to support encapsulation of at least one cell. In some embodiments, a covalently crosslinked hydrogel of the present invention is configured as a matrix capable of encapsulating a plurality of cells.

In some embodiments, provided covalently crosslinked hydrogels are configured to support viability and/or growth of encapsulated cells.

In some embodiments, provided covalently crosslinked hydrogels are configured to inhibit cell extensions and prevent cell/hydrogel interaction essentially confining the cell within the silk matrix while maintaining viability.

In some embodiments, provided covalently crosslinked hydrogels are configured to allow formation of cell extensions and promote cell/cell and cell/matrix interactions and enhance spreading. In some embodiments, provided covalently crosslinked hydrogels with desired high storage modulus values are formed from low weight percent concentration of polymer solution. In some particular embodiments exemplified herein, provided covalently crosslinked hydrogels with high storage modulus values formed from a polymer solution with a low weight percent concentration of polymer are characterized by an environment suited to cell incorporation, so that cells exhibited in growth, viability, and differentiation.

In some embodiments, provided covalently crosslinked hydrogels are configured to support encapsulation of at least one biological or biologically active agent. In some embodiments, provided covalently crosslinked hydrogels may encapsulate or otherwise comprise at least one biological or biologically active agent. In some embodiments, provided covalently crosslinked hydrogels that encapsulate or otherwise comprise at least one biological or biologically active agent may release the agent as a covalently crosslinked hydrogel degrades.

In some embodiments, provided covalently crosslinked hydrogels are characterized in that encapsulated biologically active agents retain structural and/or functional integrity over time to a greater degree than is observed when the agents are stored under comparable conditions without being so encapsulated.

In some embodiments, hydrogels of the present invention are configured to support incorporation of and/or modification with one or more functional moieties. In some embodiments, hydrogels of the present invention provide tunable mechanical properties that support encapsulation cells, for example for cell engineering and/or tissue regeneration applications including for example in the treatment or prevention of a disease, disorder or condition and/or for inducing tissue repair.

In some embodiments, encapsulation/incorporation and/or degradation characteristics of such covalently crosslinked hydrogels are tuned according to fabrication conditions (e.g., molecular weight of polymer, wt % of polymer in solution from which the covalently crosslinked hydrogel is prepared, nature and/or degree of crosslinking, nature and/or degree of modification [e.g., with one or more agents and/or functional moieties], etc.).

In some embodiments, covalently crosslinked hydrogels of the present invention are provided, prepared, and/or manufactured from a protein polymer (e.g. silk, such as silk fibroin) solution. In some embodiments, useful protein polymers are selected from the group consisting of agarose, alginate, cellulose, chitin, chitosan, collagen, elastin, gelatin, hyaluronic acid, polydimethylsiloxane, poly(ethylene glycol), polyhydroxyalkanoates, poly(lactide-co-glycolide), pullan, resilin, silk, starch, and combinations thereof. In some embodiments, crosslinking may include functionalization, for example, an addition of a phenol group.

In some embodiments, a covalently crosslinked hydrogel of the present invention is provided, prepared, and/or manufactured from a solution of a protein polymer having a molecular weight in the range of about 20 kD-about 400 kD. In some embodiments, provided, prepared, and/or manufactured covalently crosslinked hydrogels of the present invention are comprised of polymers (e.g., protein polymers) having molecular weights within a range between a lower bound (e.g., about 20 kD, about 30 kD, about 40 kD, about 50 kD, about 60 kD, or more) and an upper bound (e.g., about 400 kD, about 375 kD, about 350 kD, about 325 kD, about 300 kD, or less). In some embodiments, provided, prepared, and/or manufactured covalently crosslinked hydrogels are comprised of polymers (e.g., protein polymers) having a molecular weight around 60 kD.

In some particular embodiments, a covalently crosslinked hydrogel of the present invention is provided, prepared, and/or manufactured from a solution of silk fibroin that has been boiled and/or degummed to remove sericin for at least about 5, 10, 15, 20, 25, 30, 35, 40, 45, 50, 55, 60, 70, 80, 90, 100, 110, 120, 150, 180, 210, 240, 270, 310, 340, 370, 410 minutes or more. In some embodiments, such degumming is performed at a temperature within the range of: about 30° C., about 35° C., about 40° C., about 45° C., about 50° C., about 45° C., about 60° C., about 65° C., about 70° C., about 75° C., about 80° C., about 85° C., about 90° C., about 95° C., about 100° C., about 105° C., about 110° C., about 115° C., about at least 120° C. In some embodiments, such degumming is performed at a temperature below about 65° C. In some embodiments, such degumming is performed at a temperature of about 60° C. or less.

In some embodiments, a covalently crosslinked hydrogel of the present invention is provided, prepared, and/or manufactured from a solution of protein polymer (e.g., of silk such as silk fibroin) that is adjusted to (e.g., by dialysis) and/or maintained at a sub-physiological pH (e.g., at or below a pH significantly under pH 7). For example, in some embodiments, a covalently crosslinked hydrogel of the present invention is provided, prepared, and/or manufactured from a solution of protein polymer that is adjusted to and/or maintained at a pH near or below about 6. In some embodiments, covalently crosslinked hydrogels are provided, prepared, and/or manufactured from a solution of protein polymer with a pH for instance about 6 or less, or about 5 or less. In some embodiments, covalently crosslinked hydrogels are provided, prepared, and/or manufactured from a solution of protein polymer with a pH in a range for example of at least 6, at least 7, at least 8, at least 9, and at least about 10.

In some embodiments, a covalently crosslinked hydrogel of the present invention is provided, prepared, and/or manufactured from an aqueous solution of protein polymer (e.g., of silk such as silk polymer) where the solvent is water, PBS and combinations thereof. In some embodiments, a covalently crosslinked hydrogel of the present invention is provided, prepared, and/or manufactured from an aqueous protein polymer solution in a solvent other than PBS. In some embodiments, a covalently crosslinked hydrogel of the present invention is provided, prepared, and/or manufactured from a solution of protein polymer in water. In some embodiments, a covalently crosslinked hydrogel of the present invention is provided, prepared, and/or manufactured from a solution of protein polymer in DMEM. In some embodiments, a covalently crosslinked hydrogel of the present invention is provided, prepared, and/or manufactured from an aqueous protein polymer solution that is not buffered.

In some embodiments, a covalently crosslinked hydrogel of the present invention is provided, prepared, and/or manufactured from a protein polymer (e.g., silk such as silk fibroin) solution of about 0.1 wt % polymer to about 30 wt % polymer. In some embodiments, a covalently crosslinked hydrogel of the present invention is provided, prepared, and/or manufactured from a protein polymer (e.g., silk such as silk fibroin) solution that is less than about 30 wt % polymer. In some embodiments, a covalently crosslinked hydrogel of the present invention is provided, prepared, and/or manufactured from a protein polymer (e.g., silk such as silk fibroin) solution that is less than about 20 wt % polymer. In some embodiments, a covalently crosslinked hydrogel of the present invention is provided, prepared, and/or manufactured from a protein polymer (e.g., silk such as silk fibroin) solution that is less than about 10 wt % polymer. Indeed, in some embodiments, the present invention provides the surprising teaching that useful covalently crosslinked hydrogels with particularly valuable properties can be provided, prepared, and/or manufactured from a protein polymer (e.g., silk such as silk fibroin) solution that is less than about 10 wt % polymer, or even that is about 5% wt %, about 4 wt %, about 3 wt %, about 2 wt %, about 1 wt % polymer or less.

In some embodiments, methods of providing, preparing, and/or manufacturing covalently crosslinked hydrogels of the present invention comprise forming crosslinks utilizing amino acid residue side chains (e.g., phenolic side chains) present within polymers (e.g., protein polymers). In some embodiments, methods of providing, preparing, and/or manufacturing covalently crosslinked hydrogels of the present invention comprise forming crosslinks via tyrosine residues to form dityrosine covalent bonds.

In some embodiments, methods of providing, preparing, and/or manufacturing a covalently crosslinked hydrogel in accordance with the present invention comprises enzymatically introducing crosslinks. In some embodiments, a method of providing, preparing, and/or manufacturing a covalently crosslinked hydrogel in accordance with the present invention comprises introducing crosslinks with peroxidase (e.g., in the presence of peroxide). In some embodiments, a peroxidase selected from the group consisting of animal heme-dependent peroxidase, bromoperoxidase, glutathione peroxidase, haloperoxidase, horseradish peroxidase, lactoperoxidase, myeloperoxidase, thyroid peroxidase, vanadium and combinations thereof. In some embodiments, a peroxidase is utilized at a concentration between about 0.001 mg/mL and about 10 mg/mL. In some embodiments, a peroxide is selected from the group consisting of barium peroxide, calcium peroxide, hydrogen peroxide, sodium peroxide, organic peroxides and combinations thereof.

In some embodiments, methods of providing, preparing, and/or manufacturing a covalently crosslinked hydrogel in accordance with the present invention includes gelation of a polymer (e.g. a protein polymer). In some embodiments, gelation is initiated on combining a polymer solution, a peroxidase solution, and a peroxide. In some embodiments, a gelation reaction forming a hydrogel is complete between about 20 seconds and about 5000 seconds after gelation is induced.

In some embodiments, methods of providing, preparing, and/or manufacturing a covalently crosslinked hydrogel of the present invention comprises providing a silk solution. In some embodiments silk comprises tyrosine side chains. In some embodiments, a method of providing, preparing, and/or manufacturing a covalently crosslinked hydrogel of the present invention comprises boiling silk in $Na_2CO_3$ for about 10 minutes, about 20 minutes, about 30 minutes, or about 60 minutes. In some embodiments, silk fibers were solubilized in lithium bromide (LiBr) and then dialyzed against water to yield a polymer molecular weight of between about 10 kDa and about 400 kDa and a polymer concentration of between about 0.1 wt % and about 30 wt %. In some embodiments, a method of providing, preparing, and/or manufacturing a covalently crosslinked hydrogel of the present invention comprises adding a solution of horseradish peroxidase to the silk solution. In some embodiments, a method of providing, preparing, and/or manufacturing a covalently crosslinked hydrogel of the present invention comprises adding hydrogen peroxide to the combined solution of silk and horseradish peroxidase, thereby inducing gelation.

In some embodiments, methods of providing, preparing, and/or manufacturing a covalently crosslinked hydrogel of the present invention includes incorporating one or more functional moieties. In some embodiments, a step of incorporating comprises modifying a covalently crosslinked hydrogel of the present invention with a functional moiety. In some embodiments, a step of incorporating occurs prior to gelation. In some embodiments, a step of incorporating occurs after to gelation. For example, in some embodiments, a step of incorporating a biological and/or biologically active agent can occur before or after before gelation is induced, during gelation, or after gelation and/or crosslinking has completed.

In some embodiments, methods of using a covalently crosslinked hydrogel of the present invention comprises adhering cells to a surface of a covalently crosslinked hydrogel. In some embodiments, a method of using a covalently crosslinked hydrogel of the present invention comprises encapsulating cells within a matrix a covalently crosslinked hydrogel. In some embodiments, a method of using a covalently crosslinked hydrogel of the present invention comprises encapsulating cells for introducing cells to a native tissue. In some embodiments, a method of using a covalently crosslinked hydrogel of the present invention comprises influencing cell shape.

In some embodiments, methods of providing, preparing, and/or manufacturing a covalently crosslinked hydrogel of the present invention for use in encapsulating cells comprises tuning resilience and/or elasticity between a covalently crosslinked hydrogel and a native tissue. In some embodiments, a method of providing, preparing, and/or manufacturing a covalently crosslinked hydrogel of the present invention for use in influencing cell shape comprises tuning resilience and/or elasticity between a covalently crosslinked hydrogel and a native tissue.

In some embodiments, mechanical properties provide an indication of resilience and/or elasticity between a covalently crosslinked hydrogel and a native tissue. In some embodiments, a method of providing, preparing, and/or manufacturing a covalently crosslinked hydrogel of the present invention for use in encapsulating cells and/or influencing cell shape comprises matching, tuning, adjusting, and/or manipulating mechanical properties of covalently crosslinked hydrogels of the present invention. In some embodiments, mechanical properties include, for example, storage modulus, tangent modulus, plateau modulus, swelling, and/or dynamic modulus.

In some embodiments, matching, tuning, adjusting, and/or manipulating mechanical properties of a covalently crosslinked hydrogel include controlling, for example: by selecting a molecular weight of a polymer, by selecting a concentration of a polymer solution, by selecting a specific polymer, by selecting a specific peroxidase, by selecting a specific peroxide, and by combinations thereof.

In some embodiments, matching, tuning, adjusting, and/or manipulating mechanical properties of a covalently crosslinked hydrogel of the present invention for use in encapsulating cells and/or influencing cell shape is accomplished, at least in part, by selecting a molecular weight of a polymer. In some embodiments, a molecular weight of a polymer is in a range of molecular weights between about 10 kDa and about 400 kDa.

In some embodiments, matching, tuning, adjusting, and/or manipulating mechanical properties of a covalently crosslinked hydrogel of the present invention for use in encapsulating cells and/or influencing cell shape is accomplished, at least in part, by selecting a polymer solution concentration. In some embodiments, a polymer solution concentration is in a range of concentrations between about 0.1 wt % and about 30 wt %.

In some embodiments, matching, tuning, adjusting, and/or manipulating mechanical properties of a covalently crosslinked hydrogel of the present invention for use in encapsulating cells and/or influencing cell shape is accomplished, at least in part, by selecting a molecular weight of a polymer and selecting a polymer solution concentration.

In some embodiments, a method of providing, preparing, and/or manufacturing a covalently crosslinked hydrogel of the present invention comprises controlling a rate of degradation of a covalently crosslinked hydrogel of the present invention for maintaining a covalently crosslinked hydrogel shape, optimizing infiltration and/or integration of a covalently crosslinked hydrogel, maximizing cell spreading, and releasing a prescribed amount of an agent or a moiety from a covalently crosslinked hydrogel over a time. In some embodiments, a rate of degradation of a covalently crosslinked hydrogel may be controlled by selecting a molecular weight of a polymer, by selecting a polymer solution concentration, by selecting a specific polymer, by selecting a specific peroxidase, by selecting a specific peroxide, and combinations thereof.

In some embodiments, infusing oxygen and nutrients into a matrix encapsulating cells enhances cell infiltration and soft tissue repair. In some embodiments, a method manufacturing a covalently crosslinked hydrogel of the present invention includes molding channels into a covalently crosslinked hydrogel matrix encapsulating cells to enhance diffusion of oxygen and nutrients and promote cell vascularization.

BRIEF DESCRIPTION OF THE DRAWING

The foregoing and other objects, aspects, features, and advantages of the present disclosure will become more apparent and better understood by referring to the following description taken in conjunction with the accompanying figures in which.

DEFINITIONS

Figure 1:
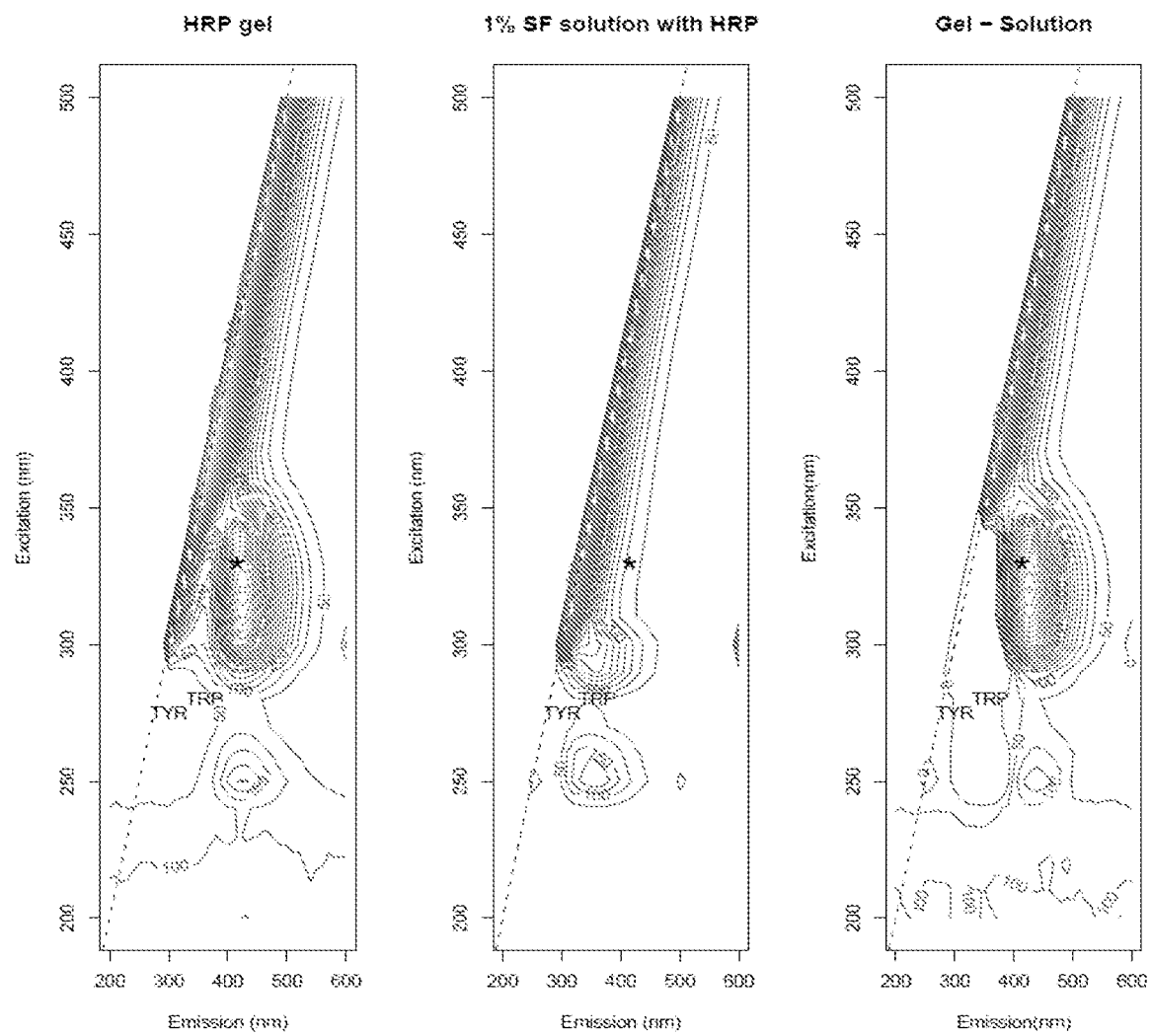
FIG. 1. Fluorescence excitation-emission spectra of 1% concentration gel, 1% solution with horseradish peroxidase (HRP) and the subtraction of the solution from the gel. The appearance of the new peak centered on 415 nm is indicative of tyrosine crosslinking and the formation of dityrosine bonds.

In order for the present disclosure to be more readily understood, certain terms are first defined below. Additional definitions for the following terms and other terms are set forth throughout the specification.

In this application, unless otherwise clear from context, the term "a" may be understood to mean "at least one." As used in this application, the term "or" may be understood to mean "and/or." In this application, the terms "comprising" and "including" may be understood to encompass itemized components or steps whether presented by themselves or together with one or more additional components or steps. Unless otherwise stated, the terms "about" and "approximately" may be understood to permit standard variation as would be understood by those of ordinary skill in the art. Where ranges are provided herein, the endpoints are included. As used in this application, the term "comprise" and variations of the term, such as "comprising" and "comprises," are not intended to exclude other additives, components, integers or steps.

As used in this application, the terms "about" and "approximately" are used as equivalents. Any numerals used in this application with or without about/approximately are meant to cover any normal fluctuations appreciated by one of ordinary skill in the relevant art. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

"Administration": As used herein, the term "administration" refers to the administration of a composition to a subject. Administration may be by any appropriate route. For example, in some embodiments, administration may be bronchial (including by bronchial instillation), buccal, enteral, interdermal, intra-arterial, intradermal, intragastric, intramedullary, intramuscular, intranasal, intraperitoneal, intrathecal, intravenous, intraventricular, mucosal, nasal, oral, rectal, subcutaneous, sublingual, topical, tracheal (including by intratracheal instillation), transdermal, vaginal and vitreal.

"Amino acid": As used herein, the term "amino acid," in its broadest sense, refers to any compound and/or substance that can be incorporated into a polypeptide chain, e.g., through formation of one or more peptide bonds. In some embodiments, an amino acid has the general structure $H_2N$—$C(H)(R)$—$COOH$. In some embodiments, an amino acid is a naturally-occurring amino acid. In some embodiments, an amino acid is a synthetic amino acid; in some embodiments, an amino acid is a D-amino acid; in some embodiments, an amino acid is an L-amino acid. "Standard amino acid" refers to any of the twenty standard L-amino acids commonly found in naturally occurring peptides. "Nonstandard amino acid" refers to any amino acid, other than the standard amino acids, regardless of whether it is prepared synthetically or obtained from a natural source. In some embodiments, an amino acid, including a carboxy- and/or amino-terminal amino acid in a polypeptide, can contain a structural modification as compared with the general structure above. For example, in some embodiments, an amino acid may be modified by methylation, amidation, acetylation, and/or substitution as compared with the general structure. In some embodiments, such modification may, for example, alter the circulating half-life of a polypeptide containing the modified amino acid as compared with one containing an otherwise identical unmodified amino acid. In some embodiments, such modification does not significantly alter a relevant activity of a polypeptide containing the modified amino acid, as compared with one containing an otherwise identical unmodified amino acid. As will be clear from context, in some embodiments, the term "amino acid" is used to refer to a free amino acid; in some embodiments it is used to refer to an amino acid residue of a polypeptide.

"Antibody": As used herein, the term "antibody" refers to a polypeptide that includes canonical immunoglobulin sequence elements sufficient to confer specific binding to a particular target antigen. As is known in the art, intact antibodies as produced in nature are approximately 150 kD tetrameric agents comprised of two identical heavy chain polypeptides (about 50 kD each) and two identical light chain polypeptides (about 25 kD each) that associate with each other into what is commonly referred to as a "Y-shaped" structure. Each heavy chain is comprised of at least four domains (each about 110 amino acids long)—an amino-terminal variable (VH) domain (located at the tips of the Y structure), followed by three constant domains: CH1, CH2, and the carboxy-terminal CH3 (located at the base of the Y's stem). A short region, known as the "switch", connects the heavy chain variable and constant regions. The "hinge" connects CH2 and CH3 domains to the rest of the antibody. Two disulfide bonds in this hinge region connect the two heavy chain polypeptides to one another in an intact antibody. Each light chain is comprised of two domains—an amino-terminal variable (VL) domain, followed by a carboxy-terminal constant (CL) domain, separated from one another by another "switch". Intact antibody tetramers are comprised of two heavy chain-light chain dimers in which the heavy and light chains are linked to one another by a single disulfide bond; two other disulfide bonds connect the heavy chain hinge regions to one another, so that the dimers are connected to one another and the tetramer is formed. Naturally-produced antibodies are also glycosylated, typically on the CH2 domain. Each domain in a natural antibody has a structure characterized by an "immunoglobulin fold" formed from two beta sheets (e.g., 3-, 4-, or 5-stranded sheets) packed against each other in a compressed antiparallel beta barrel. Each variable domain contains three hypervariable loops known as "complement determining regions" (CDR1, CDR2, and CDR3) and four somewhat invariant "framework" regions (FR1, FR2, FR3, and FR4). When natural antibodies fold, the FR regions form the beta sheets that provide the structural framework for the domains, and the CDR loop regions from both the heavy and light chains are brought together in three-dimensional space so that they create a single hypervariable antigen binding site located at the tip of the Y structure. Amino acid sequence comparisons among antibody polypeptide chains have defined two light chain (κ and λ) classes, several heavy chain (e.g., μ, γ, α, ε, δ) classes, and certain heavy chain subclasses (α1, α2, γ1, γ2, γ3, and γ4). Antibody classes (IgA [including IgA1, IgA2], IgD, IgE, IgG [including IgG1, IgG2, IgG3, IgG4], IgM) are defined based on the class of the utilized heavy chain sequences. For purposes of the present invention, in certain embodiments, any polypeptide or complex of polypeptides that includes sufficient immunoglobulin domain sequences as found in natural antibodies can be referred to and/or used as an "antibody", whether such polypeptide is naturally produced (e.g., generated by an organism reacting to an antigen), or produced by recombinant engineering, chemical synthesis, or other artificial system or methodology. In some embodiments, an antibody is monoclonal; in some embodiments, an antibody is monoclonal. In some embodiments, an antibody has constant region sequences that are characteristic of mouse, rabbit, primate, or human antibodies. In some embodiments, an antibody sequence elements are humanized, primatized, chimeric, etc., as is known in the art. Moreover, the term "antibody" as used herein, will be understood to encompass (unless otherwise stated or clear from context) can refer in appropriate embodiments to any of the art-known or developed constructs or formats for capturing antibody structural and functional features in alternative presentation. For example, in some embodiments, the term can refer to bi- or other multi-specific (e.g., zybodies, etc.) antibodies, Small Modular ImmunoPharmaceuticals ("SMIPs™"), single chain antibodies, cameloid antibodies, and/or antibody fragments. In some embodiments, an antibody may lack a covalent modification (e.g., attachment of a glycan) that it would have if produced naturally. In some embodiments, an antibody may contain a covalent modification (e.g., attachment of a glycan, a payload [e.g., a detectable moiety, a therapeutic moiety, a catalytic moiety, etc], or other pendant group [e.g., poly-ethylene glycol, etc]

"Associated": As used herein, the term "associated" typically refers to two or more entities in physical proximity with one another, either directly or indirectly (e.g., via one or more additional entities that serve as a linking agent), to form a structure that is sufficiently stable so that the entities remain in physical proximity under relevant conditions, e.g., physiological conditions. In some embodiments, associated entities are covalently linked to one another. In some embodiments, associated entities are non-covalently linked. In some embodiments, associated entities are linked to one another by specific non-covalent interactions (i.e., by interactions between interacting ligands that discriminate between their interaction partner and other entities present in the context of use, such as, for example. streptavidin/avidin interactions, antibody/antigen interactions, etc.). Alternatively or additionally, a sufficient number of weaker non-covalent interactions can provide sufficient stability for moieties to remain associated. Exemplary non-covalent interactions include, but are not limited to, affinity interactions, metal coordination, physical adsorption, host-guest interactions, hydrophobic interactions, pi stacking interactions, hydrogen bonding interactions, van der Waals interactions, magnetic interactions, electrostatic interactions, dipole-dipole interactions, etc.

"Biocompatible": The term "biocompatible", as used herein, refers to materials that do not cause significant harm to living tissue when placed in contact with such tissue, e.g., in vivo. In certain embodiments, materials are "biocompatible" if they are not toxic to cells. In certain embodiments, materials are "biocompatible" if their addition to cells in vitro results in less than or equal to 20% cell death, and/or their administration in vivo does not induce significant inflammation or other such adverse effects.

"Biodegradable": As used herein, the term "biodegradable" refers to materials that, when introduced into cells, are broken down (e.g., by cellular machinery, such as by enzymatic degradation, by hydrolysis, and/or by combinations thereof) into components that cells can either reuse or dispose of without significant toxic effects on the cells. In certain embodiments, components generated by breakdown of a biodegradable material are biocompatible and therefore do not induce significant inflammation and/or other adverse effects in vivo. In some embodiments, biodegradable polymer materials break down into their component monomers. In some embodiments, breakdown of biodegradable materials (including, for example, biodegradable polymer materials) involves hydrolysis of ester bonds. Alternatively or additionally, in some embodiments, breakdown of biodegradable materials (including, for example, biodegradable polymer materials) involves cleavage of urethane linkages. Exemplary biodegradable polymers include, for example, polymers of hydroxy acids such as lactic acid and glycolic acid, including but not limited to poly(hydroxyl acids), poly(lactic acid)(PLA), poly(glycolic acid)(PGA), poly(lactic-co-glycolic acid)(PLGA), and copolymers with PEG, polyanhydrides, poly(ortho)esters, polyesters, polyurethanes, poly(butyric acid), poly(valeric acid), poly(caprolactone), poly(hydroxyalkanoates, poly(lactide-co-caprolactone), blends and copolymers thereof. Many naturally occurring polymers are also biodegradable, including, for example, proteins such as albumin, collagen, gelatin and prolamines, for example, zein, and polysaccharides such as alginate, cellulose derivatives and polyhydroxyalkanoates, for example, polyhydroxybutyrate blends and copolymers thereof. Those of ordinary skill in the art will appreciate or be able to determine when such polymers are biocompatible and/or biodegradable derivatives thereof (e.g., related to a parent polymer by substantially identical structure that differs only in substitution or addition of particular chemical groups as is known in the art).

"Comparable": The term "comparable", as used herein, refers to two or more agents, entities, situations, sets of conditions, etc. that may not be identical to one another but that are sufficiently similar to permit comparison therebetween so that conclusions may reasonably be drawn based on differences or similarities observed. Those of ordinary skill in the art will understand, in context, what degree of identity is required in any given circumstance for two or more such agents, entities, situations, sets of conditions, etc. to be considered comparable.

"Conjugated": As used herein, the terms "conjugated," "linked," "attached," and "associated with," when used with respect to two or more moieties, means that the moieties are physically associated or connected with one another, either directly or via one or more additional moieties that serves as a linking agent, to form a structure that is sufficiently stable so that the moieties remain physically associated under the conditions in which structure is used, e.g., physiological conditions. Typically the moieties are attached either by one or more covalent bonds or by a mechanism that involves specific binding. Alternately, a sufficient number of weaker interactions can provide sufficient stability for moieties to remain physically associated.

"Corresponding to": As used herein, the term "corresponding to" is often used to designate the position/identity of a residue in a polymer, such as an amino acid residue in a polypeptide or a nucleotide residue in a nucleic acid. Those of ordinary skill will appreciate that, for purposes of simplicity, residues in such a polymer are often designated using a canonical numbering system based on a reference related polymer, so that a residue in a first polymer "corresponding to" a residue at position 190 in the reference polymer, for example, need not actually be the 190th residue in the first polymer but rather corresponds to the residue found at the 190th position in the reference polymer; those of ordinary skill in the art readily appreciate how to identify "corresponding" amino acids, including through use of one or more commercially-available algorithms specifically designed for polymer sequence comparisons.

"Dosage form": As used herein, the term "dosage form" refers to a physically discrete unit of a therapeutic agent for administration to a subject. Each unit contains a predetermined quantity of active agent. In some embodiments, such quantity is a unit dosage amount (or a whole fraction thereof) appropriate for administration in accordance with a dosing regimen that has been determined to correlate with a desired or beneficial outcome when administered to a relevant population (i.e., with a therapeutic dosing regimen).

"Encapsulated": The term "encapsulated" is used herein to refer to substances that are completely surrounded by another material.

"Functional": As used herein, a "functional" biological molecule is a biological molecule in a form in which it exhibits a property and/or activity by which it is characterized. A biological molecule may have two functions (i.e., bi-functional) or many functions (i.e., multifunctional).

"Graft rejection": The term "graft rejection" as used herein, refers to rejection of tissue transplanted from a donor individual to a recipient individual. In some embodiments, graft rejection refers to an allograft rejection, wherein the donor individual and recipient individual are of the same species. Typically, allograft rejection occurs when the donor tissue carries an alloantigen against which the recipient immune system mounts a rejection response.

"High Molecular Weight Polymer": As used herein, the term "high molecular weight polymer" refers to polymers and/or polymer solutions comprised of polymers (e.g., protein polymers, such as silk) having molecular weights of at least about 200 kDa, and wherein no more than 30% of the silk fibroin has a molecular weight of less than 100 kDa. In some embodiments, high molecular weight polymers and/or polymer solutions have an average molecular weight of at least about 100 kDa or more, including, e.g., at least about 150 kDa, at least about 200 kDa, at least about 250 kDa, at least about 300 kDa, at least about 350 kDa or more. In some embodiments, high molecular weight polymers have a molecular weight distribution, no more than 50%, for example, including, no more than 40%, no more than 30%, no more than 20%, no more than 10%, of the silk fibroin can have a molecular weight of less than 150 kDa, or less than 125 kDa, or less than 100 kDa.

"Hydrolytically degradable": As used herein, the term "hydrolytically degradable" is used to refer to materials that degrade by hydrolytic cleavage. In some embodiments, hydrolytically degradable materials degrade in water. In some embodiments, hydrolytically degradable materials degrade in water in the absence of any other agents or materials. In some embodiments, hydrolytically degradable materials degrade completely by hydrolytic cleavage, e.g., in water. By contrast, the term "non-hydrolytically degradable" typically refers to materials that do not fully degrade by hydrolytic cleavage and/or in the presence of water (e.g., in the sole presence of water).

"Hydrophilic": As used herein, the term "hydrophilic" and/or "polar" refers to a tendency to mix with, or dissolve easily in, water.

"Hydrophobic": As used herein, the term "hydrophobic" and/or "non-polar", refers to a tendency to repel, not combine with, or an inability to dissolve easily in, water.

"Low Molecular Weight Polymer": As used herein, the term "low molecular weight polymer" refers to polymers and/or polymer solutions, such as silk, comprised of polymers (e.g., protein polymers) having molecular weights within the range of about 20 kDa-about 400 kDa., In some embodiments, low molecular weight polymers (e.g., protein polymers) have molecular weights within a range between a lower bound (e.g., about 20 kDa, about 30 kDa, about 40 kDa, about 50 kDa, about 60 kDa, or more) and an upper bound (e.g., about 400 kDa, about 375 kDa, about 350 kDa, about 325 kDa, about 300 kDa, or less). In some embodiments, low molecular weight polymers (e.g., protein polymers such as silk) are substantially free of, polymers having a molecular weight above about 400 kD. In some embodiments, the highest molecular weight polymers in provided hydrogels are less than about 300-about 400 kD (e.g., less than about 400 kD, less than about 375 kD, less than about 350 kD, less than about 325 kD, less than about 300 kD, etc). In some embodiments, a low molecular weight polymer and/or polymer solution can comprise a population of polymer fragments having a range of molecular weights, characterized in that: no more than 15% of the total moles of polymer fragments in the population has a molecular weight exceeding 200 kDa, and at least 50% of the total moles of the silk fibroin fragments in the population has a molecular weight within a specified range, wherein the specified range is between about 3.5 kDa and about 120 kDa or between about 5 kDa and about 125 kDa.

"Nucleic acid": As used herein, the term "nucleic acid," in its broadest sense, refers to any compound and/or substance that is or can be incorporated into an oligonucleotide chain. In some embodiments, a nucleic acid is a compound and/or substance that is or can be incorporated into an oligonucleotide chain via a phosphodiester linkage. In some embodiments, "nucleic acid" refers to individual nucleic acid residues (e.g., nucleotides and/or nucleosides). In some embodiments, "nucleic acid" refers to an oligonucleotide chain comprising individual nucleic acid residues. As used herein, the terms "oligonucleotide" and "polynucleotide" can be used interchangeably. In some embodiments, "nucleic acid" encompasses RNA as well as single and/or double-stranded DNA and/or cDNA. Furthermore, the terms "nucleic acid," "DNA," "RNA," and/or similar terms include nucleic acid analogs, i.e., analogs having other than a phosphodiester backbone. For example, the so-called "peptide nucleic acids," which are known in the art and have peptide bonds instead of phosphodiester bonds in the backbone, are considered within the scope of the present invention. The term "nucleotide sequence encoding an amino acid sequence" includes all nucleotide sequences that are degenerate versions of each other and/or encode the same amino acid sequence. Nucleotide sequences that encode proteins and/or RNA may include introns. Nucleic acids can be purified from natural sources, produced using recombinant expression systems and optionally purified, chemically synthesized, etc. Where appropriate, e.g., in the case of chemically synthesized molecules, nucleic acids can comprise nucleoside analogs such as analogs having chemically modified bases or sugars, backbone modifications, etc. A nucleic acid sequence is presented in the 5' to 3' direction unless otherwise indicated. The term "nucleic acid segment" is used herein to refer to a nucleic acid sequence that is a portion of a longer nucleic acid sequence. In many embodiments, a nucleic acid segment comprises at least 3, 4, 5, 6, 7, 8, 9, 10, or more residues. In some embodiments, a nucleic acid is or comprises natural nucleosides (e.g., adenosine, thymidine, guanosine, cytidine, uridine, deoxyadenosine, deoxythymidine, deoxyguanosine, and deoxycytidine); nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages). In some embodiments, the present invention is specifically directed to "unmodified nucleic acids," meaning nucleic acids (e.g., polynucleotides and residues, including nucleotides and/or nucleosides) that have not been chemically modified in order to facilitate or achieve delivery.

"Pharmaceutical composition": As used herein, the term "pharmaceutical composition" refers to an active agent, formulated together with one or more pharmaceutically acceptable carriers. In some embodiments, active agent is present in unit dose amount appropriate for administration in a therapeutic regimen that shows a statistically significant probability of achieving a predetermined therapeutic effect when administered to a relevant population. In some embodiments, pharmaceutical compositions may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream, or foam; sublingually; ocularly; transdermally; or nasally, pulmonary, and to other mucosal surfaces.

"Physiological conditions": The phrase "physiological conditions", as used herein, relates to the range of chemical (e.g., pH, ionic strength) and biochemical (e.g., enzyme concentrations) conditions likely to be encountered in the intracellular and extracellular fluids of tissues. For most tissues, the physiological pH ranges from about 6.8 to about 8.0 and a temperature range of about 20-40 degrees Celsius, about 25-40° C., about 30-40° C., about 35-40° C., about 37° C., atmospheric pressure of about 1. In some embodiments, physiological conditions utilize or include an aqueous environment (e.g., water, saline, Ringers solution, or other buffered solution); in some such embodiments, the aqueous environment is or comprises a phosphate buffered solution (e.g., phosphate-buffered saline).

"Polypeptide": The term "polypeptide" as used herein, refers to a string of at least three amino acids linked together by peptide bonds. In some embodiments, a polypeptide comprises naturally-occurring amino acids; alternatively or additionally, in some embodiments, a polypeptide comprises one or more non-natural amino acids (i.e., compounds that do not occur in nature but that can be incorporated into a polypeptide chain; see, for example, http://www.cco.caltech.edu/~dadgrp/Unnatstruct.gif, which displays structures of non-natural amino acids that have been successfully incorporated into functional ion channels) and/or amino acid analogs as are known in the art may alternatively be employed). For example, a polypeptide can be a protein. In some embodiments, one or more of the amino acids in a polypeptide may be modified, for example, by the addition of a chemical entity such as a carbohydrate group, a phosphate group, a farnesyl group, an isofarnesyl group, a fatty acid group, a linker for conjugation, functionalization, or other modification, etc.

"Polysaccharide": The term "polysaccharide" refers to a polymer of sugars. Typically, a polysaccharide comprises at least three sugars. In some embodiments, a polypeptide comprises natural sugars (e.g., glucose, fructose, galactose, mannose, arabinose, ribose, and xylose); alternatively or additionally, in some embodiments, a polypeptide comprises one or more non-natural amino acids (e.g. modified sugars such as 2'-fluororibose, 2'-deoxyribose, and hexose).

"Porosity": The term "porosity" as used herein, refers to a measure of void spaces in a material and is a fraction of volume of voids over the total volume, as a percentage between 0 and 100%. A determination of a porosity is known to a skilled artisan using standardized techniques, for example mercury porosimetry and gas adsorption (e.g., nitrogen adsorption).

"Protein": As used herein, the term "protein" refers to a polypeptide (i.e., a string of at least two amino acids linked to one another by peptide bonds). Proteins may include moieties other than amino acids (e.g., may be glycoproteins, proteoglycans, etc.) and/or may be otherwise processed or modified. Those of ordinary skill in the art will appreciate that a "protein" can be a complete polypeptide chain as produced by a cell (with or without a signal sequence), or can be a characteristic portion thereof. Those of ordinary skill will appreciate that a protein can sometimes include more than one polypeptide chain, for example linked by one or more disulfide bonds or associated by other means. Polypeptides may contain L-amino acids, D-amino acids, or both and may contain any of a variety of amino acid modifications or analogs known in the art. Useful modifications include, e.g., terminal acetylation, amidation, methylation, etc. In some embodiments, proteins may comprise natural amino acids, non-natural amino acids, synthetic amino acids, and combinations thereof. The term "peptide" is generally used to refer to a polypeptide having a length of less than about 100 amino acids, less than about 50 amino acids, less than 20 amino acids, or less than 10 amino acids. In some embodiments, proteins are antibodies, antibody fragments, biologically active portions thereof, and/or characteristic portions thereof.

"Small molecule": As used herein, the term "small molecule" is used to refer to molecules, whether naturally-occurring or artificially created (e.g., via chemical synthesis), having a relatively low molecular weight and being an organic and/or inorganic compound. Typically, a "small molecule" is monomeric and have a molecular weight of less than about 1500 g/mol. In general, a "small molecule" is a molecule that is less than about 5 kilodaltons (kD) in size. In some embodiments, a small molecule is less than about 4 kD, 3 kD, about 2 kD, or about 1 kD. In some embodiments, the small molecule is less than about 800 daltons (D), about 600 D, about 500 D, about 400 D, about 300 D, about 200 D, or about 100 D. In some embodiments, a small molecule is less than about 2000 g/mol, less than about 1500 g/mol, less than about 1000 g/mol, less than about 800 g/mol, or less than about 500 g/mol. In some embodiments, a small molecule is not a polymer. In some embodiments, a small molecule does not include a polymeric moiety. In some embodiments, a small molecule is not a protein or polypeptide (e.g., is not an oligopeptide or peptide). In some embodiments, a small molecule is not a polynucleotide (e.g., is not an oligonucleotide). In some embodiments, a small molecule is not a polysaccharide. In some embodiments, a small molecule does not comprise a polysaccharide (e.g., is not a glycoprotein, proteoglycan, glycolipid, etc.). In some embodiments, a small molecule is not a lipid. In some embodiments, a small molecule is a modulating agent. In some embodiments, a small molecule is biologically active. In some embodiments, a small molecule is detectable (e.g., comprises at least one detectable moiety). In some embodiments, a small molecule is a therapeutic. Preferred small molecules are biologically active in that they produce a local or systemic effect in animals, preferably mammals, more preferably humans. In certain preferred embodiments, the small molecule is a drug. Preferably, though not necessarily, the drug is one that has already been deemed safe and effective for use by the appropriate governmental agency or body. For example, drugs for human use listed by the FDA under 21 C.F.R. §§ 330.5, 331 through 361, and 440 through 460; drugs for veterinary use listed by the FDA under 21 C.F.R. §§ 500 through 589, incorporated herein by reference, are all considered acceptable for use in accordance with the present application.

"Solution": As used herein, the term "solution" broadly refers to a homogeneous mixture composed of one phase. Typically, a solution comprises a solute or solutes dissolved in a solvent or solvents. It is characterized in that the properties of the mixture (such as concentration, temperature, and density) can be uniformly distributed through the volume. In the context of the present application, therefore, a "silk fibroin solution" refers to silk fibroin protein in a soluble form, dissolved in a solvent, such as water. In some embodiments, silk fibroin solutions may be prepared from a solid-state silk fibroin material (i.e., silk matrices), such as silk films and other scaffolds. Typically, a solid-state silk fibroin material is reconstituted with an aqueous solution, such as water and a buffer, into a silk fibroin solution. It should be noted that liquid mixtures that are not homogeneous, e.g., colloids, suspensions, emulsions, are not considered solutions.

"Stable": The term "stable," when applied to compositions herein, means that the compositions maintain one or more aspects of their physical structure and/or activity over a period of time under a designated set of conditions. In some embodiments, the period of time is at least about one hour; in some embodiments, the period of time is about 5 hours, about 10 hours, about one (1) day, about one (1) week, about two (2) weeks, about one (1) month, about two (2) months, about three (3) months, about four (4) months, about five (5) months, about six (6) months, about eight (8) months, about ten (10) months, about twelve (12) months, about twenty-four (24) months, about thirty-six (36) months, or longer. In some embodiments, the period of time is within the range of about one (1) day to about twenty-four (24) months, about two (2) weeks to about twelve (12) months, about two (2) months to about five (5) months, etc. In some embodiments, the designated conditions are ambient conditions (e.g., at room temperature and ambient pressure). In some embodiments, the designated conditions are physiologic conditions (e.g., in vivo or at about 37° C. for example in serum or in phosphate buffered saline). In some embodiments, the designated conditions are under cold storage (e.g., at or below about 4° C., −20° C., or −70° C.). In some embodiments, the designated conditions are in the dark.

"Substantially": As used herein, the term "substantially", and grammatic equivalents, refer to the qualitative condition of exhibiting total or near-total extent or degree of a characteristic or property of interest. One of ordinary skill in the art will understand that biological and chemical phenomena rarely, if ever, go to completion and/or proceed to completeness or achieve or avoid an absolute result.

"Sustained release": The term "sustained release" is used herein in accordance with its art-understood meaning of release that occurs over an extended period of time. The extended period of time can be at least about 3 days, about 5 days, about 7 days, about 10 days, about 15 days, about 30 days, about 1 month, about 2 months, about 3 months, about 6 months, or even about 1 year. In some embodiments, sustained release is substantially burst-free. In some embodiments, sustained release involves steady release over the extended period of time, so that the rate of release does not vary over the extended period of time more than about 5%, about 10%, about 15%, about 20%, about 30%, about 40% or about 50%. In some embodiments, sustained release involves release with first-order kinetics. In some embodiments, sustained release involves an initial burst, followed by a period of steady release. In some embodiments, sustained release does not involve an initial burst. In some embodiments, sustained release is substantially burst-free release.

"Therapeutic agent": As used herein, the phrase "therapeutic agent" refers to any agent that elicits a desired pharmacological effect when administered to an organism. In some embodiments, an agent is considered to be a therapeutic agent if it demonstrates a statistically significant effect across an appropriate population. In some embodiments, the appropriate population may be a population of model organisms. In some embodiments, an appropriate population may be defined by various criteria, such as a certain age group, gender, genetic background, preexisting clinical conditions, etc. In some embodiments, a therapeutic agent is any substance that can be used to alleviate, ameliorate, relieve, inhibit, prevent, delay onset of, reduce severity of, and/or reduce incidence of one or more symptoms or features of a disease, disorder, and/or condition.

"Treating": As used herein, the term "treating" refers to partially or completely alleviating, ameliorating, relieving, inhibiting, preventing (for at least a period of time), delaying onset of, reducing severity of, reducing frequency of and/or reducing incidence of one or more symptoms or features of a particular disease, disorder, and/or condition. In some embodiments, treatment may be administered to a subject who does not exhibit symptoms, signs, or characteristics of a disease and/or exhibits only early symptoms, signs, and/or characteristics of the disease, for example for the purpose of decreasing the risk of developing pathology associated with the disease. In some embodiments, treatment may be administered after development of one or more symptoms, signs, and/or characteristics of the disease.

DETAILED DESCRIPTION OF CERTAIN EMBODIMENTS

Various embodiments according to the present invention are described in detail herein. In particular, the present invention provides, among other things, hydrogels for cell engineering and/or tissue regeneration and methods related to manufacturing such hydrogels.

While the fiber form of silk is used in suture or textile-based applications, solubilized silk fibroin allows the creation of unique three-dimensional morphologies and materials for applications that range beyond the traditional textile-based applications. Solubilized silk (a silk solution) can be processed to create a range of material formats, including, but not limited to, films, foams, fibers, gels, and sponges. For biomedical applications, one of the material formats that can be used is a hydrogel, which allows for ease of cell infiltration, high water contents, swellability, and/or the ability to control the release of drugs and other therapeutic agents dispersed therein. Hydrogels have been previously formed from silk fibroin, for example, by sonication, vortexing, electrical current, introduction of ions, the addition of PEG and/or poloxamer solutions. Provided herein is a novel method for forming covalently covalently crosslinked silk fibroin hydrogel. The method can allow for highly tunable gelation kinetics and final material properties. In some embodiments, the method can employ all aqueous processing, commonly available reagents, and do not need to rely on expensive or complicated equipment (power supply, sonicator, vortexer, etc.) or volatile chemicals to induce gelation.

In one aspect, the method comprises contacting a silk solution with an enzyme, and inducing gelation of the silk solution comprising the enzyme in the presence of a substrate for the enzyme. In some embodiments, the mixture can be mixed gently to induce gelation. In some embodiments, the method employs a horseradish peroxidase enzyme and hydrogen peroxide to enzymatically crosslink silk fibroins. Without wishing to be bound by theory, the horseradish peroxidase enzyme and hydrogen peroxide can be used to enzymatically crosslink the tyrosine side chains that are found in the native silk fibroin. The gel initiation and gelation rate and/or kinetic properties of the process can be tunable or controlled, for example, depending on concentrations of silk, enzyme (e.g., HRP), and/or substrate for the enzyme (e.g., $H_2O_2$).

This process generates hydrogels with enhanced material properties as compared to a reference silk fibroin hydrogel. In some embodiments, the reference silk fibroin hydrogel can be an existing or conventional silk hydrogel. In some embodiments, the reference silk fibroin hydrogel can be a silk fibroin gel formed by sonication. In some embodiments, the reference silk fibroin hydrogel can be a silk fibroin gel formed by addition of poloxamer. Additionally, gels of the present invention can be highly tunable with mechanical moduli, for example, ranging from approximately 2 kPa up to 300 to 400 kPa with gelation times in the second to minute range.

In some embodiments, hydrogels formed by the method described herein are elastic or highly elastic hydrogels. For example, the hydrogel is able to withstand 100% strain or greater in shear. Additionally or alternatively, the hydrogel is able to withstand 50% strain or greater in compression.

In some embodiments, hydrogels formed by the method described herein can have tunable mechanical properties. For example, hydrogels can have moduli between 200 Pa up to 15 kPa without post-treatment and gels with compressive moduli on the order of 100+ kPa after treatment with methanol.

In some embodiments, hydrogels formed by the method described herein can have unique swelling properties. For example, enzymatic hydrogels described herein can have up to 400% swelling, making them excellent candidates for various applications. In some embodiments, hydrogels with high swelling properties can be used to deliver agents including, but not limited to, drugs, growth factors, antibodies, etc.

In some embodiments, hydrogels formed by the method described herein can be injectable. Without wishing to be bound by theory, low viscosity constituents allow for ease of injection. While silk hydrogel produced in the presence of an electric current as discussed previously (also known as an "e-gel") is elastic, the silk hydrogel requires application of current.

In some embodiments, hydrogels formed by the method described herein can be adhesive. For example, hydrogels can adhere to a surface, e.g., a metal surface such as a stainless steel plate. In some embodiments, adhesive hydrogels can be used as a tissue adhesive.

In some embodiments, hydrogels formed by the method described herein can be optically clear. For example, the hydrogels can exhibit negligible absorbance above 290 nm. Optical clarity allows for various application, e.g., optical machining, cell imaging within and through the gels and/or other applications that other opaque hydrogels do not permit.

In some embodiments, hydrogels formed by the method described herein are biocompatible. For example, such hydrogels have no cytotoxicity or any adverse or negative effects on the cells.

Another aspect provided herein is an elastic silk fibroin hydrogel. The silk fibroin hydrogel comprises tyrosine crosslinks, which can enable beta sheet formation. In some embodiments, kinetics of gelation as well as the plateau modulus can be controlled by adjusting a boiling time and a concentration. In some embodiments, tyrosine covalently crosslinked hydrogels described herein can be resistant to extreme compression and show no plastic deformation at strains of at least 50%. In some embodiments, tyrosine covalently crosslinked gels can have an ability to swell, e.g., up to 400% of its original volume. In some embodiments, the tyrosine covalently crosslinked gels are a true elastomer, rather than a visco-elastic hydrogel. For example, tyrosine covalently crosslinked gels can exhibit negligible energy loss during deformation and nearly fully recover after deformation. For example, some conventional silk fibroin gels typically exhibit plastic deformation between 6-12% strain, while the tyrosine covalently crosslinked gels can be recoverable to compressive strains of at least 50%. In some embodiments, exemplified tyrosine covalently crosslinked hydrogels characterized by the above described properties can be formed from polymer solutions with a low weight percent concentration of polymer, for example, less than 10 wt %.

In biomedical applications, hydrogels have been used as bioactive polymers. The high water content and mechanical response of hydrogels can them desirable and suitable for both cell engineering and tissue restoration applications.

Traditional hydrogels are typically made from synthetic and natural polymers, for example, polyesters, polyurethanes, polyethers, elastin, resilin. Synthetic polymers have also been developed that exhibit high resilience and recovery from both applied tensile and compressive forces. Poly (glycerol sebacate) (PGS) for example has shown utility as a scaffold for engineering vascular, cardiac, and nerve tissues. Additionally, synthetic bioelastomers based on polyurethanes, including for examples variants of poly(ethylene glycol), poly(ε-caprolactone), and poly(vinyl alcohol), modified with degradable segments have also been developed and used for soft tissue, bone, and myocardial repairs. The present disclosure encompasses the recognition of significant drawback, however, that are often associated with traditional hydrogels, both natural and synthetic. For example, although desirable features such as tunable mechanics, cell encapsulation attributes, biocompatibility, biodegradability or elasticity have been reported for certain traditional hydrogels, the present disclosure appreciates that, in general, such traditional hydrogels cannot offer a combination of all of these characteristics.

For example, previously developed hydrogel technologies typically lack certain of the mechanical properties described for hydrogels herein, and/or lack the ability to specifically tune such properties, e.g., via production methodologies. Alternatively or additionally, previously developed hydrogel technologies typically lack certain of the favorable degradation mechanics provided by hydrogels described herein and/or lack the ability to specifically tune such properties. Still further, in many cases, traditional hydrogels fail to display certain degradation properties described for hydrogels provided herein; rapid degradation of such previously-developed hydrogels often limits their use to short term scaffolding. Yet further, in many cases, traditional hydrogel technologies require organic solvents during processing, which can result in toxicity, can interfere with cell or protein encapsulation (and particularly with maintenance of structural and/or functional integrity of encapsulated entities), and cannot resist long term strains when incorporated in vivo.

In many cases, traditional hydrogels form through physical entanglements and hydrogen bonding between hydrophobic domains, resulting in β-sheet formation. β-sheet crystals have been shown to provide structure, strength, and long term stability of hydrogels. But, β-sheet crystals also display brittle behavior, as the crystals prevent long range displacements. Hydrogel technologies described herein provide sophisticated control, selected ion, and/or balance of such properties.

It is worth noting that extracellular matrix (ECM) proteins, purified from native tissues or produced via recombinant DNA methodologies have been used for tissue engineering scaffolds. For example, elastin proteins, provided elastic behavior in many native tissues and have been explored for tissue engineering of soft, elastic matrices. Additionally, recombinant resilin sequences have shown promising mechanical properties. To gain the benefits of proteins as biomaterial matrices, due to their diverse amino acid chemistries for functionalization and biodegradability, recent studies have explored blending with synthetic polymers or other readily available proteins or ECM components. For example, elastin was alloyed with silk, collagen, and poly(lactide-co-glycolide), while resilin was mixed with poly(ethylene glycol) in order to extend utility. Despite the unique properties and biomimetic nature of these protein biomaterials, they are limited in supply and are currently cost prohibitive for larger scale applications.

In some embodiments, the present invention provides covalently crosslinked hydrogels suited for cell growth and tissue regeneration. In some embodiments, the present invention provides method of making and using provided covalently crosslinked hydrogels.

In some embodiments, hydrogels of the present invention are useful for in vivo and in vitro applications requiring soft, tunable, and elastomeric substrates. In some embodiments, covalently crosslinked hydrogels of the present invention provide a surface for cell adhesion. In some embodiments, covalently crosslinked hydrogels of the present invention are configured to provide high adhesion between cells and a covalently crosslinked hydrogel surface. In some embodiments, covalently crosslinked hydrogels of the present invention and surfaces of provided covalently crosslinked hydrogels are configured to adhere cells for cell growth and development. In some embodiments, covalently crosslinked hydrogels of the present invention are configured as a matrix capable of encapsulating cells for introducing cells to a native tissue. In some embodiments, covalently crosslinked hydrogels of the present invention provide a matrix to support encapsulation cells, for applications including, for example in the treatment, such as inducing tissue repair or prevention of a disease, disorder, or condition. In some embodiments, covalently crosslinked hydrogels of the present invention provide encapsulation of cells that show long term survival.

In some embodiments, covalently crosslinked hydrogels of the present invention are adaptable for use with a wide array of cell and/or tissue types in different applications. In some embodiments, covalently crosslinked hydrogels of the present invention are tunable so that mechanical properties of provided covalently crosslinked hydrogels may be tailored to match native tissue for cell growth, tissue engineering or regenerative medicine. In some embodiments, covalently crosslinked hydrogels of the present invention exhibit cell-matrix interactions reflective of highly tunable mechanical properties attributable to such covalently crosslinked hydrogels and methods of forming such covalently crosslinked hydrogels. In some embodiments, covalently crosslinked hydrogels of the present invention, characterized by highly tunable mechanical properties, provide a broad spectrum of elasticity and resilience. In some embodiments, covalently crosslinked hydrogels of the present invention are therefore adaptable to support cell development and tissue regeneration of a wide range of cell and tissue types, including for examples cardiac, skeletal, cartilage, vascular, and/or soft tissue.

In some embodiments, provided covalently crosslinked hydrogels can be functionalized with agents or moieties to support cell growth or development. In some embodiments, provided covalently crosslinked hydrogels can be functionalized with agents or moieties to support incorporation of cells into native tissue. In some embodiments, provided covalently crosslinked hydrogels can be functionalized with agents or moieties useful for treatment of a disease, disorder, or condition. In some embodiments, covalently crosslinked hydrogels of the present invention degrade to release an agent useful for treatment of a disease, disorder, or condition.

In some embodiments, covalently crosslinked hydrogels influence cell shape, size, morphology, movement and/or development/differentiation of cells present therein. In some embodiments, covalently crosslinked hydrogels are useful to configure cells, such as stem cells, for use in a particular application.

In some embodiments, covalently crosslinked hydrogels of the present invention are biocompatible and/or result from aqueous processing, and, therefore, provide for both cell encapsulation and functionalization by moieties and/or agents.

In some embodiments, covalently crosslinked hydrogels of the present invention are biodegradable, and, therefore provide both safe placement and safe release of agents in vivo.

In some embodiments, hydrogels of the present invention provide a platform for electronics, optics and related technological applications. In some embodiment, hydrogels of the present invention possess optical properties and are suitable as optical materials. In some embodiments, an elastomeric nature of hydrogels of the present invention can be exploited to create flexible, biocompatible, three dimensional optical and electronic devices and/or substrates for these technologies. In some embodiments, hydrogels of the present invention possess strong multi-photon absorption so that three-dimensional femtosecond micromachining of electro-optical components for developing novel optical sensors and devices.

Hydrogels

In some embodiments, hydrogels of the present invention are polymer hydrogels (i.e., comprise or consist of polymers). In some embodiments, such polymers are or comprise proteins. In some embodiments, a protein polymer is or comprises silk fibroin. In some embodiments, protein polymers of are selected from the group consisting of agarose, alginate, cellulose, chitin, chitosan, collagen, elastin, gelatin, hyaluronic acid, polydimethylsiloxane, poly(ethylene glycol), polyhydroxyalkanoates, poly(lactide-co-glycolide), pullan, resilin, silk, starch, or combinations thereof.

In some embodiments, a polymer is comprises amino acid phenolic side chains. In some embodiments, a protein polymer solution is a silk fibroin solution. In some embodiments, such as silk, amino acid phenolic side chains are tyrosine.

In some embodiments, hydrogels of the present invention are manufactured from commonly available reagents. In some embodiments, hydrogels of the present invention can be produced without needing volatile chemicals to induce gelation. In some embodiments, hydrogels of the present invention can be produced using all aqueous processing. In some embodiments, hydrogels of the present invention can be produced without the need to rely on expensive or complicated equipment (power supply, sonicator, vortexer, etc.). In some embodiments, hydrogels of the present invention are inexpensive to prepare, easy to prepare, and capable of bulk manufacturing.

In some embodiments, hydrogels of the present invention are prepared under mild, physiologically relevant reaction conditions. In some embodiments, mild aqueous processing is amenable to incorporation of cells and bioactive molecules during formation. In some embodiments, hydrogels provide for ease of infiltration of for example cells, proteins, amino acids, and/or peptides. In some embodiments, the hydrogels of the present invention are biocompatible and biodegradable. In some embodiments, hydrogels are not cytotoxic. In some embodiments, hydrogels are non-immunogenic.

In some embodiment, hydrogels of the present invention are formed from silk fibroin solutions. In some embodiments, a hydrogel of the present invention is formed from a solution having a protein to solvent concentration between about 0.1 wt % to about 30 wt %. In some embodiments, a hydrogel is formed from a protein polymer having a molecular weight between about 10 kDa and about 400 kDa.

In some embodiments, protein polymers for use in accordance with the present invention include amino acid phenolic side chains. In some embodiments, amino acid phenolic side chains are tyrosine. In some embodiments, hydrogels are formed when polymer chains cross-link into networks through chemical or physical means. In some embodiments, hydrogels of the present invention comprise enzymatically covalently crosslinked phenolic amino acid side chain chains. In some embodiments, enzymatically covalently crosslinked amino acid phenolic side chains are dityrosine covalent bonds. In some embodiments, enzymatically covalently crosslinked phenolic amino acid side chain chains are covalently covalently crosslinked dityrosine bonds.

In some embodiments, provided hydrogels are characterized by crystalline structure comprising beta sheet structures and/or hydrogen bonding.

In some embodiments, hydrogels of the present invention are configured to support incorporation of at least one agent. In some embodiments, hydrogels of the present invention control release of drugs and other therapeutic agents dispersed therein.

In some embodiments, hydrogels of the present invention provide ease of incorporation of functional components. In some embodiments, suitable gel functionalization is tunable to specific cell and/or tissue needs. In some embodiments, hydrogels of the present invention are suitable for functionalization or inclusion of components to support needs of cell engineering or tissue remodeling. In some embodiments, channels molded into scaffolds of materials of the present invention support cell infiltration, for example for soft tissue repair and/or replacement by enhancing diffusion of oxygen and nutrients and promoting vascularization in critically sized defects.

In some embodiments, hydrogels of the present invention are biodegradable. In some embodiments biodegradable hydrogels may be safely incorporated in vivo. In some embodiments, hydrogels of the present invention degrade to release of agents incorporated therein. In some embodiments, hydrogels of the present invention are biocompatible and biodegradable. In some embodiments, controlled release of an agent from hydrogels of the present invention may be designed to occur over time, for example, over 12 hours or 24 hours. The time of release may be selected, for example, to occur over a time period of about 12 hours to 24 hours; about 12 hours to 42 hours; or, e.g., about 12 to 72 hours. In another embodiment, release may occur for example on the order of about 1 day to 15 days. The controlled release time may be selected based on the condition treated. For example, longer times may be more effective for wound healing, whereas shorter delivery times may be more useful for some cardiovascular applications. In some embodiments controlled release of an agent from hydrogels of the present invention in vivo may occur, for example, in the amount of about 1 ng to 1 mg/day. In other embodiments, the controlled release may occur in the amount of about 50 ng to 500 ng/day, or, in another embodiment, in the amount of about 100 ng/day. Delivery systems comprising therapeutic agent and a carrier may be formulated that include, for example, 10 ng to 1 mg therapeutic agent, or about 1 µg to 500 µg, or, for example, about 10 µg to 100 µg, depending on the therapeutic application. Moreover, in some embodiments, incorporation of growth factors, and/or incorporation other cell signaling factors provide optimization of cell functions.

In some embodiments, provided hydrogels of the present invention are characterized by high stiffness and superior resilience and elasticity. In some embodiments, provided hydrogels of the present invention are characterized in that they fully recover from large strains or long term cyclic compressions. In some embodiments, provided hydrogels of the present invention are characterized in that they withstand long term stress with negligible changes in modulus and without showing an indication of appreciable changes in mechanical properties, such as a plastic deformation. In some embodiments, provided hydrogels of the present invention are characterized in that they are capable of withstanding repeated strains. In some embodiments, provided hydrogels of the present invention that have been shown to exhibit the above identified characteristics and/or properties are formed from solutions of low weight percent concentration of polymer and of low molecular weight polymers.

In some embodiments, mechanical properties of hydrogels of the present invention are tunable for use in different applications. In some embodiments, hydrogels may be tailored by tunable properties to specific needs, for example, cell engineering or tissue remodeling. In some embodiments, hydrogels include a polymer having enzymatically covalently crosslinked amino acid phenolic side chains. In some embodiments, hydrogels of the present invention are characterized by a storage modulus value between about 50 Pa and about 100 kPa without an indication of a plastic deformation. In some embodiments, hydrogels of the present invention are capable of recovering from a shear strain of at least 100% without showing an indication of a plastic deformation. In some embodiments, hydrogels of the present invention provide a tangent modulus between about 200 Pa to about 400 kPa. In some embodiments, hydrogels of the present invention are capable of recovering from a compressive strain of at least 75% without showing an indication of a plastic deformation.

In some embodiments, hydrogels of the present invention swell up to 400% when exposed to solvents. In some embodiments, hydrogels of the present invention are configured to support cell encapsulation. In some embodiments, hydrogels of the present invention provide direct encapsulation of cells. In some embodiments, encapsulated cells show long term survival. In some embodiments, hydrogels of the present invention support cell survival and proliferation and were well tolerated when implanted in vivo. In some embodiments, hydrogels form a matrix for supporting cell encapsulation.

In some embodiments, hydrogels provide control of cell-matrix interactions. In some embodiments, control of cell-matrix interactions is reflective of varying protein polymer solution concentration and/or modifying gelation conditions. In some embodiments, control of cell matrix interactions influence cell shape. In some embodiments, influencing cell shapes provides for differentiation of cells. In some embodiments, hydrogels of the present invention are biodegradable. In some embodiments, biodegradable hydrogels of the present invention provide controlled delivery of agents. In some embodiments, biomaterials and methods described herein include or comprise biologically degradable hydrogels that carry agents to induce repair and/or remodeling of tissues and cells.

In some embodiments, hydrogels of the present invention are useful for in vivo and in vitro applications requiring highly resilient, tunable, elastomeric substrates. In some embodiments, tunable elastic materials a usable in injectable systems. In some embodiments, hydrogels of the present invention support cell engineering and/or tissue regeneration thereby preventing a disease, disorder or condition and/or inducing repair site.

In some embodiments, enzymatic crosslinking provides in the formation of optically clear gels with negligible absorbance above 350 nm. In some embodiments, the hydrogels of the present invention provide a platform for incorporation of optical or optoelectronic devices. In some embodiments, hydrogels of the present invention are optically clear. In some embodiments, hydrogels of the present invention are configured to be optical materials.

Methods of Forming Hydrogels

In some embodiments, covalently crosslinked hydrogels of the present invention are manufactured as described herein.

In some embodiments, methods of providing, preparing, and/or manufacturing covalently crosslinked hydrogels of the present invention utilize a protein polymer (e.g. silk, such as silk fibroin) solution.

In some embodiments, a covalently crosslinked hydrogel of the present invention is provided, prepared, and/or manufactured by degumming protein polymers, such as a silk, in a solution for example of in $Na_2CO_3$. In some embodiments, such degumming is performed at a temperature within the range of: about 30° C., about 35° C., about 40° C., about 45° C., about 50° C., about 45° C., about 60° C., about 65° C., about 70° C., about 75° C., about 80° C., about 85° C., about 90° C., about 95° C., about 100° C., about 105° C., about 110° C., about 115° C., about at least 120° C. In some embodiments, such degumming is performed at a temperature below about 65° C. In some embodiments, such degumming is performed at a temperature of about 60° C. or less.

In some embodiments, polymers and/or polymer fragments of the present invention are produced having a molecular weight inversely related to a length of boiling time. In some particular embodiments, a covalently crosslinked hydrogel of the present invention is provided, prepared, and/or manufactured from a solution of silk fibroin that has been boiled for at least about 5, 10, 15, 20, 25, 30, 35, 40, 45, 50, 55, 60, 70, 80, 90, 100, 110, 120, 150, 180, 210, 240, 270, 310, 340, 370, 410 minutes or more.

In some embodiments, a covalently crosslinked hydrogel of the present invention is provided, prepared, and/or manufactured from a solution of a protein polymer having a molecular weight in the range of about 20 kD-about 400 kD. In some embodiments, provided, prepared, and/or manufactured covalently crosslinked hydrogels of the present invention are comprised of polymers (e.g., protein polymers) having molecular weights within a range between a lower bound (e.g., about 20 kD, about 30 kD, about 40 kD, about 50 kD, about 60 kD, or more) and an upper bound (e.g., about 400 kD, about 375 kD, about 350 kD, about 325 kD, about 300 kD, or less). In some embodiments, provided, prepared, and/or manufactured covalently crosslinked hydrogels are comprised of polymers (e.g., protein polymers) having a molecular weight around 60 kD.

In some embodiments, provided covalently crosslinked hydrogels are provided, prepared, and/or manufactured from a protein polymer solution, such as a silk fibroin solution of about 0.1 wt % polymer to about 30 wt % polymer. In some embodiments, a covalently crosslinked hydrogel of the present invention is provided, prepared, and/or manufactured from a protein polymer solution, such as a silk fibroin solution that is less than about 30 wt % polymer. In some embodiments, covalently crosslinked hydrogels of the present invention are provided, prepared, and/or manufactured from a protein polymer solution, such as a silk fibroin solution that is less than about 20 wt % polymer. In some embodiments, a covalently crosslinked hydrogel of the present invention is provided, prepared, and/or manufactured from a protein polymer solution, such as a silk fibroin solution that is less than about 10 wt % polymer. In some embodiments, covalently crosslinked hydrogels of the present invention are provided, prepared, and/or manufactured from a protein polymer solution, such as a silk fibroin solution concentration that is less than about 10 wt % polymer, or even that is about 5% wt %, about 4 wt %, about 3 wt %, about 2 wt %, about 1 wt %, about 0.5 wt %, about 0.1 wt % polymer or less.

In some embodiments, provided covalently crosslinked hydrogels are provided, prepared, and/or manufactured from an aqueous solution of protein polymer (e.g., silk polymer) where the solvent is water, PBS and combinations thereof. In some embodiments, a covalently crosslinked hydrogel of the present invention is provided, prepared, and/or manufactured from an aqueous protein polymer solution in a solvent other than PBS. In some embodiments, a covalently crosslinked hydrogel of the present invention is provided, prepared, and/or manufactured from a solution of protein polymer in water. In some embodiments, a covalently crosslinked hydrogel of the present invention is provided, prepared, and/or manufactured from a solution of protein polymer in DMEM. In some embodiments, a covalently crosslinked hydrogel of the present invention is provided, prepared, and/or manufactured from an aqueous protein polymer solution that is not buffered.

In some embodiments, provided covalently crosslinked hydrogels are provided, prepared, and/or manufactured from silk fibers were solubilized in LiBr and then dialyzed against water. In some embodiments, covalently crosslinked hydrogels of the present invention are provided, prepared, and/or manufactured from a silk solution adjusted and/or maintained at a sub-physiological pH. For example, in some embodiments, a covalently crosslinked hydrogel of the present invention is provided, prepared, and/or manufactured from a solution of protein polymer that is adjusted to and/or maintained at a pH near or below about 6. In some embodiments, covalently crosslinked hydrogels are provided, prepared, and/or manufactured from a solution of protein polymer with a pH for instance about 6 or less, or about 5 or less. However, in some alternative embodiments, covalently crosslinked hydrogels are provided, prepared, and/or manufactured from a solution of protein polymer with a pH in a range for example of at least 6, at least 7, at least 8, at least 9, and at least about 10.

In some embodiments, methods of manufacturing covalently crosslinked hydrogels of the present invention include providing, preparing, and/or manufacturing an enzyme solution. In some embodiments, methods of manufacturing covalently crosslinked hydrogels of the present invention include providing, preparing, and/or manufacturing a peroxidase solution. In some embodiments, a peroxidase comprises for example, horseradish peroxidase. In some embodiments, a peroxidase solution comprises animal heme-dependent peroxidase, bromoperoxidase, glutathione peroxidase, haloperoxidase, horseradish peroxidase, lactoperoxidase, myeloperoxidase, thyroid peroxidase, vanadium peroxidase, vanadium containing peroxidases, and combinations thereof. In some embodiments, methods of manufacturing covalently crosslinked hydrogels of the present invention include utilizing a peroxidase at a concentration between about 0.001 mg/mL and about 10 mg/mL.

In some embodiments, methods of manufacturing hydrogels of the present invention includes enzymatically crosslinking amino acid phenolic side chains of the polymer to forms a hydrogel of the present invention. In some embodiments, methods of providing, preparing, and/or manufacturing covalently crosslinked hydrogels of the present invention comprise forming crosslinks utilizing amino acid residue side chains (e.g., phenolic side chains) present within polymers (e.g., protein polymers). In some embodiments, methods of providing, preparing, and/or manufacturing covalently crosslinked hydrogels of the present invention comprise forming crosslinks via tyrosine residues to form dityrosine covalent bonds.

In some embodiments, manufacturing covalently crosslinked hydrogels of the present invention comprises contacting a silk solution with an enzyme. In some embodiments, a method of providing, preparing, and/or manufacturing a covalently crosslinked hydrogel in accordance with the present invention comprises enzymatically introducing crosslinks. In some embodiments, a method of manufacturing covalently crosslinked hydrogels of the present includes combining a polymer solution and a solution of peroxidase.

In some embodiments, inducing a gelation reaction includes adding a polymer and peroxidase solution to a solution of peroxide. In some embodiments, a method of providing, preparing, and/or manufacturing a covalently crosslinked hydrogel in accordance with the present invention comprises introducing crosslinks with peroxidase (e.g., in the presence of peroxide). In some embodiments, a peroxide is selected from the group consisting of barium peroxide, calcium peroxide, hydrogen peroxide, sodium peroxide, organic peroxides and combinations thereof. In some embodiments, a polymer solution, such as silk, an enzyme, such as peroxidase, and a substrate, such as peroxide are gently mixed to induce crosslinking and gelation.

In some embodiments, a method of providing, preparing, and/or manufacturing a covalently crosslinked hydrogel in accordance with the present invention includes gelation of a polymer (e.g. a protein polymer). In some embodiments, gelation is initiated on combining a polymer solution, a peroxidase solution, and a peroxide. In some embodiments, a gelation reaction forming a hydrogel is complete between about 20 seconds and about 5000 seconds after gelation is induced.

In some embodiments, a method of providing, preparing, and/or manufacturing a covalently crosslinked hydrogel of the present invention includes incorporating one or more functional moieties. In some embodiments, a method of manufacturing a hydrogel of the present invention further includes incorporating at least one agent for delivery. In some embodiments, a step of incorporating occurs prior to gelation. In some embodiments, a step of incorporating occurs after to gelation. For example, in some embodiments, a step of incorporating a biological and/or biologically active agent can occur before or after before gelation is induced, during gelation, or after gelation and/or crosslinking has completed. In some embodiments, a method of manufacturing hydrogels of the present invention includes releasing the at least one agent when a hydrogel of the present invention degrades.

Mechanical Properties of Covalently Crosslinked Hydrogels and Influencing Cell Development Excessive local stress and strain have been implicated in pathological remodeling of tissues. In some embodiments, modulus and mechanical stimulation are critical for proper development of cells and/or tissues. In some embodiments, covalently crosslinked hydrogels of the present invention are capable of withstanding long term strains without appreciable changes in mechanical properties or plastic deformation.

In some embodiments, hydrogels of the present invention and methods of forming hydrogels of the present invention provide matching mechanical properties for cells and/or tissues to a native tissue extracellular matrix (ECM). In some embodiments, hydrogels of the present invention can be fine-tuned to optimize matching to native tissue. In particular, in some embodiments, mechanical properties such as for example, stiffness, elasticity, and or swelling of hydrogels may be fine-tuned to optimize matching.

In some embodiments, covalently crosslinked hydrogels of the present invention are tunable to influence cell size and shape. In some embodiments, cell-matrix interactions are influenced by for examples, protein polymer concentration, protein polymer molecular weight and/or gelation conditions.

In some embodiments, covalently crosslinked hydrogels of the present invention provide a three dimensional cell culture or matrix.

In some embodiments, network strength of the matrix is a function of elasticity. In some embodiments, tunable properties of hydrogels of the present invention influence network strength of a matrix. In some embodiments, tunable mechanics provided by hydrogels of the present invention allow for control of cell-matrix interactions.

In some embodiments, a three dimensional cell culture or matrix supports and may influence cell-specific morphologies, or different morphologies.

In some embodiments, covalently crosslinked hydrogels of the present invention influencing cell size and shape, for example stem cells, providing cell differentiation and maintenance of cell phenotype during cell culture.

In some embodiments, covalently crosslinked hydrogels of the present invention are tunable to influence cell size and shape. In some embodiments, cell-matrix interactions are influenced by for examples, protein polymer concentration, protein polymer molecular weight and/or gelation conditions. In some embodiments, tunable properties of covalently crosslinked hydrogel of the present invention displaying stronger network strength and thereby influencing cell shape. In some embodiments, manipulating cell shape provides differentiation of cell type.

In some embodiments, a covalently crosslinked hydrogel of the present invention for use in encapsulating cells comprises tunable resilience and/or elasticity between a covalently crosslinked hydrogel and a native tissue. In some embodiments, mechanical properties provide an indication of resilience and/or elasticity between a covalently crosslinked hydrogel and a native tissue. In some embodiments, mechanical properties of covalently crosslinked hydrogels of the present invention are capable of being matched, tuned, adjusted, and/or manipulated with mechanical properties of cells of covalently crosslinked hydrogels of the present invention. In some embodiments, mechanical properties include, for example, storage modulus, tangent modulus, plateau modulus, swelling, and/or dynamic modulus.

In some embodiments, matching, tuning, adjusting, and/or manipulating mechanical properties of a covalently crosslinked hydrogel include, for example: selecting a molecular weight of a polymer, selecting a concentration of a polymer solution, selecting a specific polymer, selecting a specific peroxidase, selecting a specific peroxide, selecting a concentration of peroxidase, selecting a concentration of peroxide, or combinations thereof.

In some embodiments, covalently crosslinked hydrogels of the present invention provide tunable mechanical properties yielding a combination elasticity, resiliency, tunable biodegradability, and cell encapsulation features. In some embodiments, mechanical properties of covalently crosslinked hydrogels of the present invention comprise storage modulus, tangent modulus, plateau modulus, dynamic modulus, and capacity to swell. In some embodiments, covalently crosslinked hydrogels of the present invention are characterized by a storage modulus value between about 50 Pa and about 100 kPa without an indication of a plastic deformation. In some embodiments, covalently crosslinked hydrogels of the present invention are capable of recovering from a shear strain of at least 100% without showing an indication of a plastic deformation. In some embodiments, covalently crosslinked hydrogels of the present invention provide a tangent modulus between about 200 Pa to about 400 kPa. In some embodiments, covalently crosslinked hydrogels of the present invention are capable of recovering from a compressive strain of at least 75% without showing an indication of a plastic deformation.

In some embodiments, hydrogels of the present invention fully recover from large strains and/or long term cyclic compressions. In some embodiments, hydrogels of the present invention were exposed to large strains, up to 80% strain. In some embodiments, hydrogels of the present invention were exposed to long term cyclic compressions, 10% strain at a frequency of 0.5 Hz and 3,600 cycles.

In some embodiments, covalently crosslinked hydrogels of the present invention provide tunable mechanical properties by selecting a polymer solution concentration between about 0.1 wt % and about 30 wt %.

Indeed in some embodiments, provided covalently crosslinked hydrogels formed from low weight percent polymer solutions, that is below 10 wt %, surprisingly have exhibited desired properties and/or characteristics in the above mentioned ranges, specifically desired high storage modulus values that prior gels were not able to achieve. The present invention thus identifies the source of a problem with certain other hydrogel technologies in that they typically require a higher weight percent of polymer in solution to achieve desired properties, such as high storage moduli.

In some embodiments, covalently crosslinked hydrogels of the present invention provide tunable mechanical properties by selecting a molecular weight of a polymer, such as silk fibroin between about 10 kDa and about 400 kDa. In some embodiments, molecular weight is variable by adjusting boiling time. In some embodiments, molecular weight is inversely proportional to a boiling time.

In some embodiments, covalently crosslinked hydrogels of the present invention provide tunable mechanical properties by changing a solvent present in a polymer solution, such a silk fibroin solution. In some embodiments, covalently crosslinked hydrogels of the present invention provide tunable mechanical properties by changing a type of amino acid incorporated on the polymer. In some embodiments, covalently crosslinked hydrogels of the present invention provide tunable mechanical properties by changing a type of peroxidase. In some embodiments, covalently crosslinked hydrogels of the present invention provide tunable mechanical properties by changing a peroxidase concentration. In some embodiments, covalently crosslinked hydrogels of the present invention provide tunable mechanical properties by changing a type of peroxide. In some embodiments, covalently crosslinked hydrogels of the present invention provide tunable mechanical properties by changing a peroxide concentration.

In some embodiments, three dimensional cell culture supports are further tunable so that cell-matrix interactions in vivo may be exploited to control integration of the biomaterials following implantation. In some embodiments, suitable hydrogel functionalization supports for examples inclusion of ECM components, incorporation of growth factors and incorporation of other cell signaling factors to optimize cell functions. In some embodiments, molding of channels into scaffolds was advantageous for cell infiltration for soft tissue repair and replacement. In some embodiments, a linear wire array forms channels throughout a scaffold to enhance diffusion of oxygen and nutrients and promote vascularization in critically sized defects. In some embodiments, molding of channels into scaffolds and allowing for implantation of larger scaffolds without concern for necrosis due to diffusion limits. In some embodiments, influencing cell-matrix interactions provides control of a hydrogel degradation rate.

In some embodiments, matching, tuning, adjusting, and/or manipulating mechanical properties of a covalently crosslinked hydrogel of the present invention for use in encapsulating cells and/or influencing cell shape is accomplished by selecting a molecular weight of a polymer. In some embodiments, a molecular weight of a polymer is in a range of molecular weights between about 10 kDa and about 400 kDa.

In some embodiments, matching, tuning, adjusting, and/or manipulating mechanical properties of a covalently crosslinked hydrogel of the present invention for use in encapsulating cells and/or influencing cell shape comprises is accomplished by selecting a polymer solution concentration. In some embodiments, a polymer solution concentration is in a range of concentrations between about 0.1 wt % and about 30 wt %.

In some embodiments, matching, tuning, adjusting, and/or manipulating mechanical properties of a covalently crosslinked hydrogel of the present invention for use in encapsulating cells and/or influencing cell shape comprises is accomplished by selecting a molecular weight of a polymer and selecting a polymer solution concentration.

In some embodiments, a method of providing, preparing, and/or manufacturing a covalently crosslinked hydrogel of the present invention comprises controlling a rate of degradation of a covalently crosslinked hydrogel of the present invention for maintaining a covalently crosslinked hydrogel shape, optimizing infiltration and/or integration of a covalently crosslinked hydrogel, maximizing cell spreading, and releasing a prescribed amount of an agent or a moiety from a covalently crosslinked hydrogel over a time. In some embodiments, a rate of degradation of a covalently crosslinked hydrogel may be controlled by selecting a molecular weight of a polymer, by selecting a polymer solution concentration, by selecting a specific polymer, by selecting a specific peroxidase, by selecting a specific peroxide, and combinations thereof.

In some embodiments, infusing oxygen and nutrients into a matrix encapsulating cells enhances cell infiltration and soft tissue repair. In some embodiments, a method manufacturing a covalently crosslinked hydrogel of the present invention includes molding channels into a covalently crosslinked hydrogel matrix encapsulating cells to enhance diffusion of oxygen and nutrients and promote cell vascularization.

Polymers

In some embodiments, a polymer is natural or synthetic. In some embodiments, a polymer comprises one or more polypeptides or proteins. In some embodiments, degradable polymers known in the art include, for example, certain polyesters, polyanhydrides, polycaptolactone, polyorthoesters, polyphosphazenes, polyphosphoesters, certain polyhydroxyacids, polypropylfumerates, polycaprolactones, polyamides, poly(amino acids), polyacetals, polyethers, biodegradable polycyanoacrylates, biodegradable polyurethanes, poly(glycerol sebacates), elastomeric poly(glycerol sebacates polysaccharides), polypyrrole, polyanilines, polythiophene, polystyrene, polyesters, polyureas, poly(ethylene vinyl acetate), polypropylene, polymethacrylate, polyethylene, polycarbonates, poly(ethylene oxide), polysaccharides, co-polymers, and combinations thereof. For example, specific biodegradable polymers that may be used include but are not limited to polylysine (e.g., poly(L-lysine) ("PLL")), poly(lactic acid) ("PLA"), poly(glycolic acid) ("PGA"), polylactic acid/poly(glycolide-colactide) copolymer ("PLGA"), poly(caprolactone) ("PCL"), poly(lactide-co-glycolide) ("PLG"), poly(lactide-co-caprolactone) ("PLC"), poly(glycolide-co-caprolactone) ("PGC"), poly(styrene sulfonate) ("SPS"), poly(acrylic acid) ("PAA"), linear poly(ethylene imine) ("LPEI"), poly(diallyldimethyl ammonium chloride) ("PDAC"), and poly(allylamine hydrochloride) ("PAH"). Another exemplary degradable polymer is poly(beta-amino esters), which may be suitable for use in accordance with the present application. Those skilled in the art will recognize that this is an exemplary, not comprehensive, list of polymers.

Silks

In some embodiments, a polymer is silk. Silk is a natural protein fiber produced in a specialized gland of certain organisms. Silk production in organisms is especially common in the Hymenoptera (bees, wasps, and ants), and is sometimes used in nest construction. Other types of arthropod also produce silk, most notably various arachnids such as spiders (e.g., spider silk). Silk fibers generated by insects and spiders represent the strongest natural fibers known and rival even synthetic high performance fibers.

Silk has been a highly desired and widely used textile since its first appearance in ancient China (see Elisseeff, "The Silk Roads: Highways of Culture and Commerce," Berghahn Books/UNESCO, New York (2000); see also Vainker, "Chinese Silk: A Cultural History," Rutgers University Press, Piscataway, N.J. (2004)). Glossy and smooth, silk is favored by not only fashion designers but also tissue engineers because it is mechanically tough but degrades harmlessly inside the body, offering new opportunities as a highly robust and biocompatible material substrate (see Altman et al., Biomaterials, 24: 401 (2003); see also Sashina et al., Russ. J. Appl. Chem., 79: 869 (2006)).

Silk is naturally produced by various species, including, without limitation: *Antheraea mylitta*; *Antheraea pernyi*; *Antheraea yamamai*; *Galleria mellonella*; *Bombyx mori*; *Bombyx mandarina*; *Galleria mellonella*; *Nephila clavipes*; *Nephila senegalensis*; *Gasteracantha mammosa*; *Argiope aurantia*; *Araneus diadematus*; *Latrodectus geometricus*; *Araneus bicentenarius*; *Tetragnatha versicolor*; *Araneus ventricosus*; *Dolomedes tenebrosus*; *Euagrus chisoseus*; *Plectreurys tristis*; *Argiope trifasciata*; and *Nephila madagascariensis*.

In general, silk for use in accordance with the present invention may be produced by any such organism, or may be prepared through an artificial process, for example, involving genetic engineering of cells or organisms to produce a silk protein and/or chemical synthesis. In some embodiments of the present invention, silk is produced by the silkworm, *Bombyx mori*.

As is known in the art, silks are modular in design, with large internal repeats flanked by shorter (~100 amino acid) terminal domains (N and C termini). Naturally-occurring silks have high molecular weight (200 to 350 kDa or higher) with transcripts of 10,000 base pairs and higher and >3000 amino acids (reviewed in Omenatto and Kaplan (2010) Science 329: 528-531). The larger modular domains are interrupted with relatively short spacers with hydrophobic charge groups in the case of silkworm silk. N- and C-termini are involved in the assembly and processing of silks, including pH control of assembly. The N- and C-termini are highly conserved, in spite of their relatively small size compared with the internal modules. Table 1, below, provides an exemplary list of silk-producing species and silk proteins:

TABLE 1

An exemplary list of silk-producing species and silk proteins (adopted from Bini et al. (2003), J. Mol. Biol. 335(1): 27-40).

| Accession | Species | Producing gland | Protein |
|---|---|---|---|
| A. Silkworms | | | |
| AAN28165 | *Antheraea mylitta* | Salivary | Fibroin |
| AAC32606 | *Antheraea pernyi* | Salivary | Fibroin |
| AAK83145 | *Antheraea yamamai* | Salivary | Fibroin |
| AAG10393 | *Galleria mellonella* | Salivary | Heavy-chain fibroin (N-terminal) |
| AAG10394 | *Galleria mellonella* | Salivary | Heavy-chain fibroin (C-terminal) |
| P05790 | *Bombyx mori* | Salivary | Fibroin heavy chain precursor, Fib-H, H-fibroin |

TABLE 1-continued

An exemplary list of silk-producing species and silk proteins
(adopted from Bini et al. (2003), J. Mol. Biol. 335(1): 27-40).

| Accession | Species | Producing gland | Protein |
| --- | --- | --- | --- |
| CAA27612 | Bombyx mandarina | Salivary | Fibroin |
| Q26427 | Galleria mellonella | Salivary | Fibroin light chain precursor, Fib-L, L-fibroin, PG-1 |
| P21828 | Bombyx mori | Salivary | Fibroin light chain precursor, Fib-L, L-fibroin |
| B. Spiders | | | |
| P19837 | Nephila clavipes | Major ampullate | Spidroin 1, dragline silk fibroin 1 |
| P46804 | Nephila clavipes | Major ampullate | Spidroin 2, dragline silk fibroin 2 |
| AAK30609 | Nephila senegalensis | Major ampullate | Spidroin 2 |
| AAK30601 | Gasteracantha mammosa | Major ampullate | Spidroin 2 |
| AAK30592 | Argiope aurantia | Major ampullate | Spidroin 2 |
| AAC47011 | Araneus diadematus | Major ampullate | Fibroin-4, ADF-4 |
| AAK30604 | Latrodectus geometricus | Major ampullate | Spidroin 2 |
| AAC04503 | Araneus bicentenarius | Major ampullate | Spidroin 2 |
| AAK30615 | Tetragnatha versicolor | Major ampullate | Spidroin 1 |
| AAN85280 | Araneus ventricosus | Major ampullate | Dragline silk protein-1 |
| AAN85281 | Araneus ventricosus | Major ampullate | Dragline silk protein-2 |
| AAC14589 | Nephila clavipes | Minor ampullate | MiSp1 silk protein |
| AAK30598 | Dolomedes tenebrosus | Ampullate | Fibroin 1 |
| AAK30599 | Dolomedes tenebrosus | Ampullate | Fibroin 2 |
| AAK30600 | Euagrus chisoseus | Combined | Fibroin 1 |
| AAK30610 | Plectreurys tristis | Larger ampule-shaped | Fibroin 1 |
| AAK30611 | Plectreurys tristis | Larger ampule-shaped | Fibroin 2 |
| AAK30612 | Plectreurys tristis | Larger ampule-shaped | Fibroin 3 |
| AAK30613 | Plectreurys tristis | Larger ampule-shaped | Fibroin 4 |
| AAK30593 | Argiope trifasciata | Flagelliform | Silk protein |
| AAF36091 | Nephila madagascariensis | Flagelliform | Fibroin, silk protein (N-terminal) |
| AAF36092 | Nephila madagascariensis | Flagelliform | Silk protein (C-terminal) |
| AAC38846 | Nephila clavipes | Flagelliform | Fibroin, silk protein (N-terminal) |
| AAC38847 | Nephila clavipes | Flagelliform | Silk protein (C-terminal) |

Silk Fibroin

Fibroin is a type of structural protein produced by certain spider and insect species that produce silk. Cocoon silk produced by the silkworm, Bombyx mori, is of particular interest because it offers low-cost, bulk-scale production suitable for a number of commercial applications, such as textile.

Silkworm cocoon silk contains two structural proteins, the fibroin heavy chain (~350 kDa) and the fibroin light chain (~25 kDa), which are associated with a family of non-structural proteins termed sericin, which glue the fibroin brings together in forming the cocoon. The heavy and light chains of fibroin are linked by a disulfide bond at the C-terminus of the two subunits (see Takei, F., Kikuchi, Y., Kikuchi, A., Mizuno, S. and Shimura, K. (1987) 105 J. Cell Biol., 175-180; see also Tanaka, K., Mori, K. and Mizuno, S. 114 J. Biochem. (Tokyo), 1-4 (1993); Tanaka, K., Kajiyama, N., Ishikura, K., Waga, S., Kikuchi, A., Ohtomo, K., Takagi, T. and Mizuno, S., 1432 Biochim. Biophys. Acta., 92-103 (1999); Y Kikuchi, K Mori, S Suzuki, K Yamaguchi and S Mizuno, "Structure of the Bombyx mori fibroin light-chain-encoding gene: upstream sequence elements common to the light and heavy chain," 110 Gene, 151-158 (1992)). The sericins are a high molecular weight, soluble glycoprotein constituent of silk which gives the stickiness to the material. These glycoproteins are hydrophilic and can be easily removed from cocoons by boiling in water.

As used herein, the term "silk fibroin" refers to silk fibroin protein, whether produced by silkworm, spider, or other insect, or otherwise generated (Lucas et al., 13 Adv. Protein Chem., 107-242 (1958)). In some embodiments, silk fibroin is obtained from a solution containing a dissolved silkworm silk or spider silk. For example, in some embodiments, silkworm silk fibroins are obtained, from the cocoon of Bombyx mori. In some embodiments, spider silk fibroins are obtained, for example, from Nephila clavipes. In the alternative, in some embodiments, silk fibroins suitable for use in the invention are obtained from a solution containing a genetically engineered silk harvested from bacteria, yeast, mammalian cells, transgenic animals or transgenic plants. See, e.g., WO 97/08315 and U.S. Pat. No. 5,245,012, each of which is incorporated herein as reference in its entirety.

Thus, in some embodiments, a silk solution is used to fabricate compositions of the present invention contain fibroin proteins, essentially free of sericins. In some embodiments, silk solutions used to fabricate various compositions of the present invention contain the heavy chain of fibroin, but are essentially free of other proteins. In other embodiments, silk solutions used to fabricate various compositions of the present invention contain both the heavy and light chains of fibroin, but are essentially free of other proteins. In certain embodiments, silk solutions used to fabricate various compositions of the present invention comprise both a heavy and a light chain of silk fibroin; in some such embodiments, the heavy chain and the light chain of silk fibroin are linked via at least one disulfide bond. In some embodiments where the heavy and light chains of fibroin are present, they are linked via one, two, three or more disulfide bonds. Although different species of silk-producing organisms, and different types of silk, have different amino acid compositions, various fibroin proteins share certain structural features. A general trend in silk fibroin structure is a sequence of amino acids that is characterized by usually alternating glycine and alanine, or alanine alone. Such configuration allows fibroin molecules to self-assemble into a beta-sheet conformation. These "Alanine-rich" hydrophobic blocks are typically separated by segments of amino acids with bulky side-groups (e.g., hydrophilic spacers).

Silk materials explicitly exemplified herein were typically prepared from material spun by silkworm, Bombyx mori. Typically, cocoons are boiled in an aqueous solution of 0.02 M $Na_2CO_3$, then rinsed thoroughly with water to extract the glue-like sericin proteins. Extracted silk is then dissolved in a solvent, for example, LiBr (such as 9.3 M) solution at room temperature. A resulting silk fibroin solution can then be further processed for a variety of applications as described elsewhere herein.

In some embodiments, polymers refers to peptide chains or polypeptides having an amino acid sequence corresponding to fragments derived from silk fibroin protein or variants thereof. In the context of hydrogels of the present disclosure, silk fibroin fragments generally refer to silk fibroin peptide chains or polypeptides that are smaller than naturally occurring full length silk fibroin counterpart, such that one or more of the silk fibroin fragments within a population or composition are less than 500 kDa, less than 450 kDa, less than 400 kDa, less than 350 kDa, less than 300 kDa, less than 250 kDa, less than 200 kDa, less than 175 kDa, less than 150 kDa, less than 120 kDa, less than 100 kDa, less than 90 kDa, less than 80 kDa, less than 70 kDa, less than 60 kDa, less than 50 kDa, less than 40 kDa, less than 30 kDa, less than 25 kDa, less than 20 kDa, less than 15 kDa, less than 12 kDa, less than 10 kDa, less than 9 kDa, less than 8 kDa, less than 7 kDa, less than 6 kDa, less than 5 kDa, less than 4 kDa, less than 3.5 kDa, less than 3 kDa, less than 2.5 kDa, less than 2 kDa, less than 1.5 kDa, or less than about 1.0 kDa, etc.

In some embodiments, polymers of silk fibroin fragments can be derived by degumming silk cocoons at or close to (e.g., within 5% around) an atmospheric boiling temperature for at least about: 1 minute of boiling, 2 minutes of boiling, 3 minutes of boiling, 4 minutes of boiling, 5 minutes of boiling, 6 minutes of boiling, 7 minutes of boiling, 8 minutes of boiling, 9 minutes of boiling, 10 minutes of boiling, 11 minutes of boiling, 12 minutes of boiling, 13 minutes of boiling, 14 minutes of boiling, 15 minutes of boiling, 16 minutes of boiling, 17 minutes of boiling, 18 minutes of boiling, 19 minutes of boiling, 20 minutes of boiling, 25 minutes of boiling, 30 minutes of boiling, 35 minutes of boiling, 40 minutes of boiling, 45 minutes of boiling, 50 minutes of boiling, 55 minutes of boiling, 60 minutes or longer, including, e.g., at least 70 minutes, at least 80 minutes, at least 90 minutes, at least 100 minutes, at least 110 minutes, at least about 120 minutes or longer. As used herein, the term "atmospheric boiling temperature" refers to a temperature at which a liquid boils under atmospheric pressure.

In some embodiments, hydrogels of the present invention produced from silk fibroin fragments can be formed by degumming silk cocoons in an aqueous solution at temperatures of: about 30° C., about 35° C., about 40° C., about 45° C., about 50° C., about 55° C., about 60° C., about 65° C., about 70° C., about 75° C., about 80° C., about 85° C., about 90° C., about 95° C., about 100° C., about 105° C., about 110° C., about 115° C., about at least 120° C.

In some embodiments, such elevated temperature can be achieved by carrying out at least portion of the heating process (e.g., boiling process) under pressure. For example, suitable pressure under which silk fibroin fragments described herein can be produced are typically between about 10-40 psi, e.g., about 11 psi, about 12 psi, about 13 psi, about 14 psi, about 15 psi, about 16 psi, about 17 psi, about 18 psi, about 19 psi, about 20 psi, about 21 psi, about 22 psi, about 23 psi, about 24 psi, about 25 psi, about 26 psi, about 27 psi, about 28 psi, about 29 psi, about 30 psi, about 31 psi, about 32 psi, about 33 psi, about 34 psi, about 35 psi, about 36 psi, about 37 psi, about 38 psi, about 39 psi, or about 40 psi.

In some embodiments, silk fibroin fragments solubilized prior to gelation. In some embodiments, a carrier can be a solvent or dispersing medium. In some embodiments, a solvent and/or dispersing medium, for example, is water, cell culture medium, buffers (e.g., phosphate buffered saline), a buffered solution (e.g. PBS), polyol (for example, glycerol, propylene glycol, liquid polyethylene glycol, and the like), Dulbecco's Modified Eagle Medium, fetal bovine serum, or suitable combinations and/or mixtures thereof.

In some embodiments, hydrogels are modulated by controlling a silk concentration. In some embodiments, a weight percentage of silk fibroin can be present in the solution at any concentration suited to the need. In some embodiments, an aqueous silk fibroin solution can have silk fibroin at a concentration of about 0.1 wt % to about 95 wt %, 0.1 wt % to about 75 wt %, or 0.1 wt % to about 50 wt %. In some embodiments, the aqueous silk fibroin solution can have silk fibroin at a concentration of about 0.1 wt % to about 10 wt %, about 0.1 wt % to about 5 wt %, about 0.1 wt % to about 2 wt %, or about 0.1 wt % to about 1 wt %. In some embodiments, the silk fibroin solution have silk fibroin at a concentration of about 10 wt % to about 50 wt %, about 20 wt % to about 50 wt %, about 25 wt % to about 50 wt %, or about 30 wt % to about 50 wt %. In some embodiments, a weight percent of silk in solution is about less than 1 wt %, is about less than 1.5 wt %, is about less than 2 wt %, is about less than 2.5 wt %, is about less than 3 wt %, is about less than 3.5 wt %, is about less than 4 wt %, is about less than 4.5 wt %, is about less than 5 wt %, is about less than 5.5 wt %, is about less than 6 wt %, is about less than 6.5 wt %, is about less than 7 wt %, is about less than 7.5 wt %, is about less than 8 wt %, is about less than 8.5 wt %, is about less than 9 wt %, is about less than 9.5 wt %, is about less than 10 wt %, is about less than 11 wt %, is about less than 12 wt %, is about less than 13 wt %, is about less than 14 wt %, is about less than 15 wt %, is about less than 16 wt %, is about less than 17 wt %, is about less than 18 wt %, is about less than 19 wt %, is about less than 20 wt %, is about less than 25 wt %, or is about less than 30 wt %.

In some embodiments, a hydrogel is configured to be injectable. In some embodiments, a viscosity of an injectable composition is modified by using a pharmaceutically acceptable thickening agent. In some embodiments, a thickening agent, for example, is methylcellulose, xanthan gum, carboxymethyl cellulose, hydroxypropyl cellulose, carbomer, or combination thereof. A preferred concentration of the thickener depends upon a selected agent and viscosity for injection.

In some embodiments, hydrogel form a porous matrix or scaffold. For example, the porous scaffold can have a porosity of at least about 10%, at least about 20%, at least about 30%, at least about 40%, at least about 50%, at least about 60%, at least about 70%, at least about 80%, at least about 90%, or higher.

Degradation Properties of Silk-Based Materials

Additionally, as will be appreciated by those of skill in the art, much work has established that researchers have the ability to control the degradation process of silk. According to the present invention, such control can be particularly valuable in the fabrication of electronic components, and particularly of electronic components that are themselves and/or are compatible with biomaterials. Degradability (e.g., bio-degradability) is often essential for biomaterials used in tissue engineering and implantation. The present invention encompasses the recognition that such degradability is also relevant to and useful in the fabrication of silk electronic components.

According to the present invention, one particularly desirable feature of silk-based materials is the fact that they can be programmably degradable. That is, as is known in the art, depending on how a particular silk-based material is prepared, it can be controlled to degrade at certain rates. Degradability and controlled release of a substance from silk-based materials have been published (see, for example, WO 2004/080346, WO 2005/012606, WO 2005/123114, WO 2007/016524, WO 2008/150861, WO 2008/118133, each of which is incorporated by reference herein).

Control of silk material production methods as well as various forms of silk-based materials can generate silk compositions with known degradation properties. For example, using various silk fibroin materials (e.g., microspheres of approximately 2 µm in diameter, silk film, silk hydrogels) entrapped agents such as therapeutics can be loaded in active form, which is then released in a controlled fashion, e.g., over the course of minutes, hours, days, weeks to months. It has been shown that layered silk fibroin coatings can be used to coat substrates of any material, shape and size, which then can be used to entrap molecules for controlled release, e.g., 2-90 days.

Crystalline Silk Materials

As known in the art and as described herein, silk proteins can stack with one another in crystalline arrays. Various properties of such arrays are determined, for example, by the degree of beta-sheet structure in the material, the degree of cross-linking between such beta sheets, the presence (or absence) of certain dopants or other materials. In some embodiments, one or more of these features is intentionally controlled or engineered to achieve particular characteristics of a silk matrix.

Enzymatic Crosslinking

Enzymes

In some embodiments, provided covalently crosslinked hydrogels are generated using an enzyme. In some embodiments, such an enzyme is a lipase, amylase, organophosphate dehydrogenase, ligase, restriction endonuclease, ribonuclease, DNA polymerase, glucose oxidase, laccase, or a combination thereof. In some embodiments, an enzyme is a peroxidase. In some embodiments, a peroxidase is horseradish peroxidase, glutathione peroxidase, thyroid peroxidase, haloperoxidase, myeloperoxidase, animal heme-dependent peroxidase, vanadium bromoperoxidase, lactoperoxidase or combinations thereof.

In some embodiments, an enzyme is utilized in the practice of the present invention in an aqueous solution or in solution with a suitable non-aqueous solvent.

In some embodiments, an enzyme (e.g., a peroxidase) is utilized in a concentration between, for example: about 0.001 mg/mL and about 100 mg/mL, about 0.001 mg/mL and about 90 mg/mL, about 0.001 mg/mL and about 80 mg/mL, about 0.001 mg/mL and about 70 mg/mL, about 0.001 mg/mL and about 60 mg/mL, about 0.001 mg/mL and about 50 mg/mL, about 0.001 mg/mL and about 40 mg/mL, about 0.001 mg/mL and about 30 mg/mL, about 0.001 mg/mL and about 20 mg/mL, about 0.001 mg/mL and about 10 mg/mL, or about 0.001 mg/mL and about 5 mg/mL. In some embodiments, a solution concentration, for example a peroxidase concentration is: less than about 1 mg/mL, less than about 1.5 mg/mL, less than about 2 mg/mL, less than about 2.5 mg/mL, less than about 3 mg/mL, less than about 3.5 mg/mL, less than about 4 mg/mL, less than about 4.5 mg/mL, less than about 5 mg/mL, less than about 5.5 mg/mL, less than about 6 mg/mL, less than about 6.5 mg/mL, less than about 7 mg/mL, less than about 7.5 mg/mL, less than about 8 mg/mL, less than about 8.5 mg/mL, less than about 9 mg/mL, less than about 9.5 mg/mL, less than about 10 mg/mL, less than about 11 mg/mL, less than about 12 mg/mL, less than about 13 mg/mL, less than about 14 mg/mL, less than about 15 mg/mL, less than about 16 mg/mL, less than about 17 mg/mL, less than about 18 mg/mL, less than about 19 mg/mL, or less than about 20 mg/mL.

Enzyme Substrates/Peroxides

In some embodiments, enzymatic crosslinking (e.g., as is used in many embodiments of gelation reactions herein) is induced by addition of an enzyme substrate, e.g., before, after, or together with the enzyme. In some embodiments an enzyme substrate is a peroxide. In some embodiments, a peroxide is hydrogen peroxide, barium peroxide, calcium peroxide, sodium peroxide, organic peroxides or combinations thereof.

In some embodiments, an enzyme substrate (e.g., a peroxide) is utilized in an aqueous solution, or in solution with another suitable solvent. In some embodiments, an enzyme substrate is utilized at a solution, for example, that is between: about 0.01 wt % and about 95 wt %, about 0.01 wt % and about 90 wt %, about 0.01 wt % and about 85 wt %, about 0.01 wt % and about 75 wt %, about 0.01 wt % and about 70 wt %, about 0.01 wt % and about 65 wt %, about 0.01 wt % and about 60 wt %, about 0.01 wt % and about 55 wt %, about 0.01 wt % and about 50 wt %, about 0.01 wt % and about 45 wt %, about 0.01 wt % and about 40 wt %, about 0.01 wt % and about 35 wt %, about 0.01 wt % and about 30 wt %, about 0.01 wt % and about 25 wt %, about 0.01 wt % and about 20 wt %, about 0.01 wt % and about 15 wt %, about 0.01 wt % and about 10 wt %, about 0.01 wt % and about 5 wt %. In some embodiments, a weight percent of peroxide in solution is: about less than 0.05 wt %, about less than 0.1 wt %, about less than 0.5 wt %, about less than 1 wt %, is about less than 1.5 wt %, is about less than 2 wt %, is about less than 2.5 wt %, is about less than 3 wt %, is about less than 3.5 wt %, is about less than 4 wt %, is about less than 4.5 wt %, is about less than 5 wt %, is about less than 5.5 wt %, is about less than 6 wt %, is about less than 6.5 wt %, is about less than 7 wt %, is about less than 7.5 wt %, is about less than 8 wt %, is about less than 8.5 wt %, is about less than 9 wt %, is about less than 9.5 wt %, is about less than 10 wt %, is about less than 11 wt %, is about less than 12 wt %, is about less than 13 wt %, is about less than 14 wt %, is about less than 15 wt %, is about less than 16 wt %, is about less than 17 wt %, is about less than 18 wt %, is about less than 19 wt %, is about less than 20 wt %, 21 wt %, is about less than 22 wt %, is about less than 23 wt %, is about less than 24 wt %, is about less than 25 wt %, is about less than 26 wt %, is about less than 27 wt %, is about less than 28 wt %, is about less than 29 wt %, or is about less than 30 wt %. In some embodiments, an enzyme substrate is utilized at a solution concentration that is comparable to a reference concentration (e.g., as listed above) of a peroxide. In general, a solution concentration is comparable if, when it is utilized, a comparable amount of crosslinking is observed to that observed with the reference substrate (and reference enzyme) under otherwise comparable conditions.

Functional Moieties and/or Agents

In some embodiments, provided hydrogels can comprise one or more (e.g., one, two, three, four, five or more) agents and/or functional moieties (together, "additives"). Without wishing to be bound by a theory additive can provide or enhance one or more desirable properties, e.g., strength, flexibility, ease of processing and handling, biocompatibility, bioresorability, surface morphology, release rates and/or kinetics of one or more active agents present in the composition, and the like. In some embodiments, one or more such additives can be covalently or non-covalently linked with the hydrogel (e.g., with a polymer such as silk fibroin that makes up the hydrogel) and can be integrated homogenously or heterogeneously within the silk composition.

In some embodiments, an additive is or comprises a moiety covalently associated (e.g., via chemical modification or genetic engineering) with a polymer. In some embodiments, an addivity is non-covalently associated with a hydrogel or hydrogel component.

In some embodiments, provided hydrogels comprise additives at a total amount from about 0.01 wt % to about 99 wt %, from about 0.01 wt % to about 70 wt %, from about 5 wt % to about 60 wt %, from about 10 wt % to about 50 wt %, from about 15 wt % to about 45 wt %, or from about 20 wt % to about 40 wt %, of the total silk composition. In some embodiments, ratio of silk fibroin to additive in the composition can range from about 1000:1 (w/w) to about 1:1000 (w/w), from about 500:1 (w/w) to about 1:500 (w/w), from about 250:1 (w/w) to about 1:250 (w/w), from about 200:1 (w/w) to about 1:200 (w/w), from about 25:1 (w/w) to about 1:25 (w/w), from about 20:1 (w/w) to about 1:20 (w/w), from about 10:1 (w/w) to about 1:10 (w/w), or from about 5:1 (w/w) to about 1:5 (w/w).

In some embodiments, provided hydrogels include one or more additives at a molar ratio relative to polymer (i.e., a polymer:additive ratio) of, e.g., at least 1000:1, at least 900:1, at least 800:1, at least 700:1, at least 600:1, at least 500:1, at least 400:1, at least 300:1, at least 200:1, at least 100:1, at least 90:1, at least 80:1, at least 70:1, at least 60:1, at least 50:1, at least 40:1, at least 30:1, at least 20:1, at least 10:1, at least 7:1, at least 5:1, at least 3:1, at least 1:1, at least 1:3, at least 1:5, at least 1:7, at least 1:10, at least 1:20, at least 1:30, at least 1:40, at least 1:50, at least 1:60, at least 1:70, at least 1:80, at least 1:90, at least 1:100, at least 1:200, at least 1:300, at least 1:400, at least 1:500, at least 600, at least 1:700, at least 1:800, at least 1:900, or at least 1:100.

In some embodiments, moiety polymer:additive ratio is, e.g., at most 1000:1, at most 900:1, at most 800:1, at most 700:1, at most 600:1, at most 500:1, at most 400:1, at most 300:1, at most 200:1, 100:1, at most 90:1, at most 80:1, at most 70:1, at most 60:1, at most 50:1, at most 40:1, at most 30:1, at most 20:1, at most 10:1, at most 7:1, at most 5:1, at most 3:1, at most 1:1, at most 1:3, at most 1:5, at most 1:7, at most 1:10, at most 1:20, at most 1:30, at most 1:40, at most 1:50, at most 1:60, at most 1:70, at most 1:80, at most 1:90, at most 1:100, at most 1:200, at most 1:300, at most 1:400, at most 1:500, at most 1:600, at most 1:700, at most 1:800, at most 1:900, or at most 1:1000.

In some embodiments, moiety polymer:additive ratio is, e.g., from about 1000:1 to about 1:1000, from about 900:1 to about 1:900, from about 800:1 to about 1:800, from about 700:1 to about 1:700, from about 600:1 to about 1:600, from about 500:1 to about 1:500, from about 400:1 to about 1:400, from about 300:1 to about 1:300, from about 200:1 to about 1:200, from about 100:1 to about 1:100, from about 90:1 to about 1:90, from about 80:1 to about 1:80, from about 70:1 to about 1:70, from about 60:1 to about 1:60, from about 50:1 to about 1:50, from about 40:1 to about 1:40, from about 30:1 to about 1:30, from about 20:1 to about 1:20, from about 10:1 to about 1:10, from about 7:1 to about 1:7, from about 5:1 to about 1:5, from about 3:1 to about 1:3, or about 1:1.

In some embodiments, provided hydrogels comprise additives, for example, therapeutic, preventative, and/or diagnostic agents.

In some embodiments, an additive is or comprises one or more therapeutic agents. In general, a therapeutic agent is or comprises a small molecule and/or organic compound with pharmaceutical activity (e.g., activity that has been demonstrated with statistical significance in one or more relevant pre-clinical models or clinical settings). In some embodiments, a therapeutic agent is a clinically-used drug. In some embodiments, a therapeutic agent is or comprises an cells, proteins, peptides, nucleic acid analogues, nucleotides, oligonucleotides, nucleic acids (DNA, RNA, siRNA), peptide nucleic acids, aptamers, antibodies or fragments or portions thereof, anesthetic, anticoagulant, anti-cancer agent, inhibitor of an enzyme, steroidal agent, anti-inflammatory agent, anti-neoplastic agent, antigen, vaccine, antibody, decongestant, antihypertensive, sedative, birth control agent, progestational agent, anti-cholinergic, analgesic, anti-depressant, anti-psychotic, β-adrenergic blocking agent, diuretic, cardiovascular active agent, vasoactive agent, anti-glaucoma agent, neuroprotectant, angiogenesis inhibitor, hormones, hormone antagonists, growth factors or recombinant growth factors and fragments and variants thereof, cytokines, enzymes, antibiotics or antimicrobial compounds, antifungals, antivirals, toxins, prodrugs, chemotherapeutic agents, small molecules, drugs (e.g., drugs, dyes, amino acids, vitamins, antioxidants), pharmacologic agents, and combinations thereof.

In some embodiments, provided hydrogels comprise additives, for example, cells. Cells suitable for use herein include, but are not limited to, progenitor cells or stem cells, smooth muscle cells, skeletal muscle cells, cardiac muscle cells, epithelial cells, endothelial cells, urothelial cells, fibroblasts, myoblasts, chondrocytes, chondroblasts, osteoblasts, osteoclasts, keratinocytes, hepatocytes, bile duct cells, pancreatic islet cells, thyroid, parathyroid, adrenal, hypothalamic, pituitary, ovarian, testicular, salivary gland cells, adipocytes, and precursor cells.

In some embodiments, provided hydrogels comprise additives, for example, organisms, such as, a bacterium, fungus, plant or animal, or a virus. In some embodiments, an active agent may include or be selected from neurotransmitters, hormones, intracellular signal transduction agents, pharmaceutically active agents, toxic agents, agricultural chemicals, chemical toxins, biological toxins, microbes, and animal cells such as neurons, liver cells, and immune system cells. The active agents may also include therapeutic compounds, such as pharmacological materials, vitamins, sedatives, hypnotics, prostaglandins and radiopharmaceuticals.

In some embodiments, provided hydrogels comprise additives, for example, antibiotics. Antibiotics suitable for incorporation in hydrogels include, but are not limited to, aminoglycosides (e.g., neomycin), ansamycins, carbacephem, carbapenems, cephalosporins (e.g., cefazolin, cefaclor, cefditoren, cefditoren, ceftobiprole), glycopeptides (e.g., vancomycin), macrolides (e.g., erythromycin, azithromycin), monobactams, penicillins (e.g., amoxicillin, ampicillin, cloxacillin, dicloxacillin, flucloxacillin), polypeptides (e.g., bacitracin, polymyxin B), quinolones (e.g., ciprofloxacin, enoxacin, gatifloxacin, ofloxacin, etc.), sulfonamides (e.g., sulfasalazine, trimethoprim, trimethoprim-sulfamethoxazole (co-trimoxazole)), tetracyclines (e.g., doxycyline, minocycline, tetracycline, etc.), chloramphenicol, lincomycin, clindamycin, ethambutol, mupirocin, metronidazole, pyrazinamide, thiamphenicol, rifampicin, thiamphenicl, dapsone, clofazimine, quinupristin, metronidazole, linezolid, isoniazid, fosfomycin, fusidic acid, β-lactam antibiotics, rifamycins, novobiocin, fusidate sodium, capreomycin, colistimethate, gramicidin, doxycycline, erythromycin, nalidixic acid, and vancomycin. For example, β-lactam antibiotics can be aziocillin, aztreonam, carbenicillin, cefoperazone, ceftriaxone, cephaloridine, cephalothin, moxalactam, piperacillin, ticarcillin and combination thereof.

In some embodiments, provided hydrogels comprise additives, for example, anti-inflammatories. Anti-inflammatory agents may include corticosteroids (e.g., glucocorticoids), cycloplegics, non-steroidal anti-inflammatory drugs (NSAIDs), immune selective anti-inflammatory derivatives (ImSAIDs), and any combination thereof. Exemplary NSAIDs include, but not limited to, celecoxib (Celebrex®); rofecoxib (Vioxx®), etoricoxib (Arcoxia®), meloxicam (Mobic®), valdecoxib, diclofenac (Voltaren®, Cataflam®), etodolac (Lodine®), sulindac (Clinori®), aspirin, alclofenac, fenclofenac, diflunisal (Dolobid®), benorylate, fosfosal, salicylic acid including acetylsalicylic acid, sodium acetylsalicylic acid, calcium acetylsalicylic acid, and sodium salicylate; ibuprofen (Motrin), ketoprofen, carprofen, fenbufen, flurbiprofen, oxaprozin, suprofen, triaprofenic acid, fenoprofen, indoprofen, piroprofen, flufenamic, mefenamic, meclofenamic, niflumic, salsalate, rolmerin, fentiazac, tilomisole, oxyphenbutazone, phenylbutazone, apazone, feprazone, sudoxicam, isoxicam, tenoxicam, piroxicam (Feldene®), indomethacin (Indocin®), nabumetone (Relafen®), naproxen (Naprosyn®), tolmetin, lumiracoxib, parecoxib, licofelone (ML3000), including pharmaceutically acceptable salts, isomers, enantiomers, derivatives, prodrugs, crystal polymorphs, amorphous modifications, co-crystals and combinations thereof.

In some embodiments, provided hydrogels comprise additives, for example, antibodies. Suitable antibodies for incorporation in hydrogels include, but are not limited to, abciximab, adalimumab, alemtuzumab, basiliximab, bevacizumab, cetuximab, certolizumab pegol, daclizumab, eculizumab, efalizumab, gemtuzumab, ibritumomab tiuxetan, infliximab, muromonab-CD3, natalizumab, ofatumumab omalizumab, palivizumab, panitumumab, ranibizumab, rituximab, tositumomab, trastuzumab, altumomab pentetate, arcitumomab, atlizumab, bectumomab, belimumab, besilesomab, biciromab, canakinumab, capromab pendetide, catumaxomab, denosumab, edrecolomab, efungumab, ertumaxomab, etaracizumab, fanolesomab, fontolizumab, gemtuzumab ozogamicin, golimumab, igovomab, imciromab, labetuzumab, mepolizumab, motavizumab, nimotuzumab, nofetumomab merpentan, oregovomab, pemtumomab, pertuzumab, rovelizumab, ruplizumab, sulesomab, tacatuzumab tetraxetan, tefibazumab, tocilizumab, ustekinumab, visilizumab, votumumab, zalutumumab, and zanolimumab.

In some embodiments, provided hydrogels comprise additives, for example, polypeptides (e.g., proteins), including but are not limited to: one or more antigens, cytokines, hormones, chemokines, enzymes, and any combination thereof as an agent and/or functional group. Exemplary enzymes suitable for use herein include, but are not limited to, peroxidase, lipase, amylose, organophosphate dehydrogenase, ligases, restriction endonucleases, ribonucleases, DNA polymerases, glucose oxidase, laccase, and the like.

In some embodiments, provided hydrogels comprise additives, for example, particularly useful for wound healing. In some embodiments, agents useful for wound healing include stimulators, enhancers or positive mediators of the wound healing cascade which 1) promote or accelerate the natural wound healing process or 2) reduce effects associated with improper or delayed wound healing, which effects include, for example, adverse inflammation, epithelialization, angiogenesis and matrix deposition, and scarring and fibrosis.

In some embodiments, provided hydrogels comprise additives, for example, an optically or electrically active agent, including but not limited to, chromophores; light emitting organic compounds such as luciferin, carotenes; light emitting inorganic compounds, such as chemical dyes; light harvesting compounds such as chlorophyll, bacteriorhodopsin, protorhodopsin, and porphyrins; light capturing complexes such as phycobiliproteins; and related electronically active compounds; and combinations thereof.

Nucleic Acids

In some embodiments, provided hydrogels comprise additives, for example, nucleic acid agents. In some embodiments, a hydrogel may release nucleic acid agents. In some embodiments, a nucleic acid agent is or comprises a therapeutic agent. In some embodiments, a nucleic acid agent is or comprises a diagnostic agent. In some embodiments, a nucleic acid agent is or comprises a prophylactic agent.

It would be appreciate by those of ordinary skill in the art that a nucleic acid agent can have a length within a broad range. In some embodiments, a nucleic acid agent has a nucleotide sequence of at least about 40, for example at least about 60, at least about 80, at least about 100, at least about 200, at least about 500, at least about 1000, or at least about 3000 nucleotides in length. In some embodiments, a nucleic acid agent has a length from about 6 to about 40 nucleotides. For example, a nucleic acid agent may be from about 12 to about 35 nucleotides in length, from about 12 to about 20 nucleotides in length or from about 18 to about 32 nucleotides in length.

In some embodiments, nucleic acid agents may be or comprise deoxyribonucleic acids (DNA), ribonucleic acids (RNA), peptide nucleic acids (PNA), morpholino nucleic acids, locked nucleic acids (LNA), glycol nucleic acids (GNA), threose nucleic acids (TNA), and/or combinations thereof.

In some embodiments, a nucleic acid has a nucleotide sequence that is or comprises at least one protein-coding element. In some embodiments, a nucleic acid has a nucleotide sequence that is or comprises at least one element that is a complement to a protein-coding sequence. In some embodiments, a nucleic acid has a nucleotide sequence that includes one or more gene expression regulatory elements (e.g., promoter elements, enhancer elements, splice donor sites, splice acceptor sites, transcription termination sequences, translation initiation sequences, translation termination sequences, etc.). In some embodiments, a nucleic acid has a nucleotide sequence that includes an origin of replication. In some embodiments, a nucleic acid has a nucleotide sequence that includes one or more integration sequences. In some embodiments, a nucleic acid has a nucleotide sequence that includes one or more elements that participate in intra- or inter-molecular recombination (e.g., homologous recombination). In some embodiments, a nucleic acid has enzymatic activity. In some embodiments, a nucleic acid hybridizes with a target in a cell, tissue, or organism. In some embodiments, a nucleic acid acts on (e.g., binds with, cleaves, etc.) a target inside a cell. In some embodiments, a nucleic acid is expressed in a cell after release from a provided composition. In some embodiments, a nucleic acid integrates into a genome in a cell after release from a provided composition.

In some embodiments, nucleic acid agents have single-stranded nucleotide sequences. In some embodiments, nucleic acid agents have nucleotide sequences that fold into higher order structures (e.g., double and/or triple-stranded structures). In some embodiments, a nucleic acid agent is or comprises an oligonucleotide. In some embodiments, a nucleic acid agent is or comprises an antisense oligonucleotide. Nucleic acid agents may include a chemical modification at the individual nucleotide level or at the oligonucleotide backbone level, or it may have no modifications.

In some embodiments of the present invention, a nucleic acid agent is an siRNA agent. Short interfering RNA (siRNA) comprises an RNA duplex that is approximately 19 basepairs long and optionally further comprises one or two single-stranded overhangs. An siRNA may be formed from two RNA molecules that hybridize together, or may alternatively be generated from a single RNA molecule that includes a self-hybridizing portion. It is generally preferred that free 5' ends of siRNA molecules have phosphate groups, and free 3' ends have hydroxyl groups. The duplex portion of an siRNA may, but typically does not, contain one or more bulges consisting of one or more unpaired nucleotides. One strand of an siRNA includes a portion that hybridizes with a target transcript. In certain preferred embodiments of the invention, one strand of the siRNA is precisely complementary with a region of the target transcript, meaning that the siRNA hybridizes to the target transcript without a single mismatch. In other embodiments of the invention one or more mismatches between the siRNA and the targeted portion of the target transcript may exist. In most embodiments of the invention in which perfect complementarity is not achieved, it is generally preferred that any mismatches be located at or near the siRNA termini.

Short hairpin RNA refers to an RNA molecule comprising at least two complementary portions hybridized or capable of hybridizing to form a double-stranded (duplex) structure sufficiently long to mediate RNAi (typically at least 19 base pairs in length), and at least one single-stranded portion, typically between approximately 1 and 10 nucleotides in length that forms a loop. The duplex portion may, but typically does not, contain one or more bulges consisting of one or more unpaired nucleotides. As described further below, shRNAs are thought to be processed into siRNAs by the conserved cellular RNAi machinery. Thus shRNAs are precursors of siRNAs and are, in general, similarly capable of inhibiting expression of a target transcript.

In describing siRNAs it will frequently be convenient to refer to sense and antisense strands of the siRNA. In general, the sequence of the duplex portion of the sense strand of the siRNA is substantially identical to the targeted portion of the target transcript, while the antisense strand of the siRNA is substantially complementary to the target transcript in this region as discussed further below. Although shRNAs contain a single RNA molecule that self-hybridizes, it will be appreciated that the resulting duplex structure may be considered to comprise sense and antisense strands or portions. It will therefore be convenient herein to refer to sense and antisense strands, or sense and antisense portions, of an shRNA, where the antisense strand or portion is that segment of the molecule that forms or is capable of forming a duplex and is substantially complementary to the targeted portion of the target transcript, and the sense strand or portion is that segment of the molecule that forms or is capable of forming a duplex and is substantially identical in sequence to the targeted portion of the target transcript.

For purposes of description, the discussion below may refer to siRNA rather than to siRNA or shRNA. However, as will be evident to one of ordinary skill in the art, teachings relevant to the sense and antisense strand of an siRNA are generally applicable to the sense and antisense portions of the stem portion of a corresponding shRNA. Thus in general the considerations below apply also to shRNAs.

An siRNA agent is considered to be targeted to a target transcript for the purposes described herein if 1) the stability of the target transcript is reduced in the presence of the siRNA or shRNA as compared with its absence; and/or 2) the siRNA or shRNA shows at least about 90%, more preferably at least about 91%, 92%, 93%, 94%, 95%, 96%, 97%, 98%, 99%, or 100% precise sequence complementarity with the target transcript for a stretch of at least about 15, more preferably at least about 17, yet more preferably at least about 18 or 19 to about 21-23 nucleotides; and/or 3) one strand of the siRNA or one of the self-complementary portions of the shRNA hybridizes to the target transcript under stringent conditions for hybridization of small (<50 nucleotide) RNA molecules in vitro and/or under conditions typically found within the cytoplasm or nucleus of mammalian cells. Since the effect of targeting a transcript is to reduce or inhibit expression of the gene that directs synthesis of the transcript, an siRNA, shRNA, targeted to a transcript is also considered to target the gene that directs synthesis of the transcript even though the gene itself (i.e., genomic DNA) is not thought to interact with the siRNA, shRNA, or components of the cellular silencing machinery. Thus in some embodiments, an siRNA, shRNA, that targets a transcript is understood to target the gene that provides a template for synthesis of the transcript.

In some embodiments, an siRNA agent can inhibit expression of a polypeptide (e.g., a protein). Exemplary polypeptides include, but are not limited to, matrix metallopeptidase 9 (MMP-9), neutral endopeptidase (NEP) and protein tyrosine phosphatase 1B (PTP1B).

Growth Factor

In some embodiments, provided hydrogels comprise additives, for example, growth factor. In some embodiments, a hydrogel may release growth factor. In some embodiments, a hydrogel may release multiple growth factors. In some embodiments growth factor known in the art include, for example, adrenomedullin, angiopoietin, autocrine motility factor, basophils, brain-derived neurotrophic factor, bone morphogenetic protein, colony-stimulating factors, connective tissue growth factor, endothelial cells, epidermal growth factor, erythropoietin, fibroblast growth factor, fibroblasts, glial cell line-derived neurotrophic factor, granulocyte colony stimulating factor, granulocyte macrophage colony stimulating factor, growth differentiation factor-9, hepatocyte growth factor, hepatoma-derived growth factor, insulin-like growth factor, interleukins, keratinocyte growth factor, keratinocytes, lymphocytes, macrophages, mast cells, myostatin, nerve growth factor, neurotrophins, platelet-derived growth factor, placenta growth factor, osteoblasts, platelets, proinflammatory, stromal cells, T-lymphocytes, thrombopoietin, transforming growth factor alpha, transforming growth factor beta, tumor necrosis factor-alpha, vascular endothelial growth factor and combinations thereof.

In some embodiments, provided hydrogels comprise additives, for example, that are particularly useful for healing. Exemplary agents useful as growth factor for defect repair and/or healing can include, but are not limited to, growth factors for defect treatment modalities now known in the art or later-developed; exemplary factors, agents or modalities including natural or synthetic growth factors, cytokines, or modulators thereof to promote bone and/or tissue defect healing. Suitable examples may include, but not limited to 1) topical or dressing and related therapies and debriding agents (such as, for example, Santyl® collagenase) and Iodosorb® (cadexomer iodine); 2) antimicrobial agents, including systemic or topical creams or gels, including, for example, silver-containing agents such as SAGs (silver antimicrobial gels), (CollaGUARD™, Innocoll, Inc) (purified type-I collagen protein based dressing), CollaGUARD Ag (a collagen-based bioactive dressing impregnated with silver for infected wounds or wounds at risk of infection), DermaSIL™ (a collagen-synthetic foam composite dressing for deep and heavily exuding wounds); 3) cell therapy or bioengineered skin, skin substitutes, and skin equivalents, including, for example, Dermograft (3-dimensional matrix cultivation of human fibroblasts that secrete cytokines and growth factors), Apligraf® (human keratinocytes and fibroblasts), Graftskin® (bilayer of epidermal cells and fibroblasts that is histologically similar to normal skin and produces growth factors similar to those produced by normal skin), TransCyte (a Human Fibroblast Derived Temporary Skin Substitute) and Oasis® (an active biomaterial that comprises both growth factors and extracellular matrix components such as collagen, proteoglycans, and glycosaminoglycans); 4) cytokines, growth factors or hormones (both natural and synthetic) introduced to the wound to promote wound healing, including, for example, NGF, NT3, BDGF, integrins, plasmin, semaphoring, blood-derived growth factor, keratinocyte growth factor, tissue growth factor, TGF-alpha, TGF-beta, PDGF (one or more of the three subtypes may be used: AA, AB, and B), PDGF-BB, TGF-beta 3, factors that modulate the relative levels of TGFβ3, TGFβ1, and TGFβ2 (e.g., Mannose-6-phosphate), sex steroids, including for example, estrogen, estradiol, or an oestrogen receptor agonist selected from the group consisting of ethinyloestradiol, dienoestrol, mestranol, oestradiol, oestriol, a conjugated oestrogen, piperazine oestrone sulphate, stilboestrol, fosfesterol tetrasodium, polyestradiol phosphate, tibolone, a phytoestrogen, 17-beta-estradiol; thymic hormones such as Thymosin-beta-4, EGF, HB-EGF, fibroblast growth factors (e.g., FGF1, FGF2, FGF7), keratinocyte growth factor, TNF, interleukins family of inflammatory response modulators such as, for example, IL-10, IL-1, IL-2, IL-6, IL-8, and IL-10 and modulators thereof; INFs (INF-alpha, -beta, and -delta); stimulators of activin or inhibin, and inhibitors of interferon gamma prostaglindin E2 (PGE2) and of mediators of the adenosine 3',5'-cyclic monophosphate (cAMP) pathway; adenosine A1 agonist, adenosine A2 agonist or 5) other agents useful for wound healing, including, for example, both natural or synthetic homologues, agonist and antagonist of VEGF, VEGFA, IGF; IGF-1, proinflammatory cytokines, GM-CSF, and leptins and 6) IGF-1 and KGF cDNA, autologous platelet gel, hypochlorous acid (Sterilox®) lipoic acid, nitric oxide synthase3, matrix metalloproteinase 9 (MMP-9), CCT-ETA, alphavbeta6 integrin, growth factor-primed fibroblasts and Decorin, silver containing wound dressings, Xenaderm™, papain wound debriding agents, lactoferrin, substance P, collagen, and silver-ORC, placental alkaline phosphatase or placental growth factor, modulators of hedgehog signaling, modulators of cholesterol synthesis pathway, and APC (Activated Protein C), keratinocyte growth factor, TNF, Thromboxane A2, NGF, BMP bone morphogenetic protein, CTGF (connective tissue growth factor), wound healing chemokines, decorin, modulators of lactate induced neovascularization, cod liver oil, placental alkaline phosphatase or placental growth factor, and thymosin beta 4. In certain embodiments, one, two three, four, five or six agents useful for wound healing may be used in combination. More details can be found in U.S. Pat. No. 8,247,384, the contents of which are incorporated herein by reference.

It is to be understood that agents useful for growth factor for healing (including for example, growth factors and cytokines) above encompass all naturally occurring polymorphs (for example, polymorphs of the growth factors or cytokines). Also, functional fragments, chimeric proteins comprising one of said agents useful for wound healing or a functional fragment thereof, homologues obtained by analogous substitution of one or more amino acids of the wound healing agent, and species homologues are encompassed. It is contemplated that one or more agents useful for wound healing may be a product of recombinant DNA technology, and one or more agents useful for wound healing may be a product of transgenic technology. For example, platelet derived growth factor may be provided in the form of a recombinant PDGF or a gene therapy vector comprising a coding sequence for PDGF.

In some embodiments, provided hydrogels comprise additives, for example, that are particularly useful as diagnostic agents. In some embodiments, diagnostic agents include gases; commercially available imaging agents used in positron emissions tomography (PET), computer assisted tomography (CAT), single photon emission computerized tomography, x-ray, fluoroscopy, and magnetic resonance imaging (MRI); and contrast agents. Examples of suitable materials for use as contrast agents in MRI include gadolinium chelates, as well as iron, magnesium, manganese, copper, and chromium. Examples of materials useful for CAT and x-ray imaging include iodine-based materials.

In some embodiments, provided hydrogels comprise additives, for example, radionuclides that are particularly useful as therapeutic and/or diagnostic agents. Among the radionuclides used, gamma-emitters, positron-emitters, and X-ray emitters are suitable for diagnostic and/or therapy, while beta emitters and alpha-emitters may also be used for therapy. Suitable radionuclides for forming thermally-responsive conjugates in accordance with the invention include, but are not limited to, $^{123}$I, $^{125}$I, $^{130}$I, $^{131}$I, $^{133}$I, $^{135}$I, $^{47}$Sc, $^{72}$As, $^{72}$Se, $^{90}$Y, $^{88}$Y, $^{97}$Ru, $^{100}$Pd, $^{101}$mRh, $^{119}$Sb, $^{128}$Ba, $^{197}$Hg, $^{211}$At, $^{212}$Bi, $^{212}$Pb, $^{109}$Pd, $^{111}$In, $^{67}$Ga, $^{68}$Ga, $^{67}$Cu, $^{75}$Br, $^{77}$Br, $^{99}$mTc, $^{14}$C, $^{13}$N, $^{15}$O, $^{32}$P, $^{33}$P, and $^{18}$F. In some embodiments, a diagnostic agent may be a fluorescent, luminescent, or magnetic moiety.

Fluorescent and luminescent moieties include a variety of different organic or inorganic small molecules commonly referred to as "dyes," "labels," or "indicators." Examples include fluorescein, rhodamine, acridine dyes, Alexa dyes, cyanine dyes, etc. Fluorescent and luminescent moieties may include a variety of naturally occurring proteins and derivatives thereof, e.g., genetically engineered variants. For example, fluorescent proteins include green fluorescent protein (GFP), enhanced GFP, red, blue, yellow, cyan, and sapphire fluorescent proteins, reef coral fluorescent protein, etc. Luminescent proteins include luciferase, aequorin and derivatives thereof. Numerous fluorescent and luminescent dyes and proteins are known in the art (see, e.g., U.S. Patent Application Publication No.: 2004/0067503; Valeur, B., "Molecular Fluorescence: Principles and Applications," John Wiley and Sons, 2002; *Handbook of Fluorescent Probes and Research Products*, Molecular Probes, 9$^{th}$ edition, 2002; and *The Handbook—A Guide to Fluorescent Probes and Labeling Technologies*, Invitrogen, 10$^{th}$ edition, available at the Invitrogen web site; both of which are incorporated herein by reference).

Administration

Hydrogels of the present invention may be administered to a site or subject by any appropriate route.

To give but a few examples, exemplary modes of administration to a subject include, but are not limited to, topical, implant, injection, infusion, spray, instillation, implantation, or ingestion. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion.

EXEMPLIFICATION

The following examples illustrate some embodiments and aspects of the invention. It will be apparent to those skilled in the relevant art that various modifications, additions, substitutions, and the like can be performed without altering the spirit or scope of the invention, and such modifications and variations are encompassed within the scope of the invention as defined in the claims which follow. The following examples do not in any way limit the invention.

Example 1

Preparation of Aqueous Silk Solution

Silk solutions were prepared using the previously established procedure (Rockwood et al., 2011). Briefly, 5 grams of B. mort silkworm cocoons were immersed in 1 L of boiling 0.02 M $Na_2CO_3$ solution for 10, 20, 30 or 60 minutes, subsequently referred to as 10 mb, 20 mb, 30 mb and 60 mb respectively, to remove the sericin protein coating. Degummed fibers were collected and rinsed with distilled water three times, then air-dried. The fibers were solubilized in 9.3 M LiBr (20% w/v) at 60° C. for 4 hours. A volume of 15 mL of this solution was then dialyzed against 1 L of distilled water (water changes after 1, 3, 6, 24, 36, and 48 hours) with a regenerated cellulose membrane (3500 MWCO, Slide-A-Lyzer, Pierce, Rockford, Ill.). The solubilized silk protein solution was then centrifuged twice (9700 RPM, 20 min., 4° C.) to remove insoluble particulates. Protein concentration was then determined by drying a known mass of the silk solution under a hood for 12 hours and assessing the mass of the remaining solids.

Preparation of Enzymatically Covalently Crosslinked Silk Hydrogels:

HRP, type VI (Sigma Aldrich) lyophilized powder was mixed with deionized water to form a stock solution with a concentration of 1 U/µL. The HRP solution was added to the silk solution in a ratio of 10 µL of the HRP stock solution to 1 mL of silk solution. To initiate gelation, 10 µL of 1% hydrogen peroxide solution were added per mL of silk solution and mixed by gentle pipetting prior to setting.

Preparation of Sonicated Silk Hydrogels:

Aqueous silk solution of the appropriate boiling time and concentration was added to a 2 ml Eppendorf tube and sonicated at 30% amplitude for 10 to 20 seconds until it acquired a whitish, opaque appearance. When it reached this point sonication was stopped and the solution was transferred to the instrument or a petri dish to undergo gelation.

Preparation of Poloxamer Silk Hydrogels:

A 20 wt % solution of poloxamer F77 was prepared in distilled water and gently mixed with silk solution in a 1:1 ratio. After mixing, the silk-poloxamer solution was placed in the appropriate instrument for monitoring the gelation kinetics or placed in a petri dish and allowed to gel for future characterization.

Structural Analysis:

Enzymatically covalently crosslinked hydrogel gel samples were evaluated using Fourier Transform Infrared, Attenuated Total Reflectance Spectroscopy (FTIR) and Fluorescence Spectroscopy in an attempt to determine hydrogel conformation and structure. To perform FTIR samples of hydrogel and silk solution mixed with HRP were dried at room temperature in a hood for 12 hours. Spectra were then recorded from 600-4,000 $cm^{-1}$ using 32 co-added scans at a resolution of 4 $cm^{-1}$ and subjected to ATR correction using JASCO Spectra Analysis software. To assess the intrinsic fluorescence of the solution and hydrogels, 1.5 ml of 1 wt % silk solution was pipetted into a 3 mm path length quartz cuvette and an excitation-emission matrix was recorded from 200 nm to 500 nm in 10 nm increments at an intensity of 700 V using a 2.5 nm slit width to avoid saturation. The silk solution was then rinsed from the cuvette and 1.5 mL of new solution, with HRP and $H_2O_2$ was mixed and pipetted into the cuvette. This solution, with initiator, was allowed to gel for 2 hours at room temperature and another excitation-emission spectra was taken.

Rheological Assessment:

Rheological measurements were conducted on the enzymatically covalently crosslinked hydrogels to determine the gelation time and mechanical strength of the gels. All rheology was carried out on a TA Instruments ARES-LS20 rheometer using a 25 mm stainless steel conical plate (angle: 0.0994 rad) and a temperature controlled peltier plate set to 37° C. Briefly, gels were mixed by gentle pipetting and 420 µL of solution was loaded under the geometry. Prior to gelation, the geometry was lowered to the specified gap and oil was placed around the outside edge of the cone to prevent water evaporation. A dynamic time sweep was conducted at a frequency of 1 Hz (6.283 rad/sec) and 1% strain for 4,000 seconds or until the sample had reached a plateau modulus, whichever occurred first. Following gelation, dynamic strain and frequency sweeps were carried out on the gels to ensure that measurements occurred within the viscoelastic regime and to assess the elasticity and relaxation times of the hydrogels. Silk solutions boiled for 10, 20, 30, and 60 minutes respectively were tested at concentrations of 3% and 5%.

Adhesion Testing:

Gels were observed to exhibit good adhesive capabilities during rheological measurements, prompting and analysis of these properties. Adhesion testing was carried out on a TA Instruments RSA3 Dynamic Mechanical Analyzer between stainless steel plates of 15 mm and 25 mm diameter for the upper and lower plates respectively. Gel solutions of 20 mb, 5% silk solution were mixed via gentle pipetting and loaded onto the parallel plate. Prior to gelation, the geometry was lowered to the specified gap and oil was placed around the upper plate to prevent water evaporation. The gels were enclosed in a temperature controlled oven set to 37° C. and allowed to set for 30 minutes. Following gelation, the temperature controlled oven was removed, and the upper parallel plate was raised at a constant rate of 0.5 mm per second until sample failure.

Silk Swelling and Methanol Treatment:

In order to assess the swelling properties of the enzymatically covalently crosslinked hydrogels, 8 mm diameter samples, approximately 3 mm in height, were punched out of a large film of hydrogel. Silk used for casting was boiled for 20 minutes and was at a concentration of 5%, was mixed with HRP and $H_2O_2$ and allowed to gel overnight at 4° C. Subsequent to punching out the individual samples, the silk gels were then either left over night in air, in water, or in 50% methanol solution. The height and diameter of the silk hydrogels were measured in order to determine the extent of swelling or shrinking as a result of the treatments. Alternately, silk hydrogels of 8 mm diameter and 3.5 mm height were massed on an analytical balance, placed in deionized water for 24 hours. After soaking, the gels were removed from the water, gently wiped with an absorbent cloth to remove surface water, and remassed. Swelling was calculated as the hydrated mass divided by the original mass.

Hydrogel Cyclic Compression Testing:

Unconfined compression tests were conducted to assess the mechanical properties of the silk hydrogels as well as the recovery following multiple compression cycles. 5% solutions of silk, boiled for 20 minutes, were used for the cyclic compression testing. Enzymatically covalently crosslinked silk hydrogels, of 8 mm diameter and 3.5 mm thickness, were punched out from a sample cast in a petri dish. Samples were loaded in a TA Instruments RSA3 Dynamic Mechanical Analyzer between stainless steel parallel plates. The upper plate was lowered until a compression force of 0.5 g was registered by the machine and oil was gently placed around the sample to prevent water evaporation during testing. Samples under went four loading and unloading cycles, during which the sample was compressed or unloaded respectively at a constant strain rate of 0.1667%. Each respective loading and unloading period lasted 90 seconds. Methanol treated and water swollen hydrogels were also subjected to cyclic compression testing under similar conditions. The respective loading and unloading periods for the water swollen gels lasted 90 seconds, while those for the methanol treated gels lasted only 30 seconds due to force limitations of the testing equipment. In order to assess the stability of the gels over numerous cycles, a sample was tested in cyclic compression for two hours at a frequency of 0.5 Hz and 10% strain while recording the storage and loss moduli.

Figure 2:
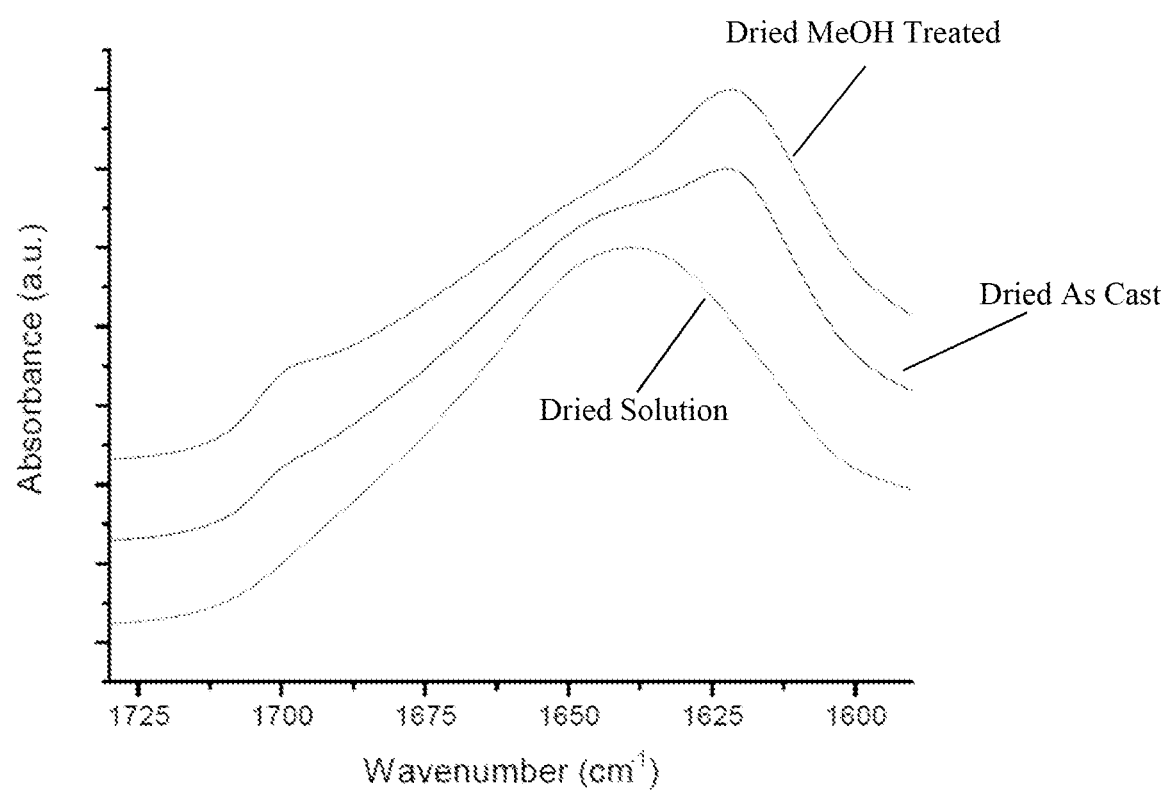
FIG. 2. Fourier Transform Infra-Red (FTIR) spectra of dried silk solution with HRP, dried gel and dried methanol treated gel. The broad peak of the dried solution around 1640 $cm^{-1}$ is indicative of a random coil amorphous conformation. The depression of this peak and occurrence of a new peak centered on 1620 $cm^{-1}$ suggests that the tyrosine crosslinks enable beta sheet formation, and that the gel can be further crystallized through treatment with methanol.

Mechanism of Gelation and Structural Characterization:

Evaluation of the fluorescence and FTIR data indicate that the gel structure formed by enzymatically crosslinking the silk fibroin solution is a result of covalent binding between tyrosine side chains and a subsequent formation of beta sheet structures. FIG. 1 shows the excitation-emission matrix (EEM) of a 1% silk gel, a 1% silk solution with HRP added and the subtraction of the two EEM's. These indicate the formation of dityrosine bonds, as evidenced by the appearance of a peak centered on 415 nm in the emission spectra of the gelled sample (Harms et al., 1997). The existence of these covalent crosslinks generates a fundamentally different hydrogel from the more typical silk gels that rely on weaker hydrogen bonds for formation. In addition to the covalent linkage between tyrosine side chains, there is evidence of hydrogen bonding and formation of beta sheet following gelation. This is shown in FIG. 2, where the FTIR spectra of a dried gel sample exhibits an amide I spectra characteristic of high beta sheet content, with a pronounced peak at 1620 cm$^{-1}$. This is in contrast to the silk and HRP solution that exhibits a broad peak centered on 1640 cm$^{-1}$, indicative of a primarily random coil, amorphous sample. This suggests that the tyrosine crosslinks align the fibroin molecules in a manner that localizes the domains involved in beta sheet formation, allowing the hydrogen bonding to occur without the need for additional treatments to induce crystallization. However, the application of methanol results in a higher degree of crystallinity as evidenced by the reduced intensity of the spectra in the 1640 cm$^{-1}$ region.

Figure 3:
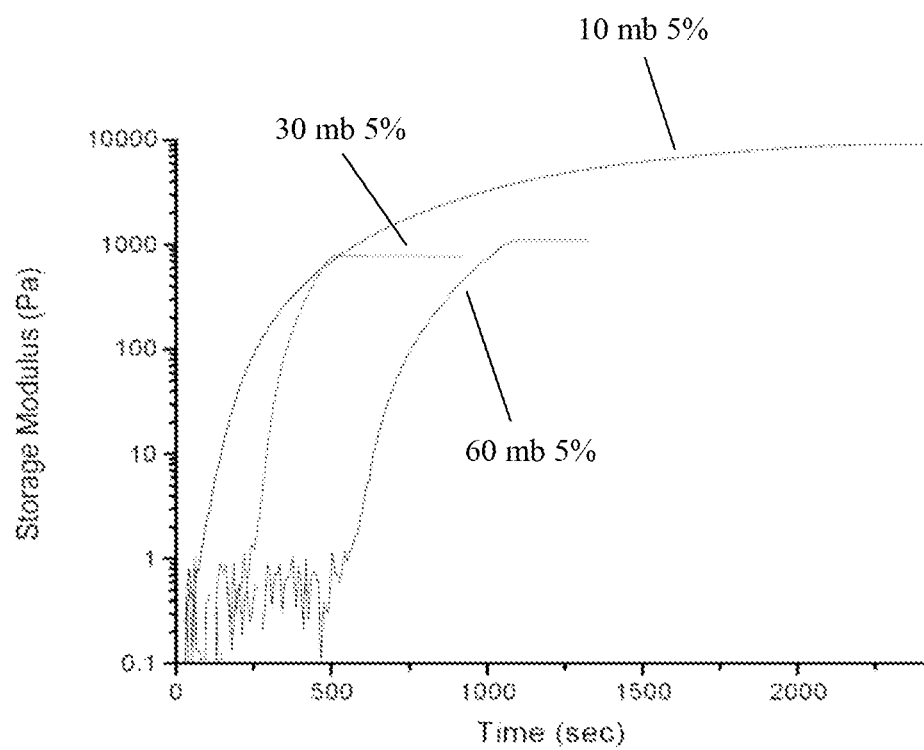
FIG. 3. Development of hydrogel storage modulus over time for silk solutions of 10 mb, 30 mb and 60 mb at a 5 wt % concentration.
Figure 4:
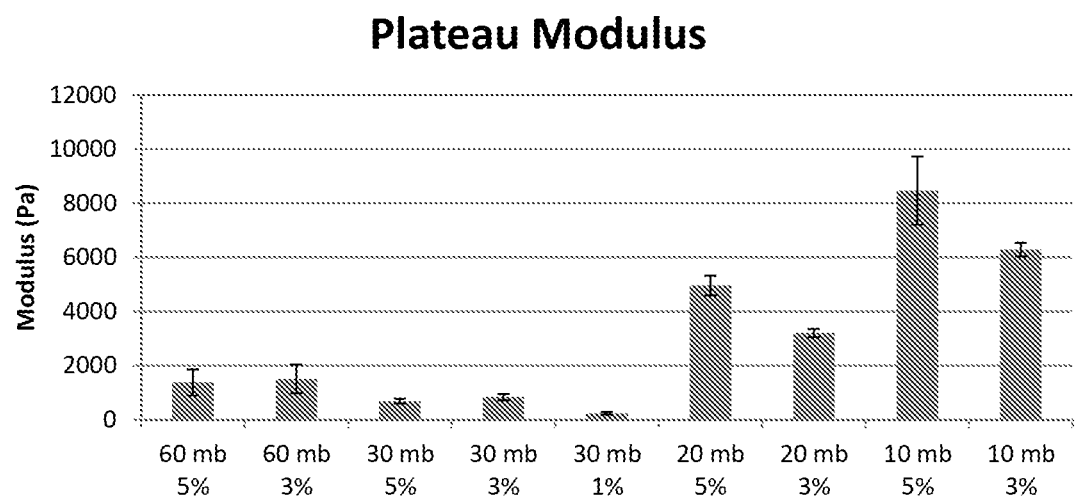
FIG. 4. Plateau modulus after completion of gelation reactions as a function of boiling time and concentration.
Figure 5:
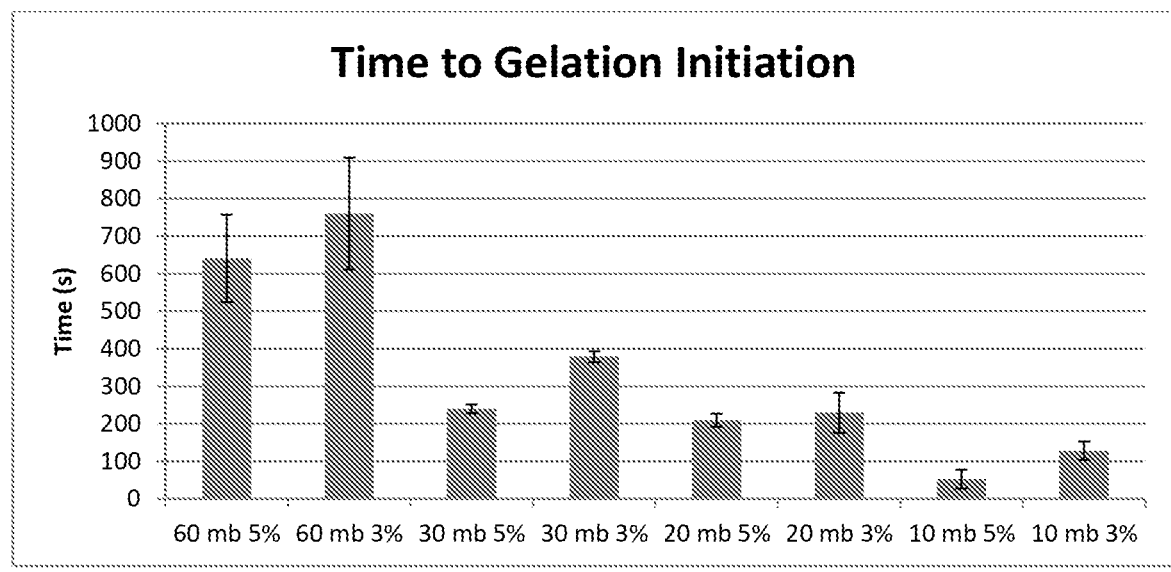
FIG. 5. Time after addition of the hydrogen peroxide ($H_2O_2$) for the initiation of gelation reactions as a function of boiling time and concentration.
Figure 6:
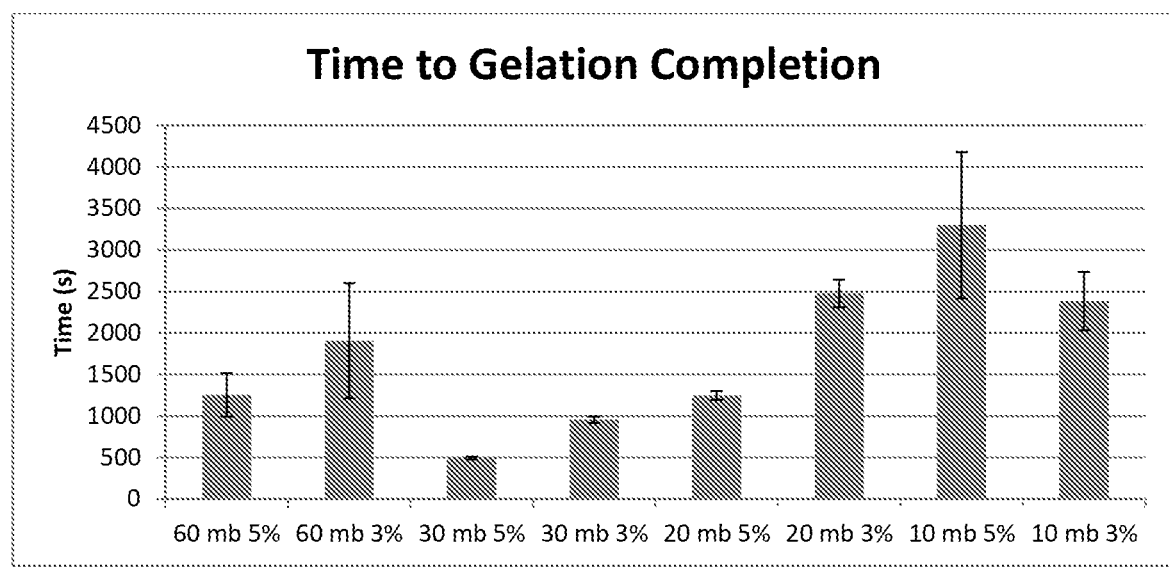
FIG. 6. Time after addition of the hydrogen peroxide for the completion of the gelation reaction as a function of boiling time and concentration.

Rheological Assessment:

The kinetics of gelation and shear properties of the enzymatically linked silk hydrogels were assessed using rheology. FIG. 3 shows representative curves of storage modulus development for several different boiling times at a concentration of 5%, indicating that kinetics of gelation as well as the plateau modulus can be controlled by adjusting the boiling time and concentration. Additional control over kinetics and final material properties can likely be found by adjusting the stoichiometry of the silk-HRP-H$_2$O$_2$ solutions to find optimal ratios. FIG. 4, FIG. 5, and FIG. 6 combine the data extracted from numerous kinetic experiments and include the final plateau modulus, the time to gelation initiation and the time for the completion of the gelation reactions. The data indicates the large range of kinetics and moduli that can be achieved using this systems with gelation times from 500 to 3300 seconds and as cast moduli from 230 Pa to 8.5 kPa. The range of kinetics and moduli can be varied by different boiling/degumming times of silk cocoons, and/or concentrations of the silk fibroin solutions. According, the range of kinetics and moduli can be smaller or larger than as described herein.

Figure 7:
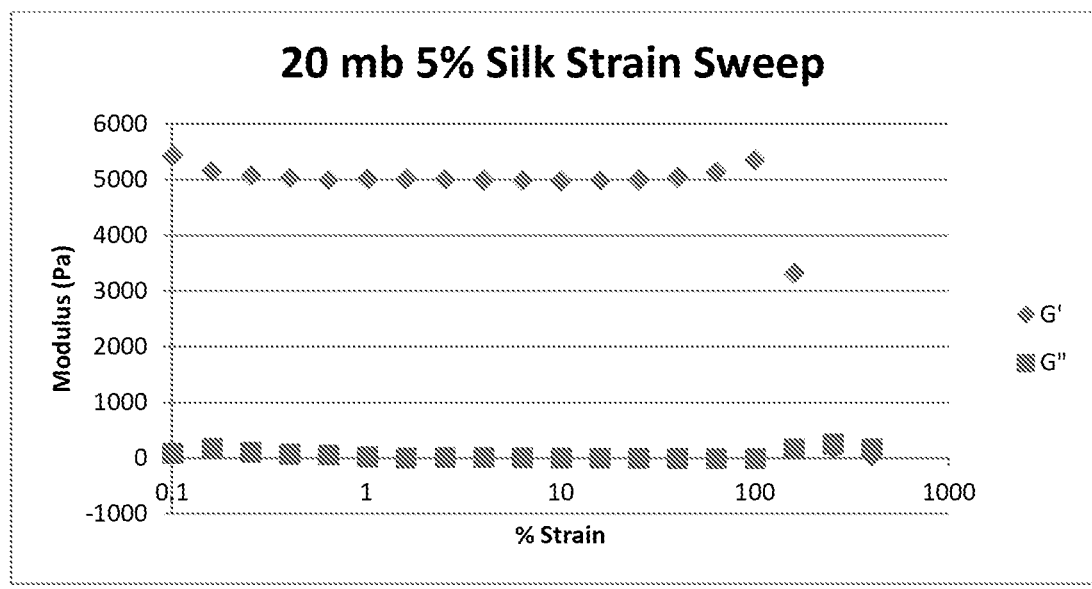
FIG. 7. Strain sweep of a representative 20 mb, 5% concentration gel indicating that it can withstand strains on the order of 100% without plastic deformation.

Following the completion of the gelation reaction and prior to demounting of the samples, the hydrogels were subjected to strain sweeps to assess their ability to resist plastic deformation. A representative curve of a 20 mb, 5 weight percent sample can be found in FIG. 7. This testing indicates that the hydrogels can withstand shear strains on the order of 100% or greater without undergoing any plastic deformations and destruction of the hydrogel structure.

Figure 8:
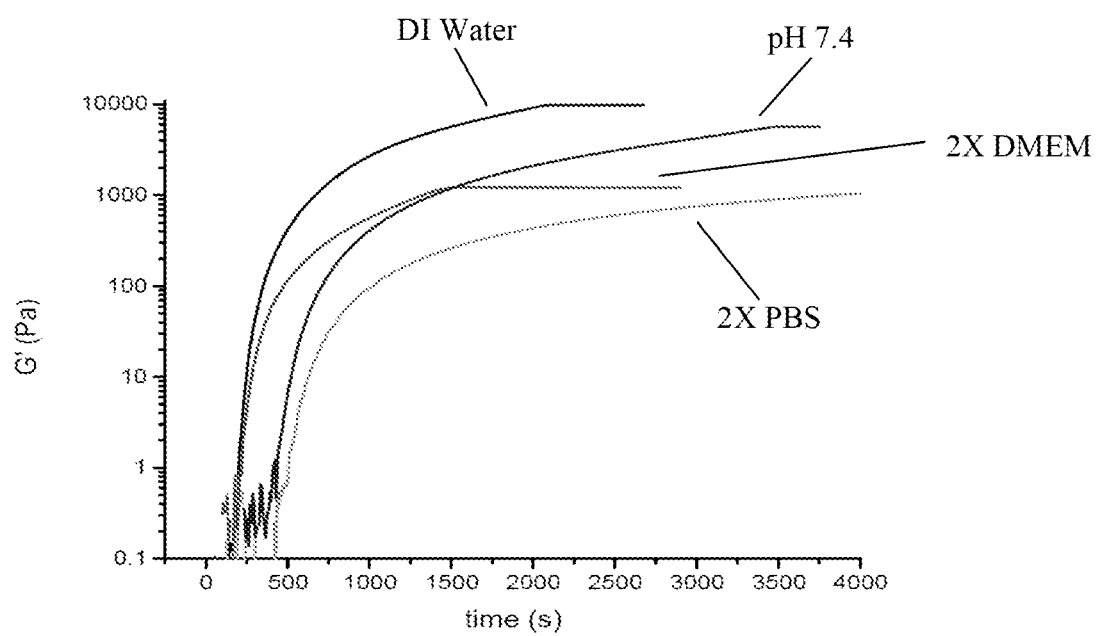
FIG. 8. Kinetics of gels from 30 mb solution with final concentration of 4.1 wt %. Addition of media v. PBS v. pH produces an effect on modulus and kinetics of the gels.

Gelation Kinetics and Mechanics at Physiological Conditions:

A prerequisite for the use of hydrogels for cell encapsulation, is that they be produced under physiologically relevant conditions. For mammalian cells this is typically accomplished by working with one of a number of balanced salt solutions or commercially available cell culture media. The use of these salts has a pronounced deleterious effect on the rate of gelation as well as the final modulus that it achieves. FIG. 8 shows the development of storage modulus for sample gels produced using a final concentration of IX DI water, DPBS, DMEM cell culture media and a solution titrated to a pH of 7.4. As can be seen, the addition of the salts or change in pH results in significantly slower reaction rates and decreased final moduli.

Figure 9:
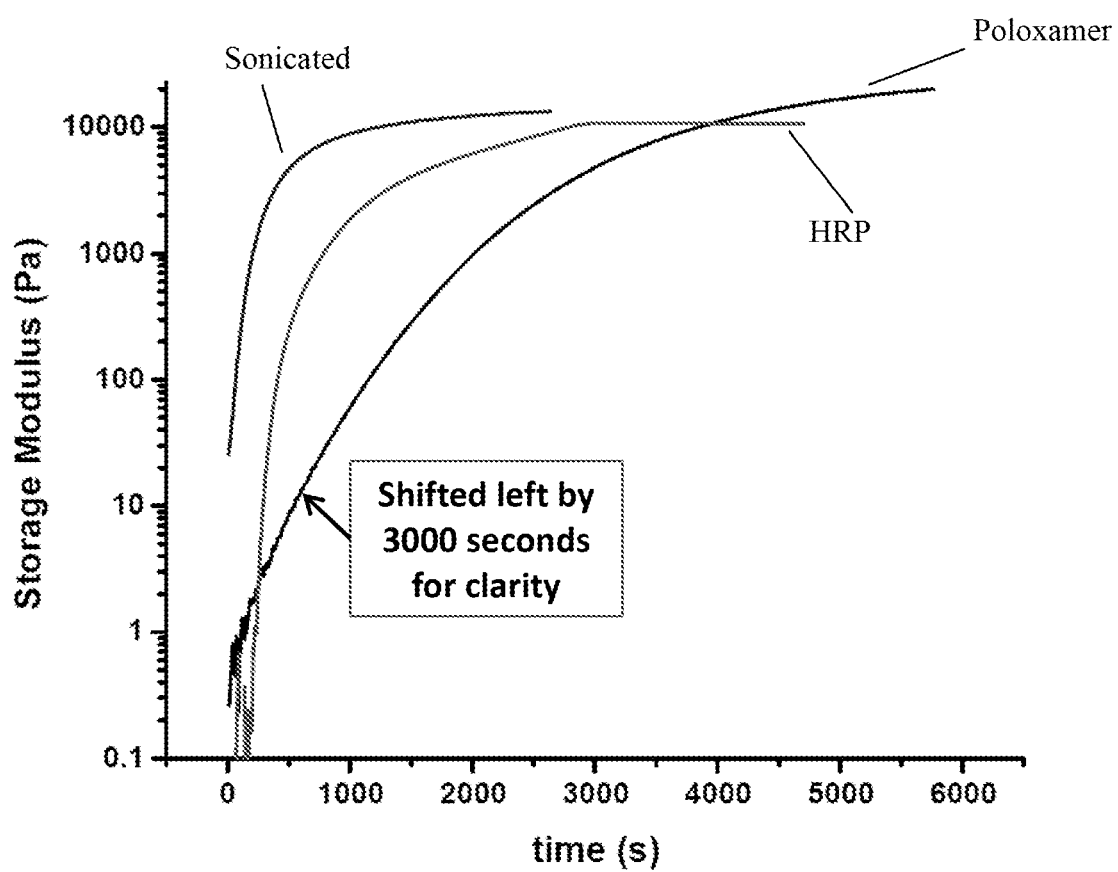
FIG. 9. Kinetics of gels from 30 mb solution with final concentration of 4.1 wt %. Gels were formed by HRP enzymatic crosslinking, sonication or poloxamer F77 addition.
Figure 10:
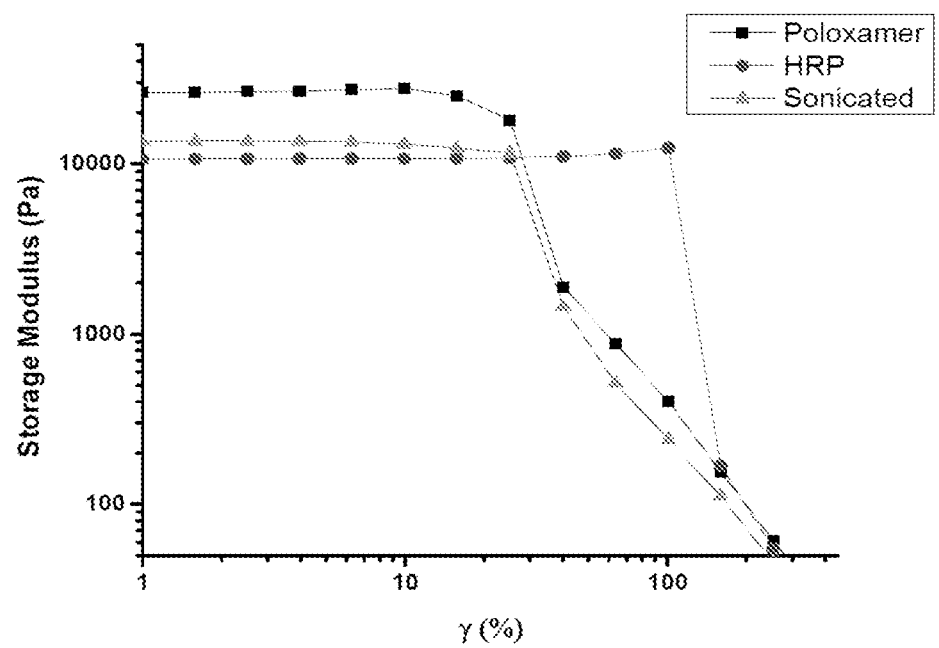
FIG. 10. Strain sweep of gels from 30 mb solution with final concentration of 4.1 wt %. Gels were formed by HRP enzymatic crosslinking, sonication or poloxamer F77 addition.

Comparison of HRP, Sonicated, and Poloxamer Gels:

In order to provide a better comparison of different silk gelation techniques, a 30 mb 4.1% final concentration solution was gelled using three techniques; enzymatic crosslinking, sonication and poloxamer addition. These gels were then assessed for their kinetics, final modulus and adhesion properties. The kinetics of gelation are shown in FIG. 9, please note that the plot for the poloxamer gel was shifted left by 3000 seconds due to its much slower gelation initiation. These tests showed differences in gelation time from roughly 3,000 seconds for the sonicated and HRP gels to 10,000 seconds for the poloxamer gel. Final storage moduli ranged from 10 kPa for the HRP gels to 25 kPa for the poloxamer gels, with the sonicated gel being intermediate at 13 kPa. Following gelation, the samples were subjected to a strain sweep to determine their elasticity. FIG. 10 shows the results, where both the sonicated and poloxamer based hydrogels exhibited plastic deformation at strains on the order of 10%, while the gels produced by crosslinking with HRP were able to recover at strains of up to 100%.

Figure 11:
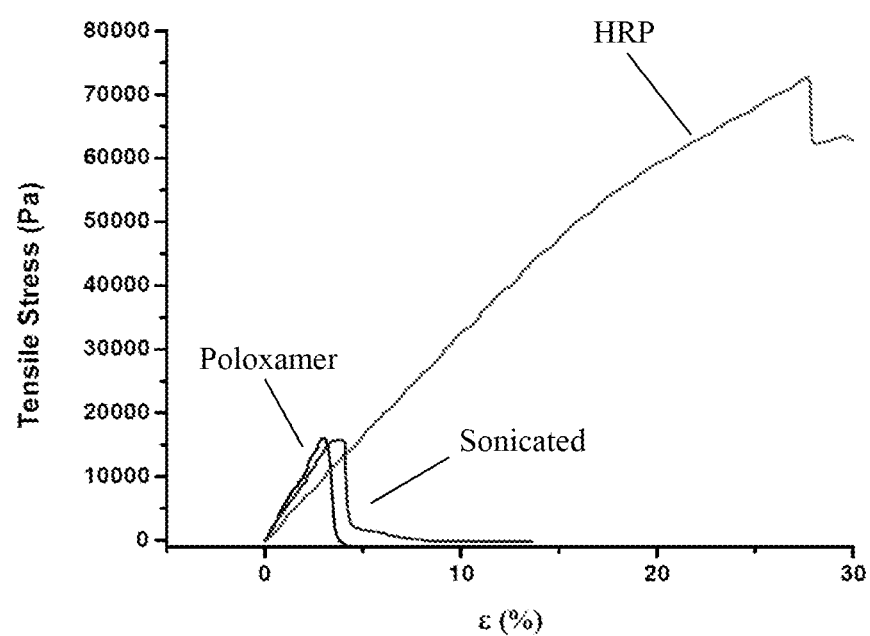
FIG. 11. Stress-strain curves of adhesive properties of gels formed from 30 mb solution with final concentration of 4.1 wt %. Gels were formed by HRP enzymatic crosslinking, sonication or poloxamer F77 addition.

Adhesive properties of the three gels were also evaluated by gelling samples between stainless steel plates and subjecting them to tensile strain. The HRP gels exhibited superior adhesive properties, failing at 72 kPa and 27% strain while both the poloxamer and sonicated gels failed at approximately 15 kPa and 3-4% strain. Plots of the stress-strain curves are shown in FIG. 11.

Figure 12:
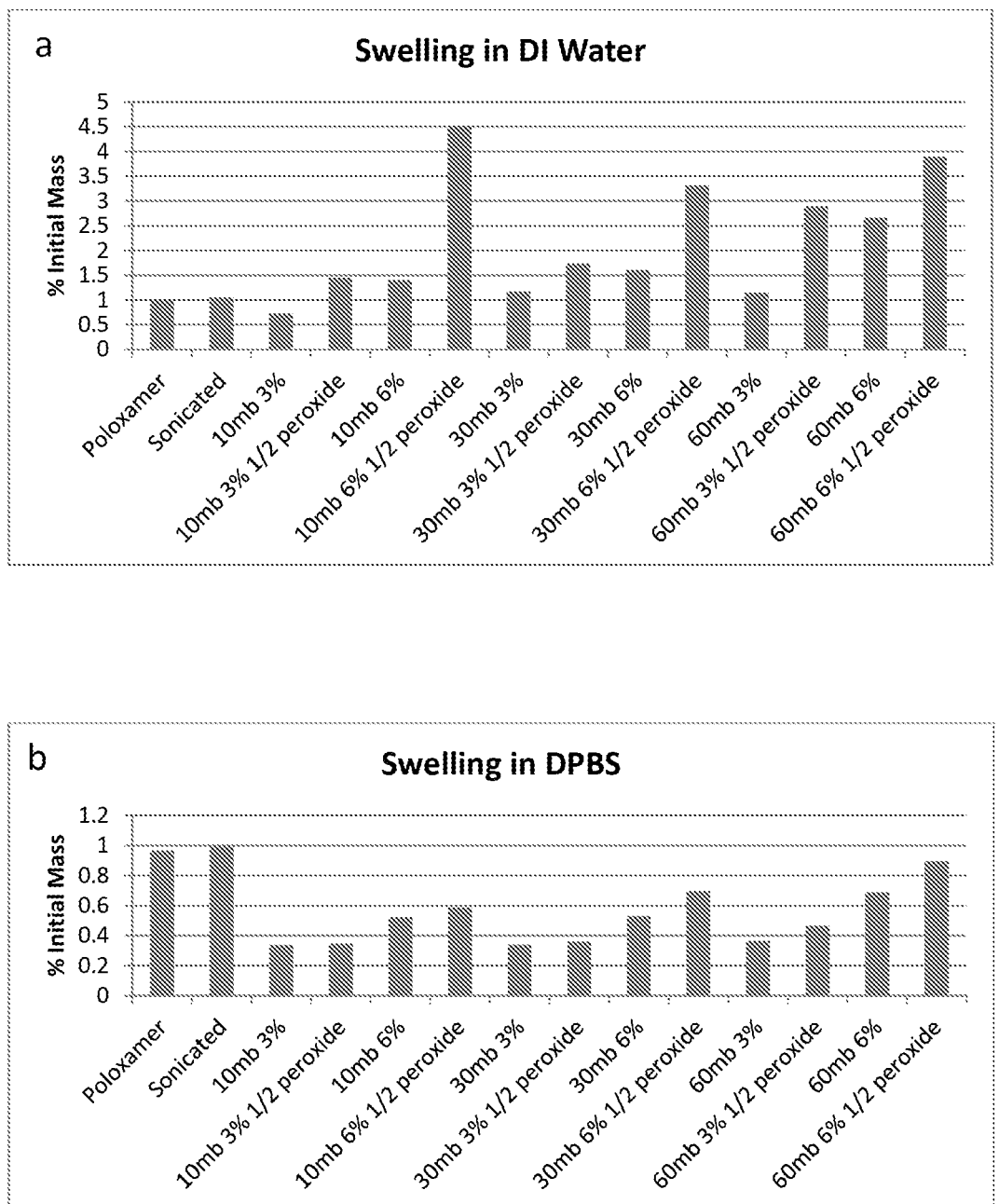
FIG. 12. Comparative swelling of HRP, sonicated and poloxamer hydrogels in DI water as shown in (FIG. 12A) and DPBS as shown in (FIG. 12B). Sonicated and poloxamer gels show negligible swelling/shrinking while HRP gel behavior is modulated by silk molecular weight, concentration and peroxide addition.

Swelling Properties in DI Water and DPBS:

An important property of hydrogels is their ability to swell and retain high concentrations of water. In order to determine the ability of the enzymatically covalently crosslinked silk hydrogels to swell, 8 mm diameter samples were punched from a bulk hydrogel, weighed and placed in DI water or DPBS overnight. Samples were then removed from the water or PBS, gently dried and reweighed. Swelling was calculated as the final mass divided by the initial mass and plotted, as shown for DI water in FIG. 12A and for DPBS in FIG. 12B. Initial confounding results, were repeated and it was determined that swelling is highly tunable by controlling for the concentration and molecular weight of the silk as well as the amount of hydrogen peroxide added.

Figure 13:
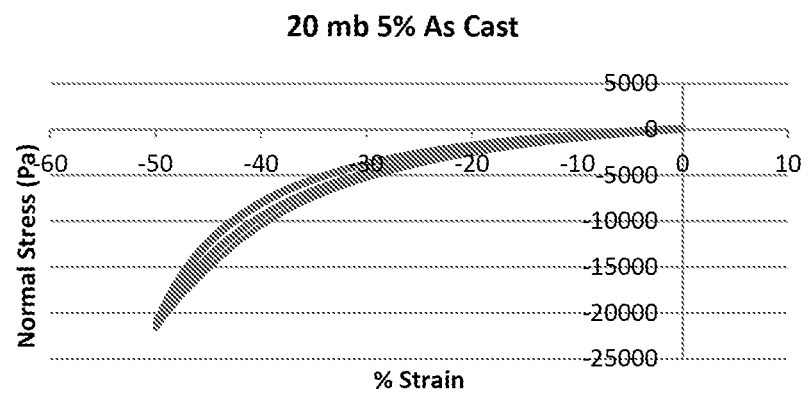
FIG. 13. Cyclic, unconfined compression data, showing 4 cycles of compression and unloading for as cast, shown in (FIG. 13A), water swollen, shown in (FIG. 13B), and methanol treated silk hydrogels, shown in (FIG. 13C).
Figure 13:
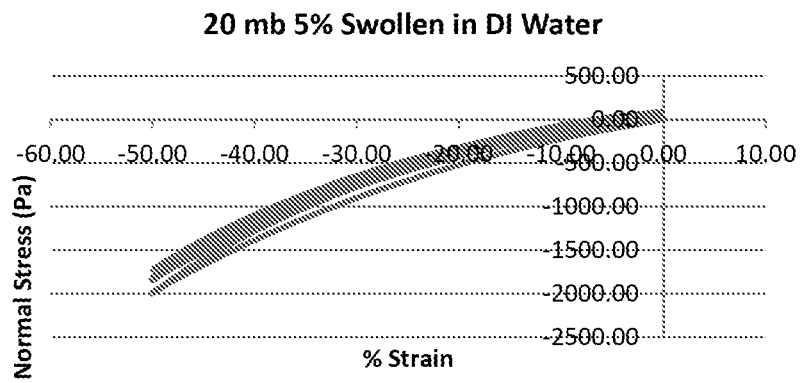
Figure 13:
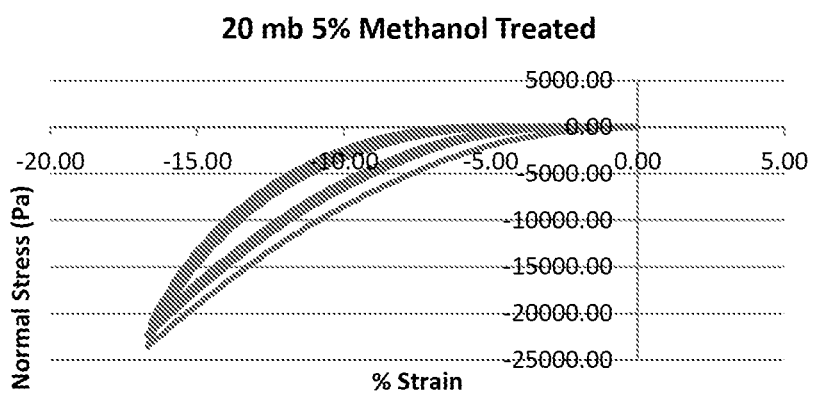
Figure 14:
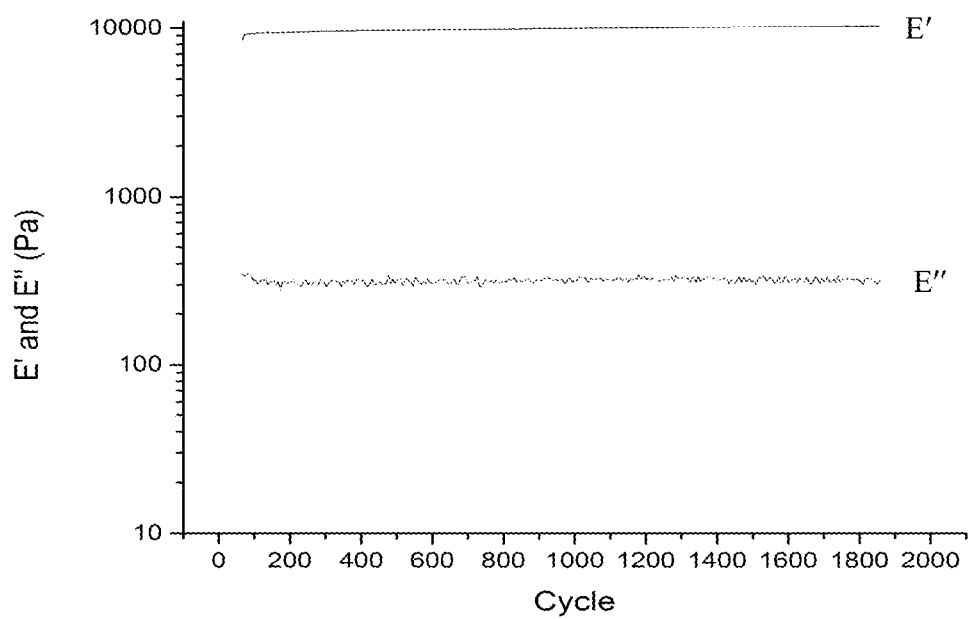
FIG. 14. Elastic and loss moduli for a 20 mb 5% concentration gel over 1,800 cycles at 0.5 Hz and 10% strain showing no deterioration or plastic deformation.

Unconfined Compression:

When tested in compression the hydrogels exhibit elastomeric-like properties, exhibiting no plastic deformation at strains of 50% and near complete mechanical recovery of properties after 4 cycles of this extreme compression. The compression testing also showed that samples that had been swollen in water and those soaked in 50% methanol had significantly lower and higher compressive moduli respectively. Representative curves for the as cast is shown in FIG. 13A, water swollen, shown in FIG. 13B, and methanol treated silk hydrogels, shown in FIG. 13C. Note that the maximum strain achieved for the methanol treated samples was only 16.5% while as cast and water swollen samples were tested to 50% strain. This limitation was due to equipment limitations and requires additional testing to evaluate the properties of the methanol treated hydrogels at higher strains. As seen in FIG. 14, long term durability testing of a 20 mb, 5% concentration sample showed negligible change in moduli after being subjected to 1,800 compression cycles to 10% strain at a frequency of 0.5 Hz.

Figure 15:
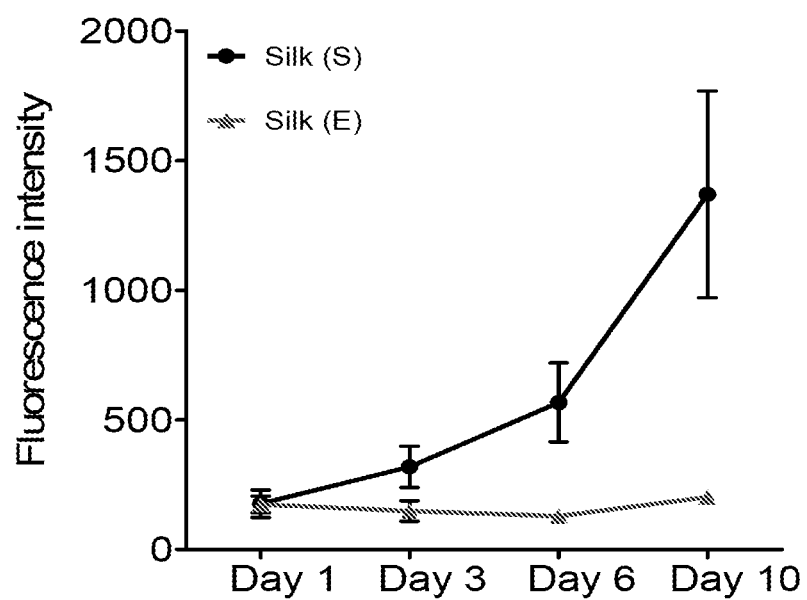
FIG. 15. Alamar blue data showing proliferation of cells on surface of preformed gels (S) and survival of cells that were encapsulated into the gel during formation (E).
Figure 16:
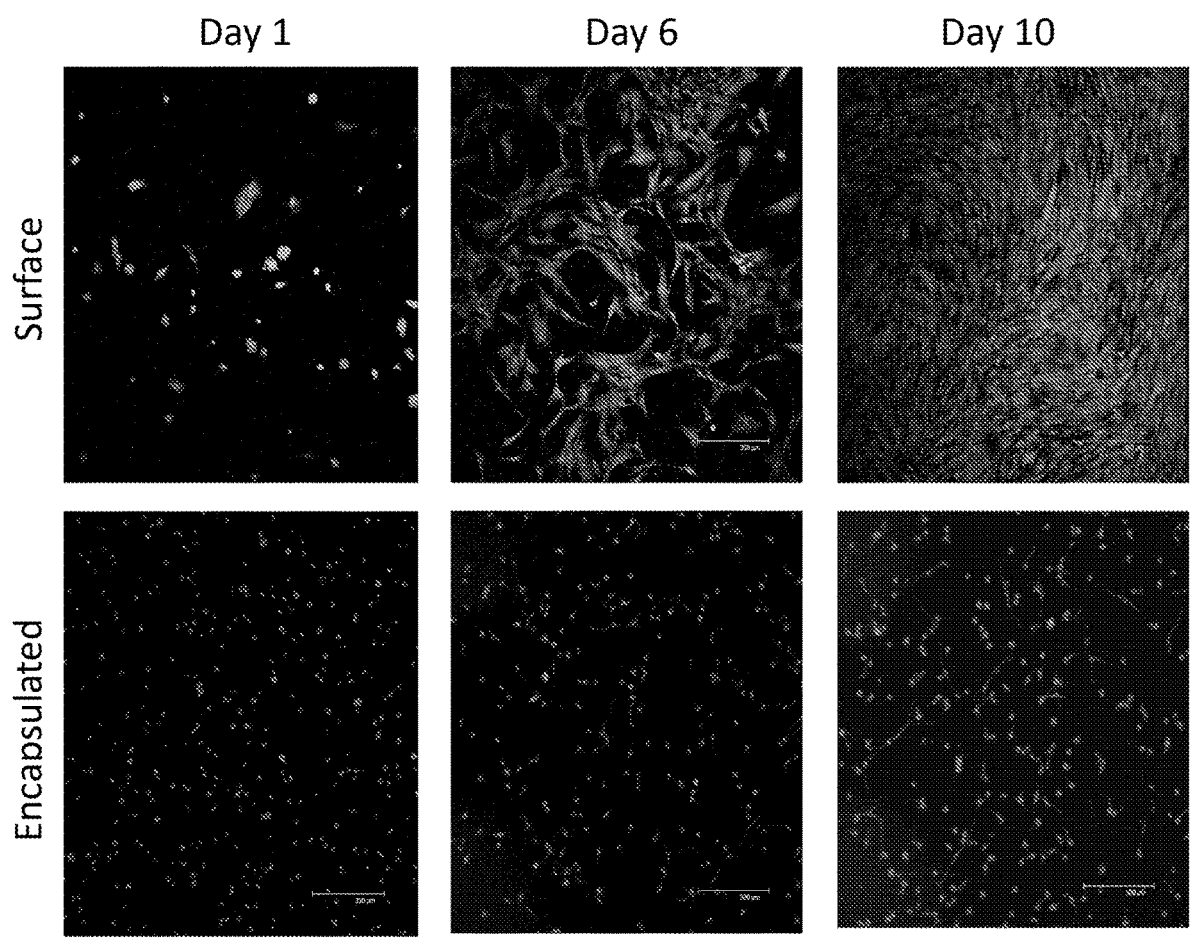
FIG. 16. Representative confocal images of hMSC's seed on the surface of preformed gels and encapsulated into the gel during formation. Scale bar is 300 μm.

Cell Culture:

In order to verify that the hydrogels were a viable substrate for cell growth and encapsulation, hMSC's were grown on both the surface of preformed gels and encapsulated during the gelation process. Due to the retardation of gelation kinetics under appropriate salt and pH conditions, encapsulation was accomplished by partially gelling a silk-1/2× media for 8 minutes, adding the cells and pipetting into the appropriate wells, allowing to gel for an additional 7 minutes and flooding with media. These procedures were required to minimize the time that the cells were subjected to non-isotonic conditions. Alamar blue proliferation assay was performed on day 1, 3, 6 and 10 to assess the viability of the cells over time and is shown in FIG. 15. Confocal images, using a live/dead stain were acquired on day 1, 6 and 10 to evaluate cell morphology. Representative confocal images, indicating that the cells are able to spread and adhere on the surface and maintain viability following encapsulation are shown in FIG. 16.

Figure 17:
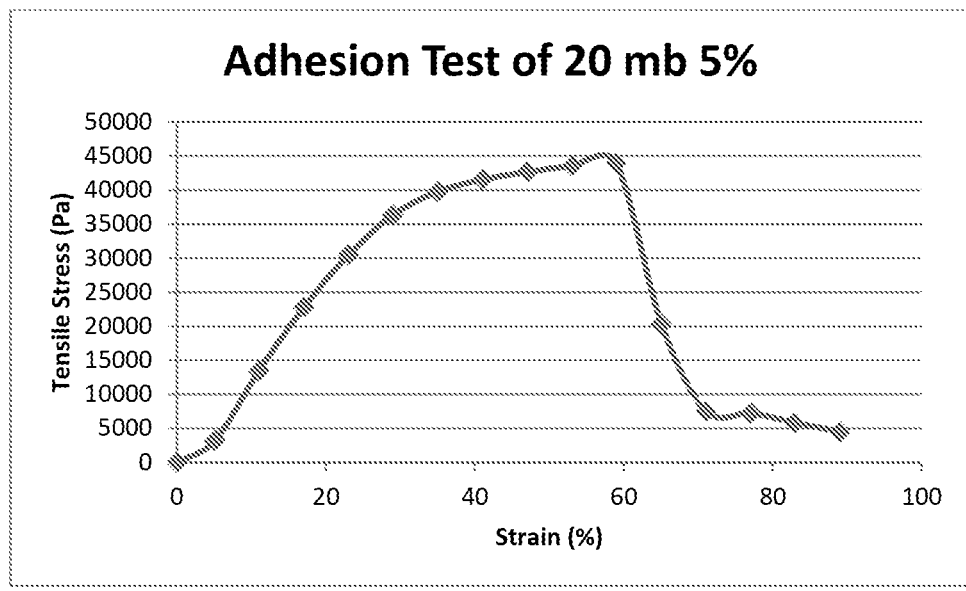
FIG. 17. Adhesion test of 20 mb, 5% concentration gel on stainless steel plates showed remarkable adhesive and tensile properties, with strains of 60% and maximum tensile stress of 44 kPa.

Additional Adhesion Testing:

Adhesion tests were performed on hydrogels to determine their adhesive capacity. This was performed on stainless steel plates for convenience, and any other surfaces such as smooth or rougher surfaces can be used to estimate the adhesive capabilities. As shown in FIG. 17, the hydrogels, when cast in contact with the steel plates, exhibited excellent adhesive characteristics. They were able to withstand strains on the order of 60% and showed tensile stresses of 44 kPa.

Figure 18:
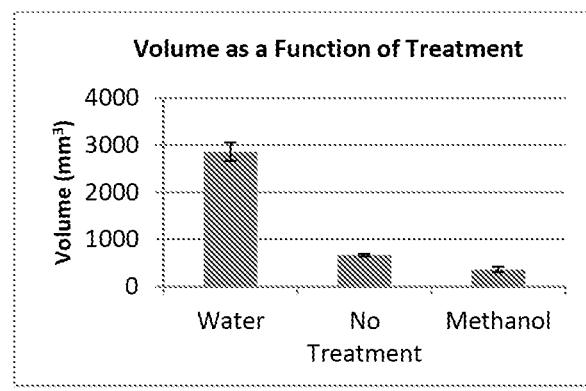
FIG. 18. Water uptake and swelling properties of hydrogels after soaking in deionized water, and methanol. Volume as a function of treatment as shown in (FIG. 18A) and Mass change after swelling in water for 24 hours as shown in (FIG. 18B).
Figure 18:
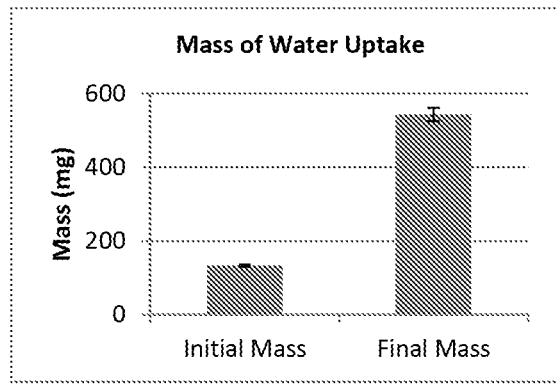

Swelling Properties in DI Water and 50% MeOH:

An important property of hydrogels is their ability to swell and retain high concentrations of water. In order to determine the ability of the enzymatically covalently crosslinked silk hydrogels to swell, 8 mm diameter samples were punched from a bulk hydrogel and refrigerated or allowed to soak in deionized water or 50% methanol solution overnight. The following day the diameter and height of all samples were measured and volumes calculated. The results are shown in FIG. 18A indicating a significant swelling to 2,860 mm$^3$ for samples stored in water versus 666 mm$^3$ for as cast samples and a slight decrease in volume to 362 mm$^3$ for samples subjected to methanol treatment. Water uptake was also recorded by massing samples before and after swelling and calculating the percent increase, these measurements were similar to the volumetric results with an increase of 407+/−14.5% increase in mass after soaking overnight, as shown in FIG. 18B.

Example 2

Preparation of Aqueous Silk Solution

Silk solutions were prepared using procedures previously established and disclosed in D. N. Rockwood, et. al., 6 Nature protocols 1612 (2011) which is hereby incorporated by reference in it entirety. Briefly, 5 grams of *B. mori* silkworm cocoons were immersed in 2 L of boiling 0.02 M Na2CO3 solution (Sigma-Aldrich, St. Louis, Mo.) for 10, 30 or 60 minutes, subsequently referred to as 10 mb, 30 mb and 60 mb respectively, to remove the sericin protein coating. Degummed fibers were collected and rinsed with distilled water three times, then air-dried. The fibers were solubilized in 9.3 M LiBr (Sigma-Aldrich, St. Louis, Mo.) at 60° C. for 4 hours. 15 mL of this solution was then dialyzed against 1 L of distilled water (water changes after 1, 3, 6, 24, 36, and 48 hours) with a regenerated cellulose membrane (3,500 MWCO, Thermo Scientific, Rockford, Ill.). The solubilized silk protein solution was then centrifuged twice (9700 RPM, 20 min., 4° C.) to remove insoluble particulates. Protein concentration was determined by drying a known mass of the silk solution under a hood for 12 hours and assessing the mass of the remaining solids.

Preparation of Enzymatically Covalently Crosslinked Silk Hydrogels:

Horseradish peroxidase (HRP), type VI (Sigma-Aldrich, St. Louis, Mo.) lyophilized powder was mixed with deionized water to form a stock solution with a concentration of 1,000 U/mL. The HRP solution was added to the silk solution in a ratio of 10 Units of HRP to 1 mL of silk solution. To initiate gelation, 10 μL of 165 mM hydrogen peroxide (Sigma Aldrich, St. Louis, Mo.) solution were added per mL of silk solution, for a final concentration of 1.65 mM, and mixed by gentle pipetting prior to setting.

Circular Dichroism (CD):

To perform CD, a 100 μl aliquot of 2% w/v silk solution, 1 μl of HRP and 1 μl of hydrogen peroxide was thoroughly mixed and immediately loaded into 0.01 mm path length demountable quartz cuvette (Starna Cells, Atascadero, Calif.). The sample was then loaded into the spectrophotometer and allowed to gel at 37° C. for 1 hour at which time the spectra were obtained from 260 to 190 nm at a resolution of 0.5 nm. CD measurements were acquired using an Aviv model 62DS spectrophotometer equipped with a temperature controller (AVIV Biomedical, Inc., Lakewood, N.J.). CD spectra presented are the average of three measurements and were smoothed using 9 point Savitzky-Golay smoothing algorithm in OriginPro 9.1 (Origin Lab, Northampton, Mass.).

Fluorescence Spectroscopy:

To assess the intrinsic fluorescence of the solution and hydrogels, 1.5 ml of 1% w/v silk solution was pipetted into a 3 mm pathlength quartz cuvette (Starna Cells, Atascadero, Calif.) and excitation-emission was recorded using a Hitachi F4500 Spectrofluorometer (Hitachi, Schaumburg, Ill.) from 250 nm to 500 nm in 10 nm increments at an intensity of 700 V using a 2.5 nm slit width to avoid saturation. The silk solution was then rinsed from the cuvette and 1.5 mL of new solution, with HRP and $H_2O_2$ were mixed and pipetted into the cuvette. The solution, with initiator, was allowed to gel for 2 hours at room temperature and another excitation-emission spectrum was collected. Spectra were then processed to subtract background fluorescence from the solvent and cuvette and normalized to account for differences in the xenon lamp output spectrum.

Rheology:

Rheological measurements were conducted on the enzymatically covalently crosslinked hydrogels to determine the gelation time and mechanical strength. All rheology was carried out on a TA Instruments ARES-LS2 rheometer (TA Instruments, New Castle, Del.) using a 25 mm stainless steel conical plate (angle: 0.0994 rad) and a temperature controlled Peltier plate set to 37° C. Briefly, gels were mixed by gentle pipetting and 420 µL of solution was loaded under the geometry. Prior to gelation, the geometry was lowered to the specified gap and low viscosity oil was placed around the outside edge of the cone to prevent water evaporation. A dynamic time sweep was conducted at a frequency of 1 Hz (6.283 rad/sec) and 1% strain for 4,000 seconds or until the sample had reached a plateau modulus, whichever occurred first. Following gelation, dynamic strain and frequency sweeps were carried out on the gels to ensure that measurements occurred within the viscoelastic regime and to assess the elasticity and relaxation times of the hydrogels. Silk solutions boiled for 10, 30, and 60 minutes were tested at concentrations of 1%, 3% and 5%.

Hydrogel Cyclic Compression Testing:

Unconfined compression tests were conducted to assess the mechanical properties of the silk hydrogels as well as the recovery following multiple compression cycles. Five percent solutions of silk, boiled for 10, 30 and 60 minutes were used for the cyclic compression testing. Preformed enzymatically covalently crosslinked hydrogels were biopsy punched into cylinders (8 mm 0, 3 mm height) and allowed to fully swell in DI water or contract in PBS for approximately 12 hours. The final diameter of the samples were measured and used for calculation of compressive stresses. Samples were loaded in a TA Instruments RSA3 Dynamic Mechanical Analyzer (TA Instruments, New Castle, Del.) between stainless steel parallel plates in an immersion bath. The upper plate was lowered until a compression force of −3 g was registered. Samples were subjected to five preloading cycles to 40% strain in order to eliminate artifacts. The sixth cycle was recorded and tangent moduli were calculated at 20% and 40% strains for comparison. All testing was conducted at a constant crosshead speed of 1 mm/min. Sequential strain testing until failure was conducted in 10% strain increments from 20% to 80% strain following five preconditioning cycles to 40% strain. Fatigue stability of the gels was tested by monitoring the dynamic modulus at a frequency of 0.5 Hz and 10% strain over the course of 3,600 cycles.

Cell Survival and Proliferation:

Human mesenchymal stem cells (hMSC's) were isolated from fresh bone marrow aspirate (Lonza, Basel, Switzerland) as previously described in G. H. Altman, et. al., 16 *FASEB journal: official publication of the Federation of American Societies for Experimental Biology*, 270 (2002), which is hereby incorporated by reference in its entirety and cultured in Dulbecco's Modified Eagle Medium (supplemented with 10% fetal bovine serum and 1% antibiotic/antimycotic) (Life Technologies, Grand Island, N.Y.) and seeded at passage 3-4. For surface seeding, gels of roughly 400 µm thickness, of 60 mb silk solution at a concentration of 3% wt/v were prepared as described above and allowed to cure for 1 hour, at 37° C. in an incubator. Cells were seeded at 210 cells per $mm^2$, and allowed to adhere for 150 minutes prior to flooding with media. In order to minimize the time the cells were exposed to sub-physiological osmolarity, encapsulation was accomplished by partially gelling the silk solutions. The 60 mb silk solution HRP and $H_2O_2$ were gently mixed allowed to gel for approximately 10 minutes, at which time cells at 500 or 1,000 cells per $mm^3$ were added to the solution and 100 µl per well was added to 48 well plates or glass bottom petri dishes. The plates were placed into an incubator and allowed to gel for an additional 10 minutes at which time the wells were flooded with media. All cell culture was performed in an incubator maintained at 37° C. and 5% $CO_2$.

Metabolic Activity:

The relative metabolic activity of the cells in each scaffold was determined by AlamarBlue assay (Life Technologies, Grand Island, N.Y.) according to the manufacturer's directions. Scaffolds were rinsed with Phosphate Buffered Saline (PBS) and incubated in DMEM medium with 10% AlamarBlue reagent for 4 hours at 37° C. with 5% CO2. Following incubation with the reagent, aliquots (100 µl) were placed into black 96 well plates and the fluorescence quantified using a plate reader with an excitation wavelength of 550 nm and an emission wavelength of 590 nm. Cells plated in tissue culture wells were maintained as above and utilized as controls, while acellular hydrogels were used to adjust for background fluorescence.

Cell Imaging with Confocal Laser Scanning Microscopy:

Imaging of the surface seeded and encapsulated cells was performed by staining with a LIVE/DEAD Viability/Cytotoxicity Kit (Life Technologies, Grand Island, N.Y.) according to the manufacturer's instructions. Briefly, cells were incubated with calcein AM and ethidium homodimer-1 (EthD-1) for 60 minutes to stain live (green) and dead cells (red) respectively. After staining the gels were washed three times with PBS and imaged using a Leica DMIRE2 confocal laser scanning microscope (CLSM) (Wetzlar, Germany) with excitation at 488 nm and emission at 499-537 nm for live cells and excitation at 543 and emission at 620-650 nm for dead cells.

Subcutaneous Implantation:

All in vivo experimentation was conducted under protocols approved by the Tufts Institutional Animal Care and Use Committee. Mice used in this study were 4-6 week old BALBc female mice (Charles River Laboratories, Wilmington, Mass.). The mice were randomly assigned into three timepoints with three animals per group. Each animal had two preformed gels (5 mm 0, 3 mm height) of 2% w/v and 6% w/v protein concentration, subcutaneously implanted in lateral pockets under general anesthesia of oxygen and isofluorane. At week 1, 2 or 4 post-implantation, animals were euthanized and the specimens along with the adjacent tissues were collected for histological examination.

Histochemistry:

Explants were fixed in 10% neutral buffered formalin (NBF) and embedded in paraffin following xylene and graded ethanol incubation. Samples were sectioned to 6 µm thickness, placed on glass slides and paraffin was removed. Sections were then stained with hematoxylin and eosin (H&E) (Sigma-Aldrich, St. Louis, Mo.) to visualize cell nuclei and cytoplasm. Following staining samples were imaged using a Zeiss Axiovert 40 CFL microscope and a 10× objective (Carl Zeiss AG, Germany).

Figure 25:
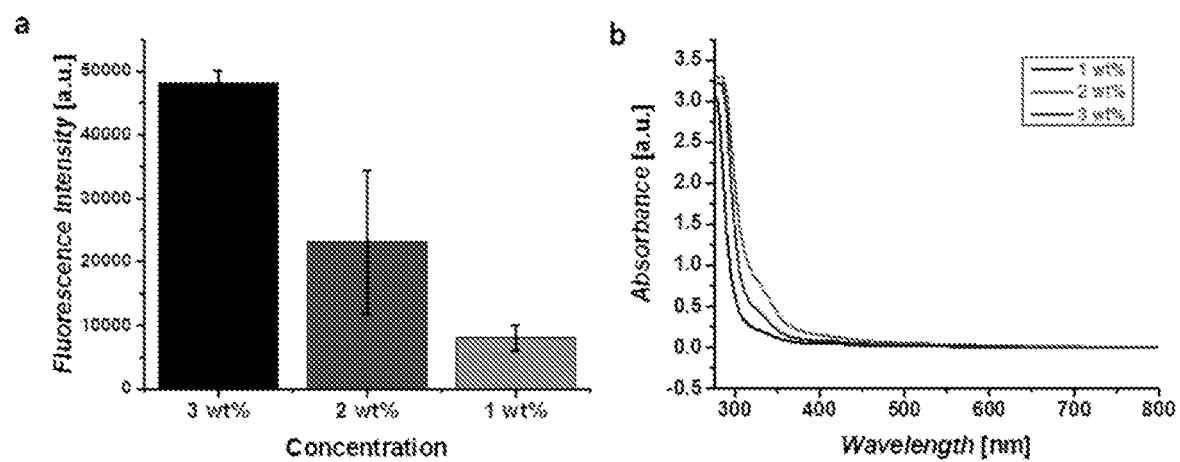
FIG. 25. Fluorescence and optical properties of hydrogels. Fluorescence intensity of hydrogels is directly proportional to the silk fibroin concentration, indicating that the number of dityrosine crosslinks can be related to the fluorescence intensity, shown in (FIG. 25A). Enzymatic silk hydrogels are transparent above ~350 nm simplifying imaging of encapsulated cells, shown in (FIG. 25B).

Statistical Analyses:

Data are expressed as mean±standard deviation. One or two-way analysis of variance (ANOVA) and Tukey post-hoc analysis were used to determine statistically significant differences. Statistical significance was accepted at the $p<0.05$ level and indicated in figures as *$p<0.05$, $p<0.01$, *$p<0.001$ Mechanism of HRP-Mediated Silk Gelation and Structural Characterization:

The addition of HRP to a silk solution in the presence of $H_2O_2$, results in the formation of a stable, highly elastic, transparent gel. This is due to the well-known reaction whereby HRP facilitates crosslinking of the tyrosines in the silk fibroin via the formation of free radical species in the presence of hydrogen peroxide. $H_2O_2$ forms an oxyferryl center and a porphyrin-based cation radical at the active site of HRP, resulting in an activated enzyme which is a powerful reducing agent. HRP then undergoes two single electron oxidation reactions in the presence of a phenolic oxidizing agent to return to its ground state. The overall reaction results in the formation of two water molecules and two phenolic radicals. In this reaction, tyrosine radicals formed through the HRP catalyzed reaction can react with one another to form covalent bonds, shown in FIG. 19A. The formation of the dityrosine bonds and the resultant protein secondary structures were assessed by fluorescence spectroscopy and by Circular Dichroism (CD). The CD spectra, shown in FIG. 19B of the silk solution with HRP revealed random coil conformations with a minima near 200 nm and no distinct peaks. Following gelation, a more ordered conformation was evident with a pronounced minimum around 200 nm and a peak near 195 nm, confirming that the gelation reaction was not due to typical anti-parallel β-sheet formation, which would have a distinct minimum at 218 nm. Dityrosine formation was confirmed by comparison of the fluorescence excitation-emission matrix (EEM) for the silk, shown in FIG. 19C and HRP solutions and the fully formed hydrogel FIG. 19D. These data show a distinct shift in the fluorescence maxima from the solution with an excitation of 290 nm and an emission of 350 nm to the gel with a peak excitation of 300 nm with an emission at 425 nm. The shift in the fluorescence indicates the formation of the covalent crosslinks and the intensity of the fluorescence may be correlated to crosslink density as it increased as a function of silk concentration, shown in FIG. 25A. Furthermore, enzymatic crosslinking resulted in the formation of optically clear gels with negligible absorbance above 350 nm, shown in FIG. 25B, and emission of blue fluorescence when irradiated under UV, that was not present in the precursor solution as shown in FIG. 19E.

Figure 20:
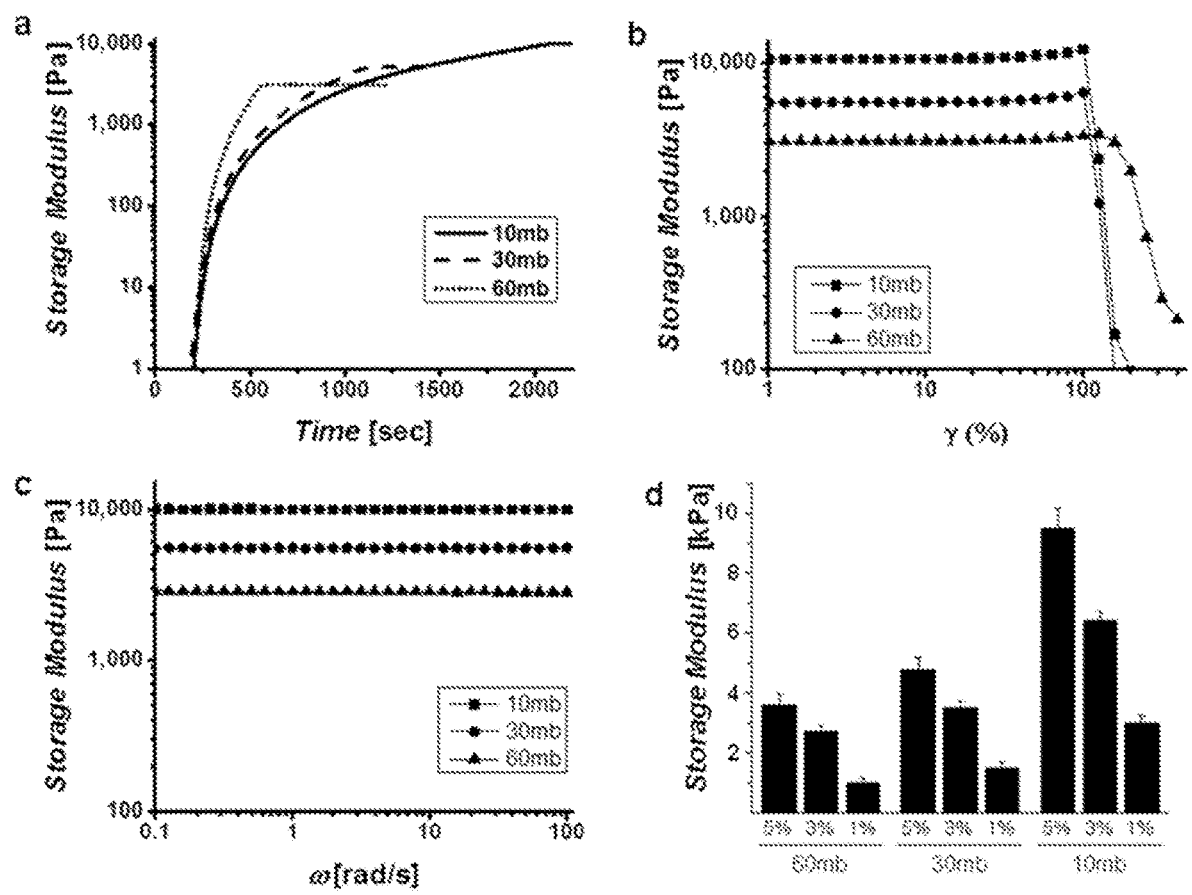
FIG. 20. Rheological properties of hydrogels. Representative gelation kinetics, shown in (FIG. 20A), strain sweeps, shown in (FIG. 20B), and frequency sweeps (FIG. 20C) of different molecular weight gels show controllable kinetics and final mechanical properties in highly resilient, frequency independent gels. Curves indicated were performed at a protein concentration of 5% w/v in DI water. Final storage modulus as a function of molecular weight and concentration, demonstrate the wide range of stiffness achievable is shown in (FIG. 20D).

Rheological Properties of HRP Silk Hydrogels:

The kinetics of gelation and shear properties of the enzymatically covalently crosslinked silk hydrogels were assessed using rheology. Hydrogels of varying molecular weights and protein concentrations were formed in situ in a cone and plate geometry maintained at 37° C. By controlling the solution concentration as well as the molecular weight of the silk fibroin chains the rate at which the gels formed as well as the final mechanical properties were tunable. The boiling time of the silk fibers was inversely related to the molecular weight with 10 mb (10 minutes of boiling to remove the sericin) generating the highest molecular weight. The gelation kinetics, shown in FIG. 20A, frequency, shown in FIG. 20B, and strain responses, shown in FIG. 20C for solutions of 5% w/v protein are shown. These tests indicated that increasing both the molecular weight and the protein concentration resulted in significantly stiffer gels. However, it was found that all gels tested, regardless of molecular weight and protein concentration were frequency independent and were able to withstand shear strains of at least 100%, above which they plastically deformed resulting in a rapid decrease in storage modulus. Based on the conditions studied stiffness values between 200-10,000 Pa were obtained, which covers three orders of magnitude and a significant portion of native tissues properties, as shown in FIG. 20D. In all cases the loss modulus (data not shown) was below the lower limit of the rheometer, indicating that these were highly elastic materials with a negligible viscous component.

Figure 21:
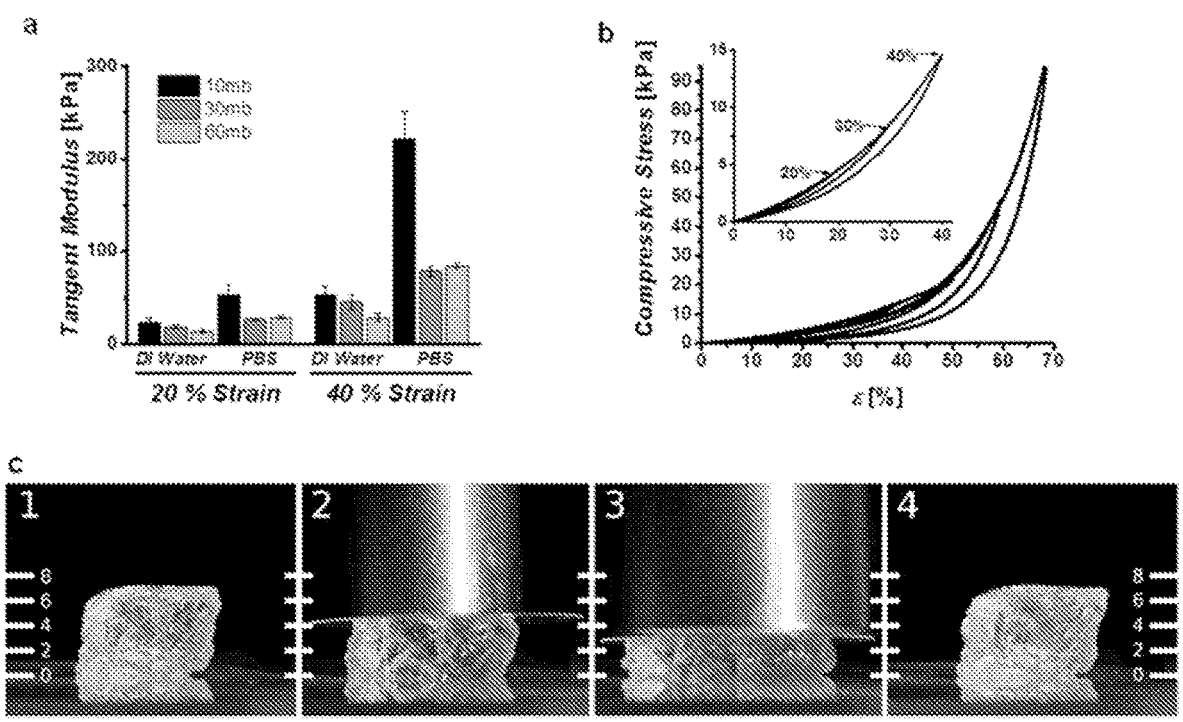
FIG. 21. Compressive properties of hydrogels. Tangent moduli of 5% w/v cast gels swelled in water and PBS show strain and molecular weight dependence, shown in (FIG. 21A). Cyclic compression curves of gels immersed in PBS showing excellent recovery below 70% strain, inset highlights complete recovery below 40% strain, shown in (FIG. 21B). Image of a hydrogel, shown in (FIG. 21C-1), undergoing ~50% compression under 50 g brass weights, shown in (FIG. 21C-2), and 100 g brass weights shown in (FIG. 21C-3), and showing complete recovery after removal (FIG. 21C-4). Scale units are in millimeters.
Figure 26:
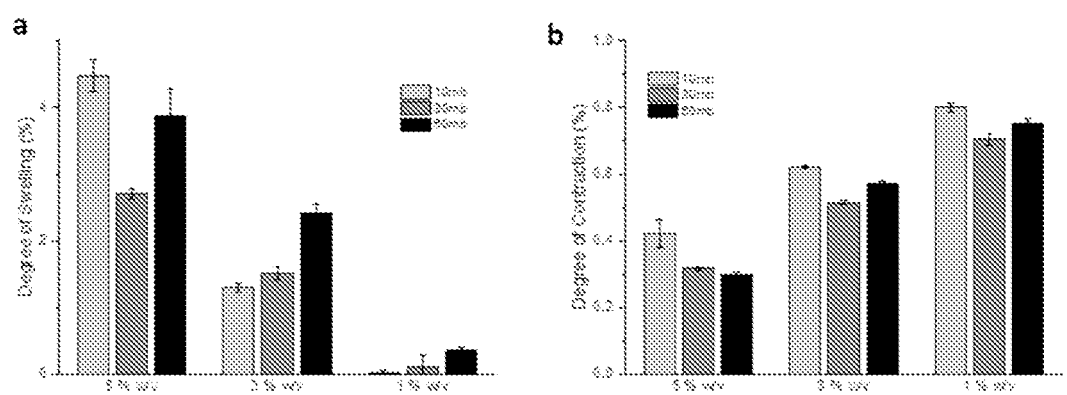
FIG. 26. Swelling and contraction of preformed hydrogels. Swelling of hydrogels after immersion in DI water, shown in (FIG. 26A) and contraction upon immersion in PBS, shown in (FIG. 26B) show sensitivity to both molecular weight and initial protein concentration.
Figure 27:
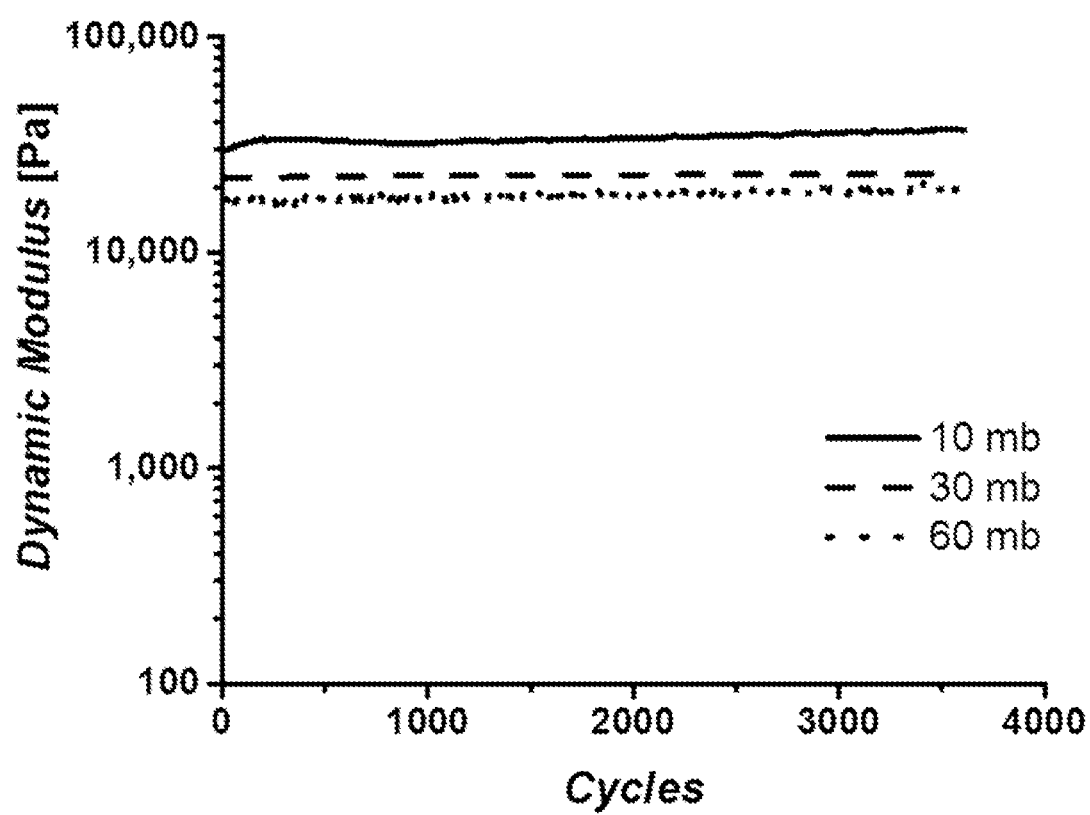
FIG. 27. High cycle fatigue testing of hydrogels. Monitoring of the dynamic modulus of 5 wt % hydrogels over 3,600 cycles to 10% strain at a frequency 0.5 Hz showed negligible change in modulus after minor initial settling. While ability to recover after high numbers of strain cycles was independent of the molecular weight, larger chain length resulted in stiffer hydrogels.

Evaluation of Stiffness and Recovery in Unconfined Compression:

Hydrated unconfined compression studies were carried out to determine the compressive properties of the covalently crosslinked hydrogels. Preformed gels (8 mm φ, 3 mm height, 5% w/v silk concentration) were equilibrated in either DI water or PBS for 12 hours and the final diameter measured. The samples were then placed under a tare load of 3 grams and subjected to 5 compressive cycles to 40% strain to eliminate loading artifacts. The sixth cycle was recorded and the compressive modulus, quantified as the tangent of the stress-strain curve at 20 and 40% strains, was calculated. The stiffness of the hydrogels increased with the magnitude of the compression and increasing molecular weight and were stiffer when immersed in PBS than in DI water, as shown in FIG. 21A. The effect of the solvent was due to the fact that the gels showed significant swelling behavior in DI water, shown in FIG. 26A while contracting in PBS, resulting in different absolute protein concentrations, as shown in FIG. 26B. Despite this swelling or contraction, the gels recovered from compressive strains of over 70% with minimal hysteresis as indicated by representative cyclic loading curves, as shown in FIG. 21B and pictorial representations, as shown in FIG. 21C. While these physiologically extreme strains highlight the excellent resilience of the hydrogels, fatigue resistance of the hydrogel to high cycle moderate strains was more relevant to their use in biomedical applications. To evaluate the fatigue properties of the hydrogels, the dynamic modulus was monitored over 3,600 cycles to a strain magnitude of 10%, as shown in FIG. 27. The samples showed excellent recovery and resistance to fatigue, with minimal changes in their dynamic compressive moduli. These analyses indicate that molecular weight and swelling solvent of the hydrogels allowed control of material properties over several orders of magnitude while maintaining high resilience and resistance to fatigue, even after large numbers of cycles at relatively large strains.

Figure 22:
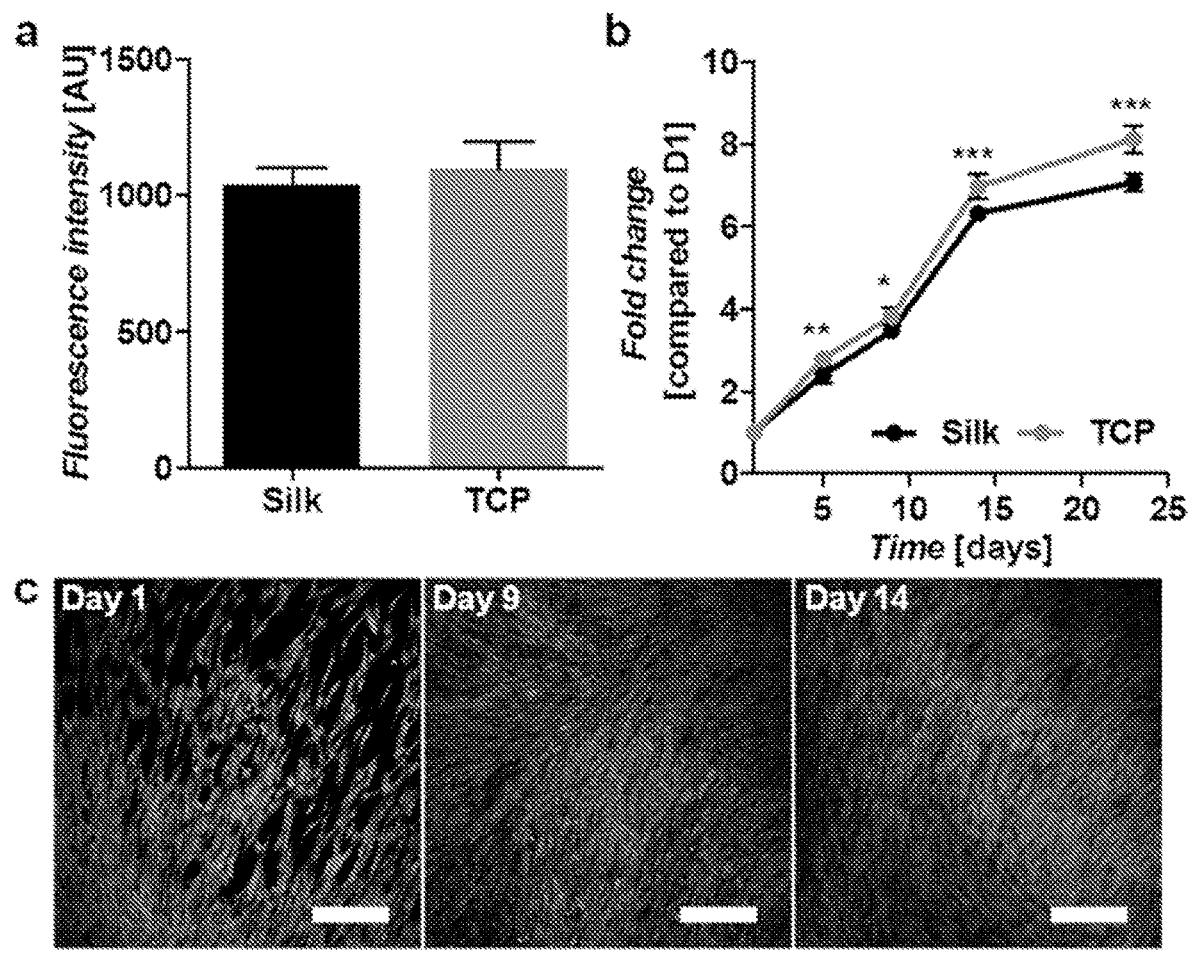
FIG. 22. Human mesenchymal stem cell interactions on silk gel surfaces. Cell attachment on silk and TCP at day 1 post-seeding as determined by Alamar blue, shown in (FIG. 22A). Cell proliferation on silk gels and TCP over a 24-day period as determined by Alamar blue and presented as fold change compared to day 1, shown in (FIG. 22B). Live (green) and dead (red) cell staining on silk gels over a 14-day period, (FIG. 22C). Scale bars are 300 µm.
Figure 23:
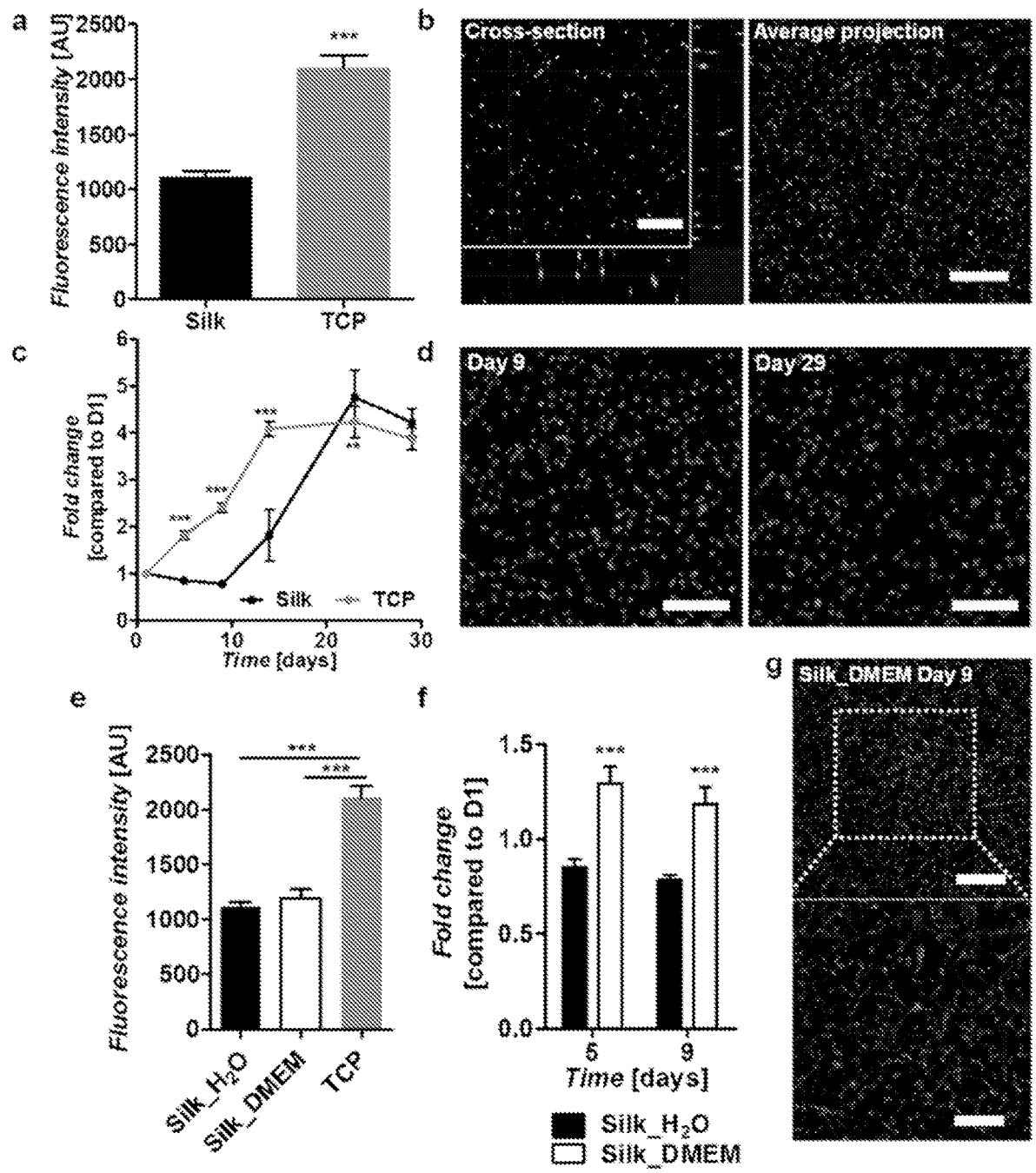
FIG. 23. Human mesenchymal stem cells encapsulated in silk gels. Silk gels were formed in water (FIG. 23A-FIG. 23D). Silk gels formed in water were compared with silk gels formed in DMEM (FIG. 23E-FIG. 23F). Silk gels were formed in DMEM (FIG. 23F). Cell survival following encapsulation in silk gels (formed in water) compared to cells seeded on TCP as determined by Alamar blue at day 1 post-encapsulation, shown in (FIG. 23A). Live (green)) and dead (red) staining on cells encapsulated in silk gels (formed in water) at day 1 post-encapsulation showing a cross-section and an average projection of a 352 µm thick image stack, shown in (FIG. 23B). Cell proliferation on silk gels (formed in water) and TCP over a 29 day period as determined by Alamar blue and presented as fold change compared to day 1, shown in (FIG. 23C). Live (green)) and dead (red) staining of cells encapsulated in silk gels (formed in water) at days 9 and 29 post-seeding showing an average projection of 212 µm and 212 µm thick image stacks respectively, shown in (FIG. 23D). Scale bars are 300 µm. Cell survival following encapsulation in silk gels formed in water and silk gels formed in DMEM compared to cells seeded on TCP as determined by Alamar blue at day 1 post-encapsulation, shown in (FIG. 23E). Comparison of cell proliferation in silk gels formed in water and silk gels formed in DMEM as determined by Alamar blue at days 5 and 9 post-encapsulation and presented as fold change compared to day 1, shown in (FIG. 23F). Live (green)) and dead (red) staining on cells encapsulated in a silk gel formed in DMEM at day 9 post-encapsulation showing an average projection of a 180 µm thick mage stack, shown in (FIG. 23G). Scale bars are 300 µm (top) and 175 µm (bottom).

Cytotoxicity and Cell Encapsulation:

To verify that the hydrogels were viable substrates for cell growth and encapsulation, hMSCs were cultured on the surface of preformed gels as well as encapsulated during the gelation process. Cells seeded onto preformed gels showed similar adhesion as the control tissue culture polystyrene (TCP) surface, as shown in FIG. 22A and supported cell growth and proliferation for greater than 3 weeks, as shown in FIG. 22B. Live/dead staining and confocal imaging confirmed that the cells proliferated until confluence, as shown in FIG. 22C. The influence of the gelation reaction and hydrogel network on cell-matrix interactions was further explored by encapsulating hMSC's in 3% w/v gels formed in sterile water. An Alamar blue assay one day following encapsulation indicated that 52.9±2.3% of the cells survived the gelation versus those plated on TCP, as shown in FIG. 23A. Live/dead staining indicated that the surviving cells were well distributed throughout the thickness of the hydrogel, as shown in FIG. 23B. Subsequently, the hydrogels supported survival and proliferation for at least 29 days, reaching a plateau of 4.2±0.3-fold increase of over day 1 values, as shown in FIG. 23C. Confocal imaging confirmed viability, but showed that the cells exhibited minimal interaction with the matrix and retained a spherical morphology with few extensions, as shown in FIG. 23D. To avoid cell mortality during the encapsulation process cells were also tested in 3% w/v silk gels formed in half concentration of Dulbecco's Modified Eagle's Medium (DMEM) solution. This method did not significantly impact initial cell survival, as shown in FIG. 23E, however, the cells began proliferating immediately and showed a significantly faster growth rate ($p<0.001$) when compared to those encapsulated in water, as shown in FIG. 23F. More interestingly, the morphology of the cells encapsulated in DMEM was strikingly different with greater cell spreading and cell extensions on the order of several hundred microns, as shown in FIG. 23G.

Figure 24:
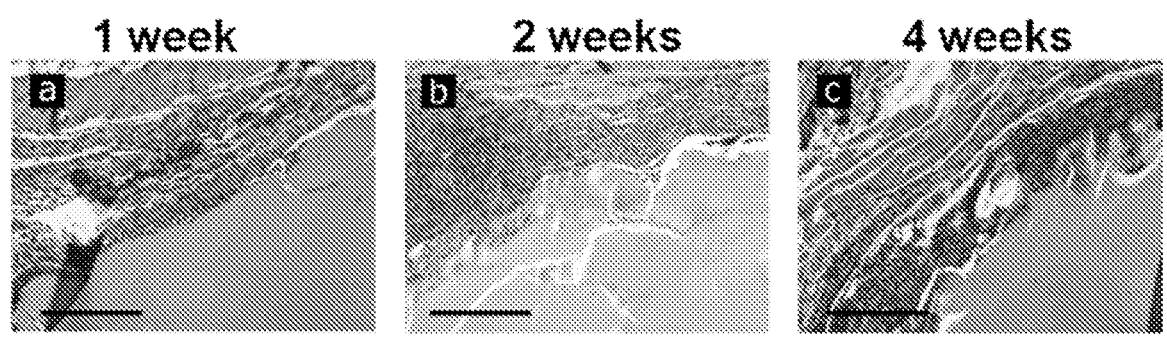
FIG. 24. In vivo interactions with implanted silk gels. Preformed hydrogels of 6% w/v were implanted subcutaneously in a mouse model. Gels were explanted and examined histologically by hematoxylin and eosin (H&E) staining 1 week following implantation, shown in (FIG. 24A), 2 weeks following implantation, shown in (FIG. 24B), and 4 weeks following implantation, shown in (FIG. 24C). The hydrogels showed progressive cell infiltration and degradation as the duration was increased. Scale bars are 250 µm.
Figure 28:
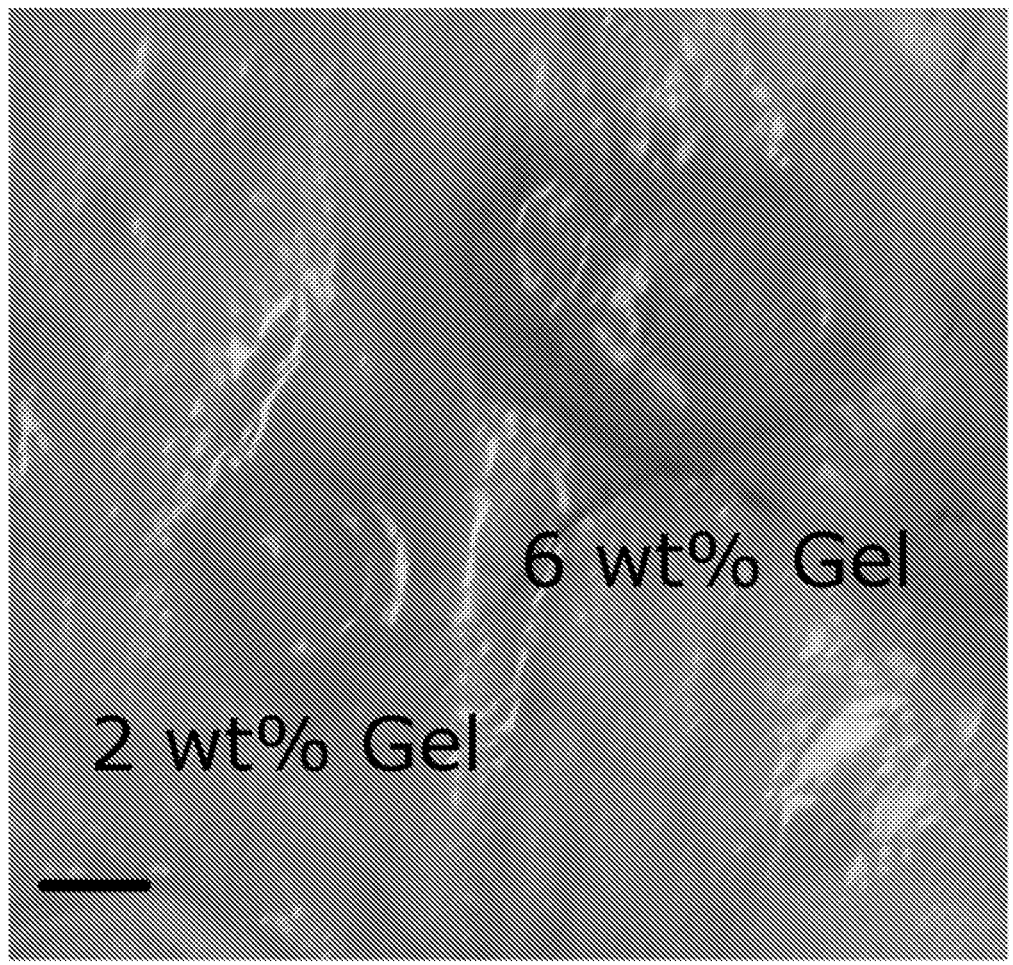
FIG. 28. Contraction of gels at time of explanation. Hydrogels of 2 wt % and 6 wt % implanted in a murine subcutaneous model, exhibited differences in the degree of contraction. The 6 wt % hydrogels maintained their initial dimensions while the lower concentration gels showed pronounced contraction in vivo. Scale bar is 2 mm.

In Vivo Biocompatibility of Enzymatic Hydrogels:

Preformed hydrogels (5 mm 0, 3 mm height) of 2% w/v and 6% w/v silk protein were implanted subcutaneously in mice and examined histologically at one, two and four weeks post-implantation. Explanted gels formed from 2% w/v solution contracted appreciably while the 6% w/v hydrogels maintained their initial volume, as shown in FIG. 28. H&E staining showed that the silk gels elicited a typical foreign body response at respective harvest time points, without excessive inflammation. Despite the contraction of the 2% gels after implantation there were no significant differences in host response to the hydrogels and only the 6% w/v gels are shown for clarity. After one week of implantation, shown in FIG. 24A, the gels had retained their shape, with immune cells at the interface of the gel and tissue, with minimal infiltration into the bulk of the gel. Sectioning of explants after two weeks, shown in FIG. 24B, showed a less distinct interface between the gel and adjacent tissues as the silk gel became integrated. This trend continued at four weeks, as shown in FIG. 24C, with further erosion of the gel periphery and evidence of gel fragments that had been broken from the bulk and were fully surrounded by cells. The degradation of the gel was accompanied by an apparent decrease in the number of adjacent immune cells.

Advancements in tissue engineering and regenerative medicine are dependent on the development of easily prepared, inexpensive, biocompatible and biodegradable materials that can match the resilience, durability and mechanical properties found in native tissues. The covalent dityrosine bonds of the hydrogels presented here result in a robust hydrogel network to achieve high stiffness, while the lack of rigid crystalline segments imbues them with excellent elasticity and resilience. Furthermore, silk precursor materials have been well-studied, can be prepared in bulk and have been shown to be both biocompatible and biodegradable. The wide range of properties and high resilience of these hydrogels suggest that they may be useful for numerous in vivo and in vitro applications where soft, tunable and elastomeric substrates are required.

Figure 19:
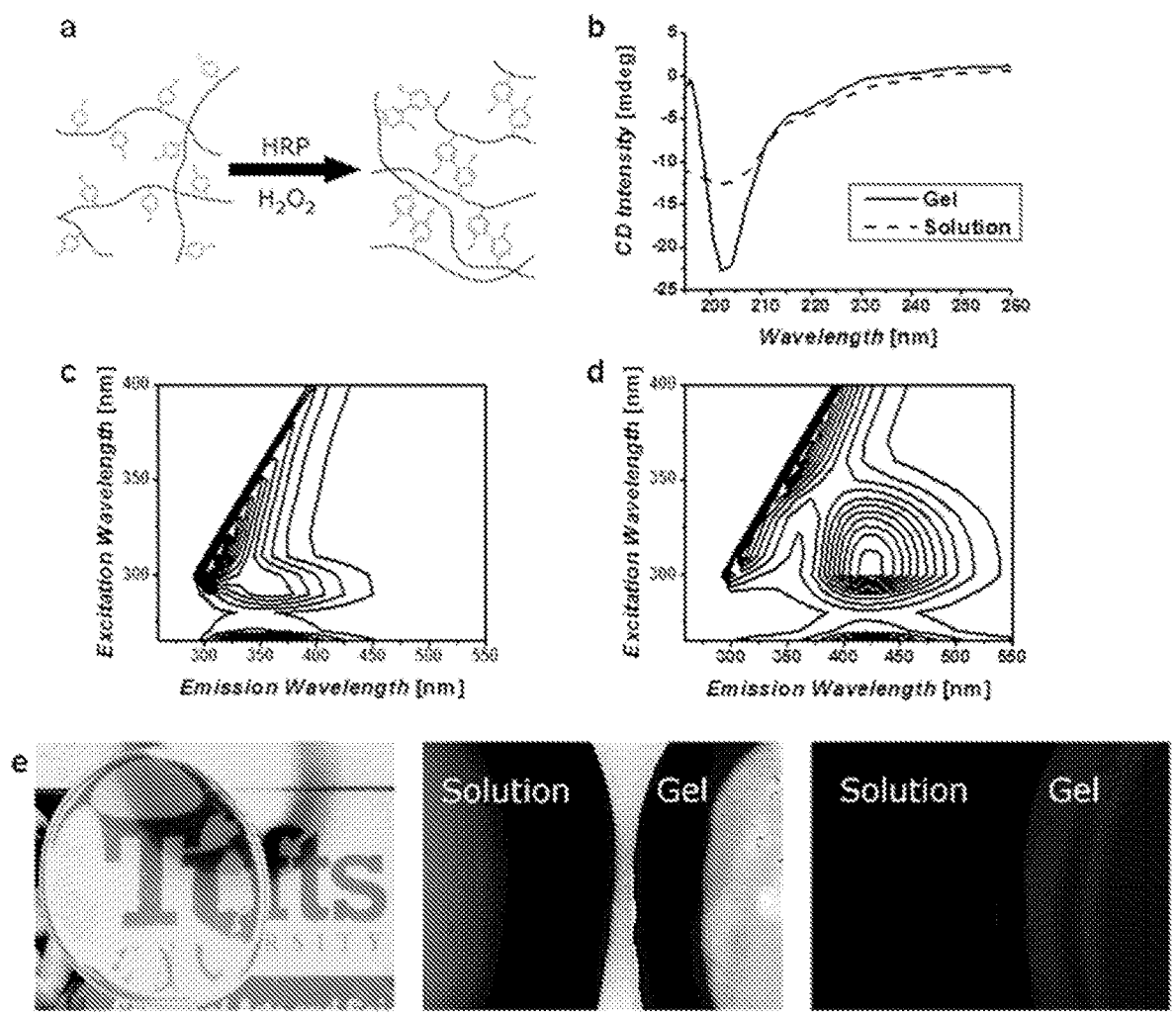
FIG. 19. Chemistry and structural characterization. Schematic representation of the crosslinking of tyrosine residues on silk molecules, these covalent bonds allow for chain extension creating highly elastic hydrogels, shown in (FIG. 19A). Circular Dichroism (CD) spectra of silk solution and enzymatically formed hydrogels, shown in (FIG. 19B) show a change to a helical structure and not β-sheet as found in other silk materials. Fluorescence excitation-emission spectra of solution, shown in (FIG. 19C) and gel (FIG. 19D) confirm the formation of dityrosine bonds. The resultant hydrogels are optically clear and exhibit a blue fluorescence when irradiated with UV that is not present in the precursor solution, as shown in (FIG. 19E).

The bonding of adjacent tyrosine residues has been implicated as a fundamental component in several elastic and structural proteins including resilin, elastin, and keratin. Dityrosine residues have also been found to occur in wild type Tussah silk fibroin, but were not present in the domesticated *B. mori* fibroin investigated here. The widespread existence of dityrosines in structural proteins combined with the well-studied peroxidase-mediated oxidative coupling of accessible tyrosines in the presence of hydrogen peroxide has led to the development of several hydrogel systems based on this reaction, including hyaluronic acid, gelatin, and alginate. In addition to providing mild, physiologically relevant reaction conditions, the peroxidase reaction allows for significant tunability by varying the solution and reagent parameters, including tyrosine concentration and accessibility, HRP and $H_2O_2$ concentrations and substrate molecular weight. As demonstrated in this study, the same mechanism is also applicable to regenerated silk fibroin solutions, where the formation of the tyrosine covalently crosslinked networks results in an optically clear, highly elastic protein hydrogel, as shown in FIG. 19. This suggests that in addition to the variables explored here, control over HRP and $H_2O_2$ may serve as additional modes to further tune the hydrogels.

While many of the hydrogels developed in the biomaterials field to date have shown tunable mechanics, cell encapsulation features, biocompatibility, biodegradability or elasticity, none of the current options in the field offers the combination of all of these characteristics. The enzymatically covalently crosslinked hydrogels presented here meet all of these criteria with shear moduli from the hundreds of Pascals to over ten kilopascals and tangent moduli from fifteen to four hundred kilopascals. Further, these new gels are not cytotoxic and they support cell encapsulation, are biocompatible and biodegradable and are capable of recovering from extreme compressive strains. Additionally, the sensitivity of the gels to swelling in low ionic strength solvents and contraction in high salt solution, as shown in FIG. 26 is governed by both the initial protein concentration and molecular weight, allowing for selection of both modulus and degree of contraction for a given application.

Most importantly these hydrogels represent excellent candidates as biomaterials for applications that require the ability to fully recover from large strains or long term cyclic compression. It has been shown in numerous cases that scaffold modulus and mechanical stimulation are critical for proper development of tissues. Similarly, excessive local stress and strain have been implicated in pathological remodeling of tissues. Thus, it is imperative that a material for use in engineering or replacing these dynamic tissues support long term strains without appreciable changes in mechanical properties. As demonstrated in the present study, these enzymatically formed silk hydrogels are capable of withstanding 3,600 cycles of 10% strain with negligible changes in modulus, suggesting that they are a likely platform for use in dynamic tissue engineering such as cardiac and skeletal muscle.

In addition to their superior resilience, these hydrogels also allow for long term hMSC survival both on the surface and encapsulated within the matrix. Adhesion of cells onto the surface of gels was not significantly different than on TCP and while proliferation was slower than on TCP, the fold change was of the same order of magnitude. This suggests that the hydrogels are not cytotoxic and warrant further investigation as elastomeric biomaterials. While surface seeding of cells is an important screen, numerous synthetic elastomers that require toxic crosslinking agents and solvents are also capable of supporting cell growth after proper curing and removal or inactivation of the deleterious substances. Therefore, to advance the elastomeric biomaterials field, new materials must also allow for the direct encapsulation of cells in addition to withstanding repeated strains. Due to retardation of the gelling reaction in a solution of physiologic salt concentration, cells were initially encapsulated in hydrogels formed in water or cell culture media at reduced concentrations. Despite cell losses during the encapsulation process, the cells that survived were robust and capable of long term proliferation and survival. These results are promising and show the potential of the hydrogels for three dimensional cell culture, either to avoid cell-specific morphologies (as in the case of the water), or different morphologies (depending on the concentration of DMEM used during crosslinking) With suitable gel functionalization or inclusion of ECM components, cell responses should be tunable to specific tissue needs.

Figure 29:
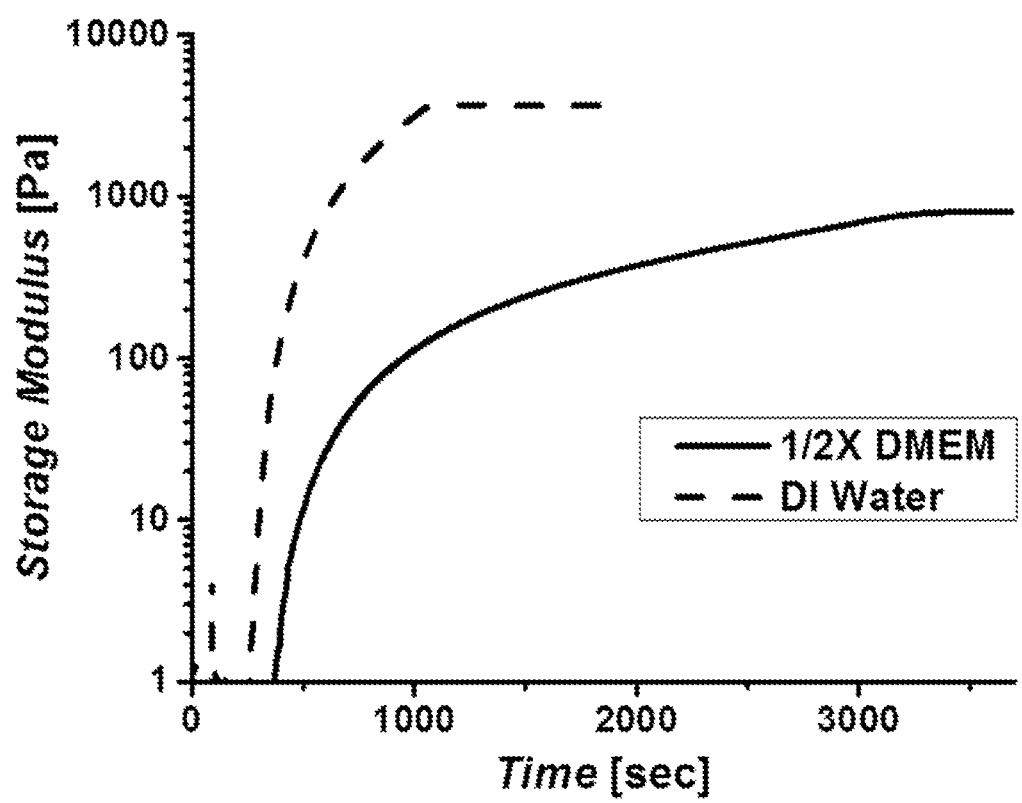
FIG. 29. Cell culture media negatively impacts gelation kinetics and final stiffness. Hydrogels that are formed from 60 mb, 3 wt % silk solutions exhibit slower gelling rates and lower final storage modulus when formed in the presence of buffered media than those formed in DI water.
Figure 30:
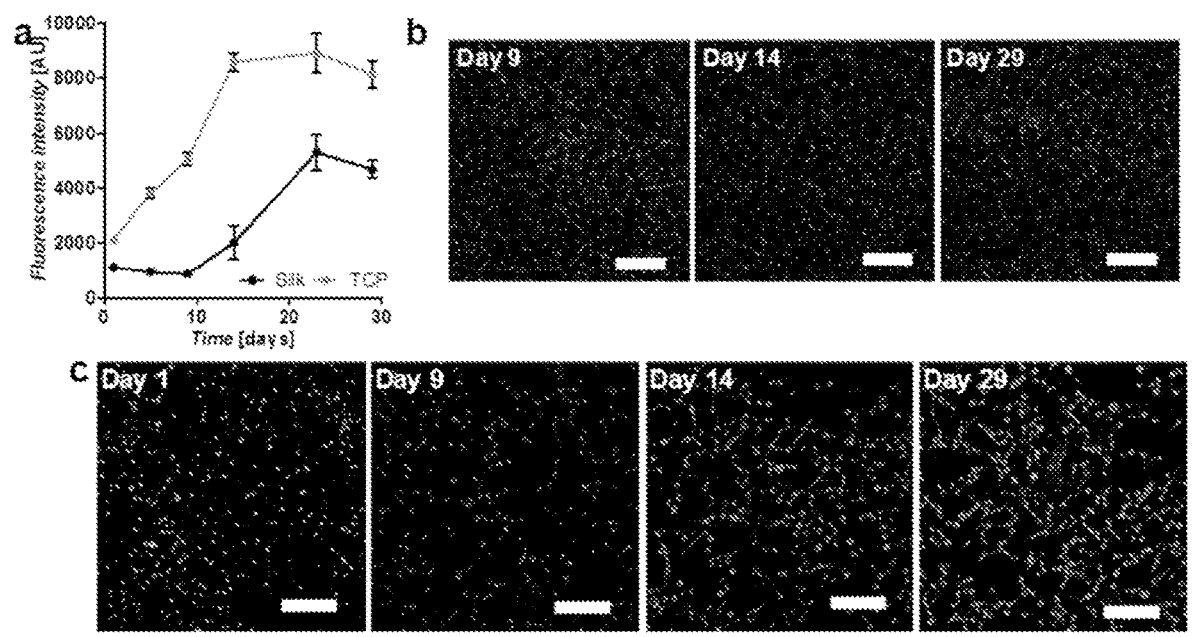
FIG. 30. Human mesenchymal stem cells interactions with silk gels. Cell proliferation on the surface of silk gels formed in water compared to TCP as determined by Alamar blue over a 29 day period, shown in (FIG. 30A). Live (green) and dead (red) staining of cells encapsulated in silk gels formed in DMEM over a 29-day period showing average projections of 179 µm, 234 µm and 200 µm thick image stacks, shown in (FIG. 30B). Scale bars are 300 µm. Live (green) and dead (red) staining of cells encapsulated in silk gels formed in water at a lower silk concentration (1.5% silk compared to 3% presented in other figures) over a 29-day period showing average projections of 81 µm, 83 µm, 49 µm and 71 µm thick image stacks, shown in (FIG. 30C). Scale bars are 300 µm

The dramatically different cell morphologies formed in DMEM indicated that network strength was weaker than those formed in water. The weaker network formation in media was confirmed using rheology, where gels formed in media were less stiff than those covalently crosslinked in water, as shown in FIG. 29. Thus, it seems that the cells were able to exploit weaker networks to spread and form extensions that were visible in the confocal images, shown in FIG. 23G. The hypothesis that network strength was responsible for the differences in cell morphology was further supported by experiments at lower protein concentrations (1.5% w/v vs. 3% w/v). Cells grown in the lower concentration gels, with weaker mechanics and a higher water content, had similar morphologies to those formed in the DMEM-based hydrogels with a flattened appearance and distinct extensions, as shown over time in FIG. 30. These experiments show that in addition to tunable mechanics these hydrogels may allow for control of cell-matrix interactions and the ability to influence cell shape. This may serve as an independent means of manipulating cell differentiation, as cell shape has been previously implicated as a factor in commitment of a stem cell to a given lineage. While similar properties have been shown in synthetic hydrogels with highly controlled chemistries, the ability to incorporate this functionality into a protein based hydrogel provides a more natural platform to study these interactions. Previous work has already shown the utility of silk in controlling neuron outgrowth, hMSC differentiation and survival, and development of adipose like tissue, the present hydrogels allows for the further expansion of these diverse applications and signaling cues.

The success of the hydrogels for cell encapsulation and utility in vivo may also be enhanced by recent developments based on silk systems. The molding of channels into scaffolds was advantageous for cell infiltration for soft tissue repair and replacement in a mouse model. This method employed the use of a linear wire arrays to form channels throughout a scaffold to enhance diffusion of oxygen and nutrients and promote vascularization in critically sized defects. This technique can be readily employed with these hydrogels allowing for implantation of larger scaffolds without concern for necrosis due to diffusion limits. Silk has also been found to be a promising candidate for delivery and release of growth factors, antibodies, and antibiotics. The addition of these bioactive agents is possible due to the all aqueous processing of the hydrogels and may further enhance this highly tunable system.

Silk has been explored for soft tissue augmentation, cartilage regeneration, and vascular regeneration, all of which can benefit from the unique combination of elasticity and tunable mechanics presented here. The gels were well tolerated subcutaneously, shown in FIG. 24, suggesting that further study is warranted for targeted applications. Furthermore, the mild nature of the crosslinking, makes the technique amenable to incorporation of cells and bioactive molecules, as well as the development of an injectable system, as has been accomplished with other materials employing this reaction. The ability to influence cell-matrix interactions in vivo may also be exploited to control integration of the biomaterial following implantation. The combination of these attributes, in addition to the high resilience, makes this silk gelation system a promising system for numerous applications in regenerative medicine.

In addition to its use as a biomaterial, in some embodiments, silk has enjoyed utility as a platform for electronics, optics and related technological applications. Hydrogels described here have potential as substrates for these technologies where the elastomeric nature can be exploited to create flexible, biocompatible, three dimensional optical and electronic devices. Additionally, due to the strong multiphoton absorption of silk fibroin these gels are a promising candidate for three-dimensional femtosecond micromachining, which when combined with the optical transparency of the hydrogels may be used to develop novel optical sensors and devices.

Elastomeric, fully degradable and biocompatible biomaterials are rare, with existing options presenting significant limitations in terms of ease of functionalization, tunable mechanical properties, and tunable degradation properties. Hydrogels of the present invention and methods of forming hydrogels of the present invention represent a new family of natural, biocompatible, biodegradable elastomeric hydrogels for use in fields of endeavor such as tissue engineering, regenerative medicine, and optics.

Methods of the present invention provide for covalent crosslinking of tyrosine residues in silk proteins, via horseradish peroxidase and hydrogen peroxide. Enzymatically covalently crosslinked hydrogels of the present invention are highly elastic, possess exceptional resilience, controllable gelation kinetics, highly tunable mechanical properties, are well tolerated when implanted in vivo, and possess an ability to support cell encapsulation, cell survival, and cell proliferation. Hydrogels of the present invention are amenable to stiffening by induction of β-sheet while maintaining a considerable degree of elasticity. Additionally, all aqueous processing of methods of manufacturing hydrogels of the present invention offer a broad platform for biomaterial functionalization and utility are amenable to incorporation of functional moieties, agents, such as other ECM proteins, growth factors, etc., allowing for control of cell-matrix interactions and increasing versatility. Hydrogels as described herein provide a unique combination of characteristics, and, therefore, are capable of faithfully recapitulating numerous properties of native extracellular matrices, while retaining a high level of versatility, thereby eliminating many of the disadvantages inherent in existing elastomeric biomaterials.

Other Embodiments and Equivalents

While the present disclosures have been described in conjunction with various embodiments and examples, it is not intended that they be limited to such embodiments or examples. On the contrary, the disclosures encompass various alternatives, modifications, and equivalents, as will be appreciated by those of skill in the art. Accordingly, the descriptions, methods and diagrams of should not be read as limited to the described order of elements unless stated to that effect.

Although this disclosure has described and illustrated certain embodiments, it is to be understood that the disclosure is not restricted to those particular embodiments. Rather, the disclosure includes all embodiments that are functional and/or equivalents of the specific embodiments and features that have been described and illustrated.

What is claimed:
1. A covalently crosslinked hydrogel, comprising:
 a protein polymer, comprising silk fibroin having phenolic side chains,
  wherein the covalently crosslinked hydrogel is formed from combining an aqueous silk fibroin solution with a peroxidase and a peroxide, wherein the silk fibroin solution consists essentially of water and the silk fibroin in an amount of 0.1% (w/v or w/w) to 10% (w/v or w/w), and wherein the covalently crosslinked hydrogel is characterized by beta-sheet secondary structure and covalent crosslinks formed between phenolic side chains of the silk fibroin,
wherein the covalently crosslinked hydrogel is further characterized by a storage modulus value in a range of about 50 Pa to about 100 kPa without an indication of a plastic deformation,
wherein the covalently crosslinked hydrogel is free of phosphate buffered saline (PBS) solution, and
wherein the covalently crosslinked hydrogel has at least one further characteristic selected from the group consisting of:
  swelling up to 400% when exposed to solvent;
  recovery from a shear strain of at least 100% without showing an indication of a plastic deformation;
  recovery from a compressive strain of at least 75% without showing an indication of a plastic deformation; and
  a tangent modulus between about 200 Pa to about 400 kPa.

2. The covalently crosslinked hydrogel of claim 1, further comprising elastin, collagen, gelatin, resilin, or combinations thereof.

3. The covalently crosslinked hydrogel of claim 1, wherein covalently crosslinked the hydrogel is further characterized by negligible absorbance above 290 nm so that the covalently crosslinked hydrogel is optically clear.

4. The covalently crosslinked hydrogel of claim 1, wherein the covalently crosslinked hydrogel is configured to support encapsulation of cells, incorporation of functional moieties, or incorporation of at least one agent.

5. The covalently crosslinked hydrogel of claim 1, wherein the silk fibroin is further characterized by hydrogen bonding.

6. A method of manufacturing a covalently crosslinked hydrogel, comprising steps of:
  providing a protein polymer, comprising silk fibroin having phenolic side chains,
    wherein the silk fibroin has an average molecular weight in a range from 100 kDa to 400 kDa;
  solubilizing the silk fibroin to form an aqueous silk fibroin solution consisting essentially of silk fibroin and water,
    wherein a concentration of the aqueous silk fibroin solution is in a range of 0.1 wt % to 10 wt %;
  providing a solution of peroxidase;
  combining the aqueous silk fibroin solution with the solution of peroxidase;
  inducing a gelation reaction in the combined solution when a peroxide is added to the combined solution; and
  covalently crosslinking at least some of the phenolic side chains of the silk fibroin thereby forming a hydrogel,
  wherein the hydrogel is characterized by beta-sheet secondary structure and further characterized by a storage modulus value in a range of about 50 Pa and to about 100 kPa without an indication of a plastic deformation,
  wherein the hydrogel has at least one further characteristic selected from the group consisting of:
    swelling up to 400% when exposed to solvent;
    recovery from a shear strain of at least 100% without showing an indication of a plastic deformation;
    recovery from a compressive strain of at least 75% without showing an indication of a plastic deformation; and
    a tangent modulus between about 200 Patent application to about 400 kPa.

7. The method of claim 6, the step of inducing the gelation reaction in the combined solution when the peroxide is added to the combined solution, wherein the peroxide comprises hydrogen peroxide, barium peroxide, calcium peroxide, sodium peroxide, organic peroxides or combinations thereof.

8. The method of claim 6, the step of inducing the gelation reaction in the combined solution when the peroxide is added to the combined solution, wherein the peroxide concentration is between 0.01 wt % and 30 wt %.

9. The method of claim 6, further comprising incorporating functional moieties, incorporating at least one agent, or encapsulating a plurality of cells.

10. The method of claim 9, further comprising releasing the at least one agent when the hydrogel degrades.

11. The method of claim 6, further comprising tuning the storage modulus value.

12. The method of claim 11, the step of tuning the storage modulus value comprises varying the concentration of the aqueous silk fibroin solution between 0.5 wt % and 30 wt %.

13. The method of claim 6, further comprising molding channels into the hydrogel, whereby the channels enhance diffusion of oxygen and nutrients and promote vascularization.

14. A pharmaceutical composition comprising the covalently crosslinked hydrogel of claim 1, further comprising: a plurality of cells, wherein a cell shape is influenced when the storage modulus value is tuned, thereby effecting an elasticity of the hydrogel.

15. The pharmaceutical composition comprising the covalently crosslinked hydrogel of claim 14, wherein the hydrogel is configured to be in an injectable dosage form.

16. A covalently crosslinked hydrogel prepared by a process comprising steps of:
  providing a solution of silk fibroin having phenolic side chains, wherein the silk fibroin solution consists essentially of water and silk fibroin in an amount of 0.1% (w/v or w/w) to 10% (w/v or w/w);
  providing a solution of peroxidase, wherein the peroxidase is free of phosphate buffered saline (PBS) solution;
  combining the polymer solution with the solution of peroxidase;
  inducing a gelation reaction in the combined solution when a peroxide is added to the combined solution; and
  covalently crosslinking at least some of the phenolic side chains of the silk fibroin forming a hydrogel,
    wherein the hydrogel is further characterized by beta-sheet secondary structure and by a storage modulus value in a range of about 50 Pa to about 100 kPa without an indication of a plastic deformation,
    wherein the hydrogel is free of PBS solution;
    wherein the silk fibroin has an average molecular weight in a range from 100 kDa to 400 kDa;
    wherein the hydrogel has at least one further characteristic selected from the group consisting of:
      swelling up to 440% when exposed to solvent;
      recovery from a shear strain of at least 100% without showing an indication of a plastic deformation;
      recovery from a compressive strain of at least 75% without showing an indication of a plastic deformation; and
      a tangent modulus between about 200 Pa to about 400 kPa.

17. The covalently crosslinked hydrogel of claim 16, prepared by a process, wherein the step of providing the solution of the silk fibroin having phenolic side chains further comprises selecting a molecular weight of the silk fibroin for matching, tuning, adjusting, and/or manipulating mechanical properties of the hydrogel.

* * * * *